(12) United States Patent
Rehbein et al.

(10) Patent No.: US 11,399,984 B2
(45) Date of Patent: Aug. 2, 2022

(54) NEGATIVE-PRESSURE TREATMENT WITH AREA STABILIZATION

(71) Applicant: KCI Licensing, Inc., San Antonio, TX (US)

(72) Inventors: Jonathan G. Rehbein, San Antonio, TX (US); Richard Marvin Kazala, Jr., San Antonio, TX (US); Larry Tab Randolph, San Antonio, TX (US); Tyler H. Simmons, San Antonio, TX (US); Shervin Jahanian, San Antonio, TX (US); Dane Anderson, Los Angeles, CA (US); Sara Cinnamon, San Francisco, CA (US); Stefan Foulstone, San Francisco, CA (US); Charles Hartzell, San Mateo, CA (US); Stephanie Henze, San Mateo, CA (US); Colton Sanford, San Francisco, CA (US)

(73) Assignee: KCI Licensing, Inc., San Antonio, TX (US)

( * ) Notice: Subject to any disclaimer, the term of this patent is extended or adjusted under 35 U.S.C. 154(b) by 87 days.

(21) Appl. No.: 16/831,451

(22) Filed: Mar. 26, 2020

(65) Prior Publication Data

US 2020/0306092 A1    Oct. 1, 2020

Related U.S. Application Data

(60) Provisional application No. 62/826,092, filed on Mar. 29, 2019.

(51) Int. Cl.
*A61F 13/00* (2006.01)
*A61M 1/00* (2006.01)

(52) U.S. Cl.
CPC ......... *A61F 13/00068* (2013.01); *A61M 1/90* (2021.05); *A61F 2013/00174* (2013.01);
(Continued)

(58) Field of Classification Search
CPC .... A61F 13/00068; A61F 5/01; A61F 5/0102; A61F 5/0111; A61F 2013/00174;
(Continued)

(56) References Cited

U.S. PATENT DOCUMENTS 1,355,846 A   10/1920  Rannells
1,767,320 A    6/1930  Oreste
(Continued)

FOREIGN PATENT DOCUMENTS

AU    550575 B2    3/1986
AU    745271 B2    3/2002
(Continued)

OTHER PUBLICATIONS

International Search Report and Written Opinion for corresponding Application No. PCT/US2020/025026, dated Aug. 24, 2020.
(Continued)

*Primary Examiner* — Susan S Su
*Assistant Examiner* — Eric Rassavong

(57) ABSTRACT

An apparatus for applying negative pressure to a tissue site of a patient may include a tissue interface, a cover, an aperture in the cover, and a sealing member. The tissue interface may have an anatomical shape configured to cover the tissue site. The cover may be configured to cover the tissue interface. The aperture in the cover may be fluidly coupled to the tissue interface. The sealing member may be configured to seal the cover to the patient, wherein the cover and the sealing member are configured to cooperate to form a sealed chamber containing the tissue interface. The tissue interface may be coupled to a source of negative pressure,
(Continued)

which can be delivered to the tissue interface for distribution to the tissue site. The source of negative pressure may be coupled to the cover of the apparatus.

26 Claims, 46 Drawing Sheets

(52) U.S. Cl.
CPC .............. *A61F 2013/00634* (2013.01); *A61F 2013/00778* (2013.01); *A61M 2210/086* (2013.01)

(58) Field of Classification Search
CPC .... A61F 2013/00634; A61F 2013/0078; A61F 2013/0063; A61M 1/90; A61M 2210/086; A61M 2210/08
See application file for complete search history.

(56) References Cited

U.S. PATENT DOCUMENTS

| | | | |
|---|---|---|---|
| 2,060,063 A | 11/1936 | Frimand | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,263,679 A * | 8/1966 | Hass | A61F 13/045 |
| | | | 602/10 |
| 3,367,332 A | 2/1968 | Groves | |
| 3,487,832 A * | 1/1970 | Spence | A61F 13/063 |
| | | | 128/894 |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,802,424 A * | 4/1974 | Newell | A61F 13/043 |
| | | | 602/3 |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Bustad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,113,599 A | 5/1992 | Cohen et al. | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,439,104 B1 | 8/2002 | Tonogai et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,916,301 B1 | 7/2005 | Clare | |
| 7,290,660 B2 | 11/2007 | Tilman et al. | |
| 7,762,973 B2 | 7/2010 | Einarsson et al. | |
| 7,837,387 B2 | 11/2010 | Newrones et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,119,705 B2 * | 9/2015 | Parish | A61F 7/02 |
| 9,198,801 B2 | 12/2015 | Weston | |
| 9,211,365 B2 | 12/2015 | Weston | |
| 9,289,542 B2 | 3/2016 | Blott et al. | |
| 9,510,965 B2 | 12/2016 | Grim et al. | |
| 10,383,773 B2 | 8/2019 | Han | |

(56) References Cited

U.S. PATENT DOCUMENTS

| | | | |
|---|---|---|---|
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0215120 A1* | 10/2004 | Jensen | A61F 13/04 602/8 |
| 2005/0203452 A1 | 9/2005 | Weston et al. | |
| 2007/0092167 A1 | 4/2007 | Tilman et al. | |
| 2007/0167884 A1* | 7/2007 | Mangrum | A61H 9/005 601/6 |
| 2008/0319362 A1* | 12/2008 | Joseph | A61F 5/055 602/7 |
| 2009/0124944 A1* | 5/2009 | Ravikumar | A61M 27/00 601/149 |
| 2009/0125004 A1 | 5/2009 | Shen et al. | |
| 2009/0234259 A1* | 9/2009 | Hardman | A61H 9/0057 601/134 |
| 2009/0234260 A1* | 9/2009 | Coward | A61M 1/82 601/148 |
| 2010/0179463 A1* | 7/2010 | Greener | B26F 1/02 602/52 |
| 2010/0210986 A1* | 8/2010 | Sanders | A61B 46/27 602/41 |
| 2010/0268198 A1* | 10/2010 | Buan | A61F 13/0216 604/543 |
| 2011/0077570 A1* | 3/2011 | Findeisen | A61F 5/019 602/30 |
| 2012/0041399 A1 | 2/2012 | Blott et al. | |
| 2013/0090586 A1* | 4/2013 | Dennis | A61F 13/066 602/27 |
| 2013/0123722 A1 | 5/2013 | Pratt et al. | |
| 2014/0163491 A1 | 6/2014 | Schuessler et al. | |
| 2014/0171837 A1* | 6/2014 | Harcourt | A61F 5/05833 601/7 |
| 2014/0276288 A1* | 9/2014 | Randolph | A61H 9/0057 601/152 |
| 2015/0080788 A1 | 3/2015 | Blott et al. | |
| 2016/0213823 A1 | 7/2016 | Walborn et al. | |
| 2017/0100525 A1 | 4/2017 | Heaton et al. | |
| 2018/0228653 A1 | 8/2018 | Kilpadi | |
| 2018/0272052 A1 | 9/2018 | Locke et al. | |
| 2020/0038283 A1 | 2/2020 | Hall et al. | |
| 2020/0069476 A1 | 3/2020 | Randolph et al. | |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2195255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/20041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2010011148 A1 | 1/2010 | |
| WO | WO-2010011148 A1 * | 1/2010 | ....... A61F 13/00068 |
| WO | 2019002086 A2 | 1/2019 | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, Nos. May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al.; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp : 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction Around drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

(56) References Cited

OTHER PUBLICATIONS

Arnljots, Bjorn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D E. Tribble, An Improved Sump Drain-Irrigation Device of Simple Construction, Archives of Surgery 105 (1972) pp. 511-513.

M.J. Morykwas, L.C. Argenta, E.L Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties X Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.L Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II AllUnion Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for Corresponding Application No. PCT/US2020/025039, dated Jul. 9, 2020.
"Flexis Valve Labels from CCL" (https://ccllabel.com/portfolios/specialty-products-valves-labels/) 2019 CCL Industries.
International Search Report and Written Opinion for Corresponding Application No. PCT/US2019/044227, dated Dec. 18, 2019.
International Search Report and Written Opinion for Corresponding Application No. PCT/US2020/025035 dated Jun. 18, 2020.
International Search Report and Written Opinion for corresponding application No. PCT/US2020/025019 dated Aug. 11, 2020.
Chinese First Office Action Corresponding to Application No. 2020800255837, dated Apr. 25, 2022.

\* cited by examiner

NEGATIVE-PRESSURE TREATMENT WITH AREA STABILIZATION

RELATED APPLICATION

This application claims the benefit, under 35 U.S.C. § 119(e), of the filing of U.S. Provisional Patent Application Ser. No. 62/826,092 entitled "NEGATIVE-PRESSURE TREATMENT WITH AREA STABILIZATION," filed Mar. 29, 2019, which is incorporated herein by reference for all purposes.

TECHNICAL FIELD

The invention set forth in the appended claims relates generally to tissue treatment systems and more particularly, but without limitation, to dressings for tissue treatment with negative pressure and methods of using the dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

Additionally, the application of negative therapy may be beneficial for the healing of sprains or strains at tissue sites where there may be no open wound.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

In some embodiments, an apparatus for applying negative pressure to a tissue site of a patient may comprise a tissue interface, a cover, an aperture in the cover, and a sealing member. The tissue interface may have an anatomical shape configured to cover the tissue site. The cover may be configured to cover the tissue interface. The aperture in the cover may be fluidly coupled to the tissue interface. The sealing member may be configured to seal the cover to the patient, wherein the cover and the sealing member are configured to cooperate to form a sealed chamber containing the tissue interface.

In some embodiments, the tissue interface may be configured to circumferentially cover a portion of a leg, at least a portion of an ankle, and a portion of a foot of the patient.

In some embodiments, the tissue interface may be configured to cover the knee, a portion of the leg above the knee, and a portion of the leg below the knee.

In some embodiments, the tissue interface is further configured to cover at least a portion of the shoulder of the patient proximate the tissue site.

In some embodiments, the apparatus may include a support layer configured to be located between the tissue interface and the cover. The support layer may include a plurality of apertures, wherein when negative pressure is applied to the tissue interface, at least a portion of the apertures may be visible through the cover.

In some embodiments, the apparatus may include a negative-pressure source coupled to the cover. The negative-pressure source may include a chamber wall defining a pump chamber and a base extending from the chamber wall. The pump chamber may be fluidly coupled to the tissue interface through the aperture. The base may be fluidly sealed to the cover around the aperture. The chamber wall may be adapted to be compressed to evacuate fluid from the pump chamber. The pump chamber may be adapted to expand to decrease pressure in the tissue interface.

Some example embodiments may include an apparatus for applying negative pressure to a tissue site proximate a foot of a patient, wherein the apparatus may include a tissue interface, a cap, a cover, and a sealing member. The tissue interface may have an anatomical shape configured to cover the tissue site, a portion of a leg, at least a portion of an ankle, and a portion of the foot. The cap may be configured to cover toes of the foot. The cover may have a first end that is open and may be configured to cover the tissue interface and the cap. The sealing member may include a first sealing member configured to extend around the first end of the cover to seal the first end of the cover to the leg. The cover and the first sealing member are configured to cooperate to form a sealed chamber containing the tissue interface and the cap.

Some example embodiments may include an apparatus for applying negative pressure to a tissue site proximate a foot of a patient, wherein the apparatus may include a tissue interface, a cover, and a sealing member. The tissue interface may have an anatomical shape configured to cover the tissue site, the knee of a patient, a portion of the leg of the patient above the knee, and a portion of the leg of the patient below the knee. The cover may have a first end that is open and a second end that is open. The cover may be configured to cover the tissue interface. The sealing member may include a first sealing member and a second sealing member. The first sealing member may be configured to extend around the first end of the cover and the leg of the patient above the tissue interface to seal the first end of the cover to the patient. The second sealing member may be configured to extend around the second end of the cover and the leg of the patient below the tissue interface to seal the second end of the cover to the patient. The cover, the first sealing member, and the second sealing member may be configured to cooperate to form a sealed chamber containing the tissue interface.

Some example embodiments may include an apparatus for applying negative pressure to a tissue site proximate a foot of a patient, wherein the apparatus may include a tissue interface, a cover, and a sealing member. The tissue interface may have an anatomical shape configured to cover the tissue site and at least a portion of the shoulder of the patient proximate to the tissue site. The cover may have a flange, and the cover may be configured to cover the tissue interface. The sealing member may be configured to extend around the flange to seal the cover to the patient, wherein the cover and the sealing member are configured to cooperate to form a sealed chamber containing the tissue interface.

In some embodiments, the tissue interface may be configured to cause the cover to collapse upon application of negative pressure, stiffening the cover to stabilize the tissue site and pulling the tissue site radially outward.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
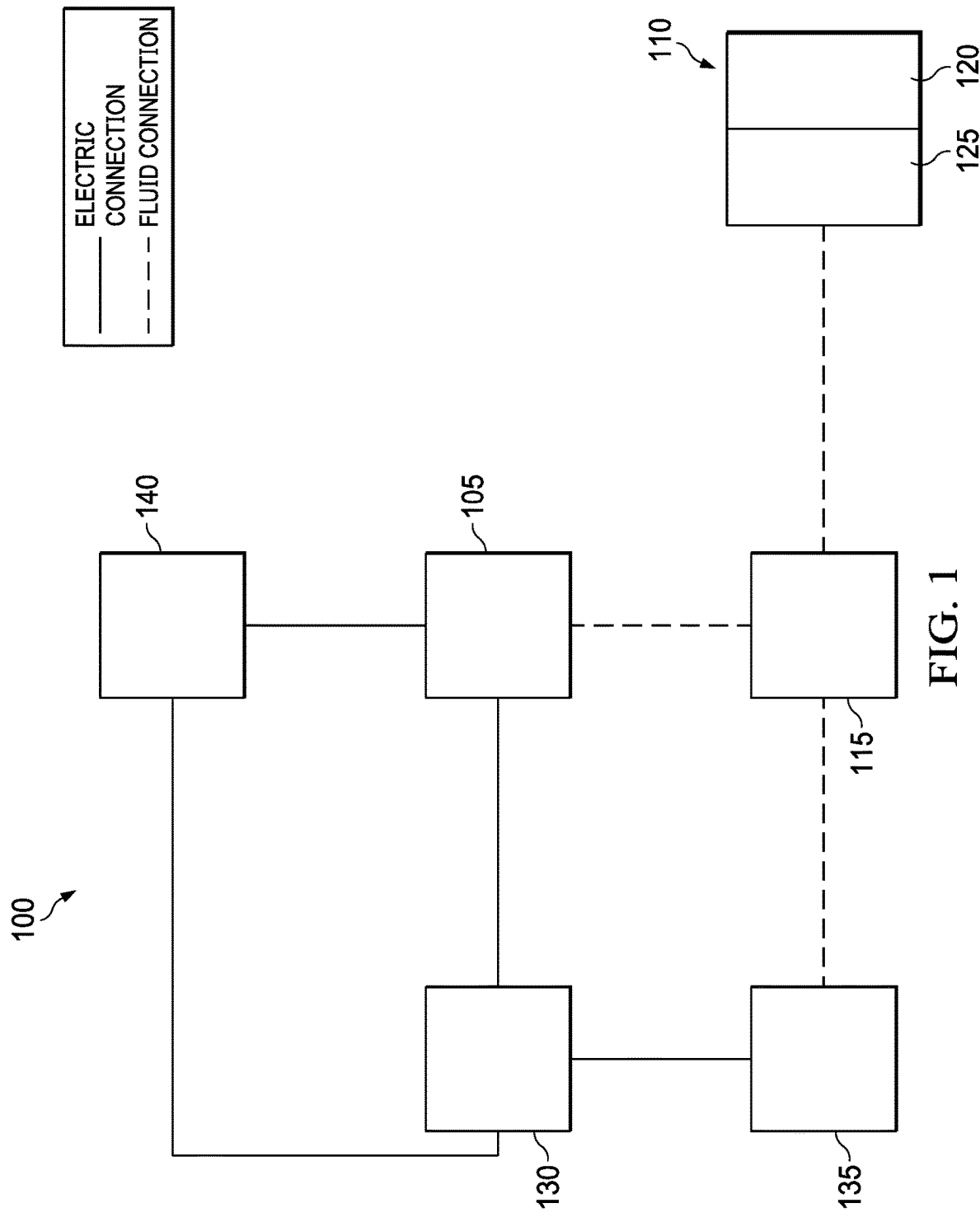
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Tex.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130 and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface 120 may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Tex.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to about 30 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours ($g/m^2/24$ hours) in some embodiments, measured using an upright cup technique according to ASTM E96/E96M Upright Cup Method at 38° C. and 10% relative humidity (RH). In some embodiments, an MVTR up to 5,000 $g/m^2/24$ hours may provide effective breathability and mechanical properties.

In some example embodiments, the cover 125 may be a polymer drape, such as a polyurethane film, that is permeable to water vapor but impermeable to liquid. Such drapes typically have a thickness in the range of about 25 to about 50 microns. In some embodiments, the cover 125 may have a thickness greater than 50 microns. In some embodiments, the cover may have a thickness in the range of about 50 microns to about 3.175 millimeters. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; polyether block polymide copolymers; and nylon. Such materials are commercially available as, for example, Tegaderm® drape, commercially available from 3M Company, Minneapolis, Minnesota; polyurethane (PU) drape, commercially available from Avery Dennison Corporation, Pasadena, Calif.; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns. In some embodiments, the cover 125 may comprise a non-porous film. In some embodiments, the cover 125 may comprise a closed-cell foam. In some embodiments, the cover 125 may comprise a nylon fabric.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

With tissue sites having open wounds, negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, the controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. For example, the target pressure may be set at a value of −135 mmHg for a specified period of time (e.g., 5 min), followed by a specified period of time (e.g., 2 min) of deactivation. The cycle can be repeated by activating the negative-pressure source 105 which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise time set at a rate of +25 mmHg/min. and a descent time set at −25 mmHg/min. In some embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

In addition to providing negative-pressure therapy to a tissue site having an open wound, the therapy system 100 described herein may be used to treat tissue sites that have intact skin or epidermis but include sprains and strains to subcutaneous tissue such as, for example, a ligament or a muscle.

Figure 2:
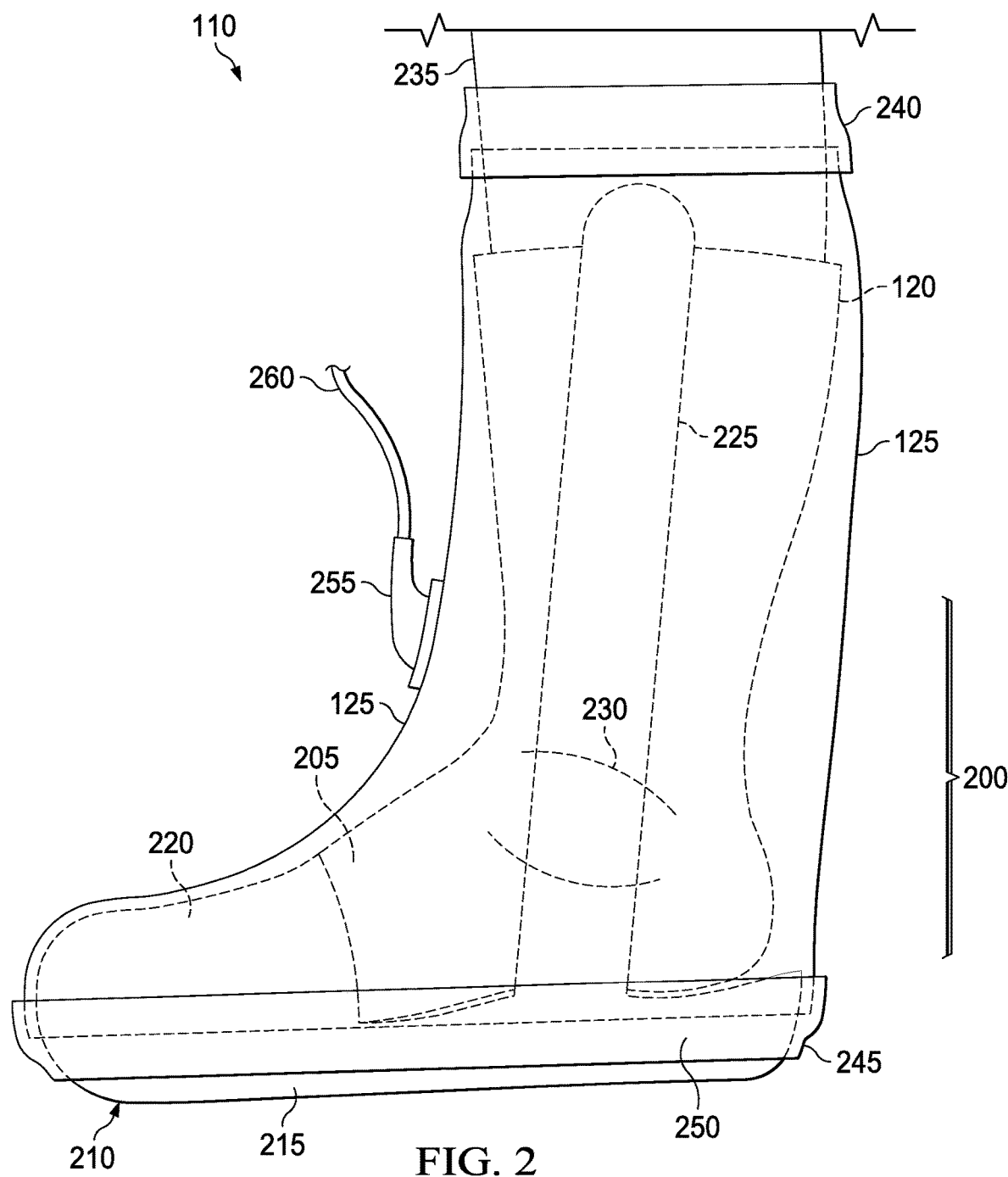
FIG. 2 is a side view of an example of a dressing, illustrating additional details that may be associated with some embodiments.

FIG. 2 is a side view of an example of the dressing 110, illustrating additional details that may be associated with some embodiments. In the example embodiment of FIG. 2, the dressing 110 is configured for delivering a negative pressure to a tissue site 200. As illustrated in the example of FIG. 2, the tissue site 200 may be on or proximate a foot 205 of a patient. The tissue interface 120 may be configured to be circumferentially disposed around the tissue site 200. Also included with the dressing 110 of FIG. 2 is a boot 210, which may comprise a sole 215, a toe box 220, and one or more optional stabilizing members 225. The boot 210 may be configured to support one or more of the foot 205, an ankle 230, and a portion of a leg 235. The cover 125 may be sealed to the leg 235 superior to the ankle 230 by a first sealing member 240 and to a perimeter 250 of the sole 215 by a second sealing member 245. The dressing 110 may further include a dressing interface 255, which can fluidly couple the tissue interface 120 to the negative-pressure source 105 via a fluid conductor 260 to deliver negative pressure to the tissue site 200.

Figure 3:
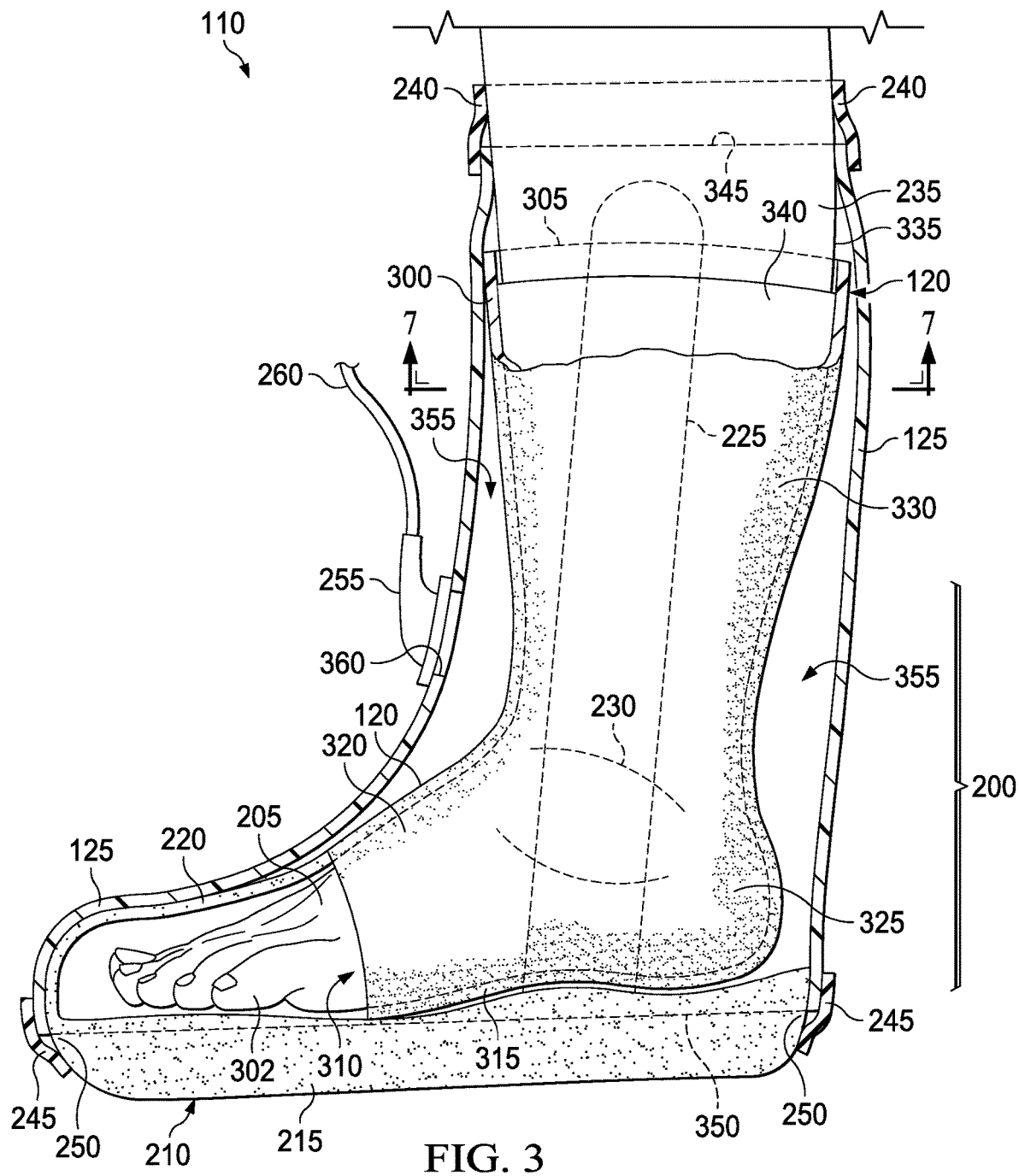
FIG. 3 is a cutaway view of the dressing of FIG. 2.

FIG. 3 is a cutaway view of the dressing 110 of FIG. 2. As shown, in some embodiments, the tissue interface 120 comprises a primary manifold 300 that conforms to the shape of a portion of the leg 235, the ankle 230, and the foot 205. The tissue interface 120 may have two open ends and may not cover the toes 302 of the patient. In some embodiments, the tissue interface 120 may be formed in the shape of an open-toed sock or a sleeve, which may be pulled over the tissue site 200.

In some embodiments, the tissue interface 120 may be molded as a single component in a generally tubular shape having a first end 305 and a second end 310 that are open, and the tissue interface 120 may be configured to be pulled over the foot 205. The toes 302 may be inserted into the tissue interface 120 through the first end 305. The tissue interface 120 may be pulled up the foot 205 such that the first end 305 extends over and past the ankle 230 and up at least a portion of the leg 235. The toes 302 of the foot 205 can extend out and beyond the second end 310 of the tissue interface 120. In some embodiments, the tissue interface 120 may be boot shaped. For example, the tissue interface 120 may have a sole portion 315, a vamp portion 320 coupled to the sole portion 315, a quarter portion 325 coupled to the sole portion 315 and the vamp portion 320, and a calf portion 330 coupled to and extending away from the quarter portion 325. In some embodiments, the tissue interface 120 may comprise a sheet or tape of open-cell foam, which can be configured to be wrapped around and circumferentially cover a portion of the leg 235, the ankle 230, and the foot 205.

The tissue interface 120 may take many forms and may come in many sizes, shapes, or thicknesses depending on a variety of factors, such as the type of treatment being provided or the nature and size of the epidermis 335 at the tissue site 200. For example, the size and shape of the tissue interface 120 may be adapted to the contours of the extremities located at a joint, such as the ankle 230. The second open end 310 of the tissue interface 120 may abut or contact the open end of the toe box 220, leaving no gap between the tissue interface 120 and the toe box 220, which may reduce or eliminate the possibility of the epidermis 335 from being pulled up and pinched between the tissue interface 120 and the toe box 220. In some embodiments, there may be a gap between the tissue interface 120 and the toe box 220 such that the second open end 310 of the tissue interface 120 does not abut or contact the toe box 220.

Additionally, in some embodiments, the tissue interface 120 may comprise a comfort layer 340, which may be positioned between the primary manifold 300 and the tissue site 200. The comfort layer 340 may be employed to provide additional comfort for the patient rather than disposing the primary manifold 300 in direct contact with the epidermis 335. The comfort layer 340 may be any material that helps prevent skin irritation without significantly impeding airflow between the tissue interface 120 and the epidermis 335. The comfort layer 340 may also be any material that wicks liquids such as sweat away from the epidermis 335 to prevent maceration. In some examples, the comfort layer 340 may be a woven material or a polyester knit textile substrate. In some embodiments, the comfort layer 340 may be a stretchable knit sock. A textile known as InterDry™ available from Milliken Chemical located in Spartanburg, S.C., may be a suitable material for some embodiments of the comfort layer 340. The comfort layer 340 may also include antimicrobial substances or lubricants. In some embodiments, instead of a separate layer, the comfort layer 340 may be coupled, for example by a heat bond or any other technique, to the primary manifold 300, or may be an integral component of the primary manifold 300.

The boot 210 in the example of FIG. 3 is configured to support the tissue interface 120. Following application of the tissue interface 120 on the leg 235, the ankle 230, and the foot 205 of the patient, the foot 205 may be placed into the boot 210. The toes 302 of the patient may be received in the toe box 220 of the boot 210 and the sole of the patient may be supported by the sole 215 of the boot 210. The boot 210 may provide support and/or immobilize the tissue site 200 if appropriate or necessary. The toe box 220 may be sufficiently rigid to prevent collapse and support the cover 125 if subjected to negative pressure from the negative-pressure source 105. The toe box 220 may be configured to prevent the toes 302 of the patient from being compressed by the cover 125 if negative pressure is supplied to the tissue interface 120. In some embodiments, the toe box 220 may be formed from a closed-cell foam. The use of closed-cell foam for the toe box 220 may also allow for the transition from the toe box 220 to the tissue interface 120 to be minimized, which may reduce or eliminate the chance for blister formation. Additionally, in some embodiments, the toe box 220 may have a thickness that is equal or substantially equal to a thickness of the tissue interface 120. In some embodiments, the toe box 220 may comprise a rigid plastic or composite material. As shown in the example FIG. 3, the toe box 220 may be integrally formed with the sole 215. In some embodiments, the toe box 220 may be separately manufactured and permanently or releasably coupled to the sole 215. In some embodiments, the toe box 220 may be clear or transparent to permit a patient or a physician to view the toes 302 of the patient through the toe box 220 to check for blood flow or circulation through the toes 302. In some embodiments, the toe box 220 may be colored (e.g., skin colored).

Additionally, in some embodiments, the boot 210 may further include one or more stabilizing members 225, which can extend away from the sole 215 along and proximate the calf portion 330 of the tissue interface 120. In some examples, a first stabilizing member 225 may extend from a medial side of the sole 215 and a second stabilizing member (not shown) may extend from a lateral side of the sole 215. The first stabilizing member 225 and the second stabilizing member may be generally aligned with the ankle 230 and the fibula and/or tibia of the patient. The first stabilizing member 225 and the second stabilizing member may stabilize the tissue interface 120 and/or the ankle 230 of the patient. The sole 215 and the first stabilizing member 225 and the second stabilizing member, if included, may be sufficiently rigid to protect the tissue interface 120 from being compressed by contact from the external environment that collapses the tissue interface 120, preventing the tissue interface 120 from distributing negative pressure to the tissue site 200.

As illustrated in the example of FIG. 3, the cover 125 may have a tubular or sleeve shape and may have a first end 345 and a second end 350 that are open. The first end 345 of the cover 125 may be sealed to the leg 235 of the patient superior to the tissue interface 120 by the first sealing member 240, which can extend around the leg 235. The second end 350 may be sealed to the sole 215 of the boot 210 by the second sealing member 245, which can extend around the sole 215. In some examples, the second end 350 may have a larger diameter than the diameter of the first end 345. The cover 125 of FIG. 3 is configured to fit over the tissue interface 120 and the sole 215. The cover 125 and the sole 215 can cooperate to form a chamber 355 containing the tissue interface 120 and to seal the tissue interface 120 within the chamber 355. The cover 125 may comprise a sealing material that can provide a fluid seal between two environments or components, such as, for example, between a therapeutic environment adjacent the tissue site 200 and a local external environment surrounding the cover 125. In some embodiments, the cover 125 may be configured to be wrapped around and circumferentially cover the tissue interface 120 and at least a portion of the boot 210. The cover 125 may also extend circumferentially around the tissue site 200, and in cooperation with the sole 215, the first sealing member 240, and the second sealing member 245, can form the chamber 355 enclosing the tissue site 200 to provide a negative-pressure environment. A negative pressure from the negative-pressure source 105 may be distributed to the tissue site 200 by the tissue interface 120. The sealing material forming the cover 125 may be, for example, an impermeable or semi-permeable material that provides a seal adequate to maintain a desired negative pressure within the chamber 355. In some embodiments, the cover 125 may be molded as a single component in a generally tubular shape formed from the sealing material that is stretched over the foot 205 and at least a portion of the leg 235. The cover 125 may fit over the tissue interface 120 and the sole 215 of the boot 210. The cover 125 may have a thickness in a range of about 25 to about 50 microns. However, the cover 125 may have a thickness greater than 50 microns. In some embodiments, the cover 125 may have a thickness in the range of about 25 microns to about 3.175 millimeters.

The first sealing member 240 and the second sealing member 245 are examples of attachment devices, which can be configured to seal the cover 125 to the patient and the sole 215, respectively. For example, the first sealing member 240 may be an elastic tape wrapped around the first end 345 of the cover 125 against the epidermis 335 to provide a fluid seal at the first end 345 of the cover 125. In some embodiments, the first sealing member 240 may be disposed between the cover 125 and the epidermis 335 for attaching the cover 125 to an attachment surface, such as the epidermis 335, a gasket, or another sealing member. The first sealing member 240 may also be an adhesive material configured to prevent the cover 125 from slipping down the leg 235. For example, the first sealing member 240 may be a silicone tape or adhesive gasket. The first sealing member 240 may take many forms that can provide both sealing and adhesive qualities without irritating or macerating the epidermis 335. The first sealing member 240 may be a medically-acceptable, pressure-sensitive adhesive that extends around the periphery of the first end 345 of the cover 125 to provide an airtight seal between the epidermis 335 and the cover 125. Other exemplary embodiments of the first sealing member 240 may include a double-sided tape, paste, hydrocolloid, hydrogel, silicone gel, organogel, or an acrylic adhesive. In some embodiments, the first sealing member 240 may be non-adhesive. For example, the first sealing member 240 may comprise a neoprene sleeve that can be secured on the leg 235 and over the cover 125 to provide a fluid seal. In some embodiments, the first sealing member 240 may comprise a silicone gasket or ring seal having a central aperture through which the patient may insert their leg 235. For example, such a ring seal may be a diaphragm from the SEAL-TIGHT cast and bandage protector available from Brownmed of Boston, Mass.

The second sealing member 245 may also be an elastic tape in some embodiments. For example, the second sealing member 245 may be an elastic tape that can be wrapped around the second end 350 of the cover 125 against the sole 215 to provide a fluid seal at the second end 350 of the cover 125. The second end 350 of the cover 125 may be placed at or over the perimeter 250 of the sole 215. The second sealing member 245 may be wrapped around the perimeter 250 of the sole 215 and the second end 350 of the cover 125 to seal the cover 125. In some embodiments, the second sealing member 245 may be disposed between the cover 125 and the sole 215 for attaching the cover 125 to an attachment surface such as, for example, a gasket, another sealing member, or the sole 215. The second sealing member 245 may also be an adhesive material that prevents the cover 125 from slipping up from the sole 215. The second sealing member 245 may take many forms that can provide both sealing and adhesive qualities. In some embodiments, the second sealing member 245 may be the same as the first sealing member 240. For example, the second sealing member 245 may also be a medically-acceptable, pressure-sensitive adhesive that extends around the periphery of the second end 350 of the cover 125 to provide an airtight seal between the sole 215 and the cover 125. Other exemplary embodiments of the second sealing member 245 may include a double-sided tape, paste, hydrocolloid, hydrogel, silicone gel, organogel, or an acrylic adhesive. Although the second end 350 of the cover 125 is shown in FIG. 3 as extending around the perimeter 250 of the sole 215, in some embodiments the second end 350 of the cover 125 may extend partially around the perimeter 250 of the sole 215 and then may extend over the toe box 220. The second sealing member 245 may follow a similar path or shape to fluidly seal the cover 125 to the boot 210. In some embodiments, for example, the second end 350 of the cover 125 may be sealed to another portion of the boot 210.

A negative pressure may be supplied to the chamber 355 via a fluid conductor 260 and a dressing interface 255. The fluid conductor 260 may be a flexible tube, for example, that can be fluidly coupled on one end to the dressing interface 255. The dressing interface 255 may be an elbow connector, as shown in the example of FIG. 3, which can be placed over an aperture 360 in the cover 125 to provide a fluid path between the fluid conductor 260 and the tissue interface 120.

Because the dressing 110 may be positioned on the epidermis 335 for a prolonged period of time, the tissue interface 120 may possess an antimicrobial property to mitigate the risk of fungal infection and the spread of such infections caused by perspiration and warm temperatures in the chamber 355. The antimicrobial property of the tissue interface 120 may reduce the effect of VOCs to reduce odors being generated by the dressing 110. The antimicrobial property may be achieved by means of a silver coating that covers the tissue interface 120 or by a silver additive to the cover 125. Using a tissue interface 120 having an antimicrobial property may be used in conjunction with a charcoal filter (not shown) in connection with providing a negative pressure to the dressing 110 via the fluid conductor 260 to further reduce odors generated by the dressing 110.

Figure 4:
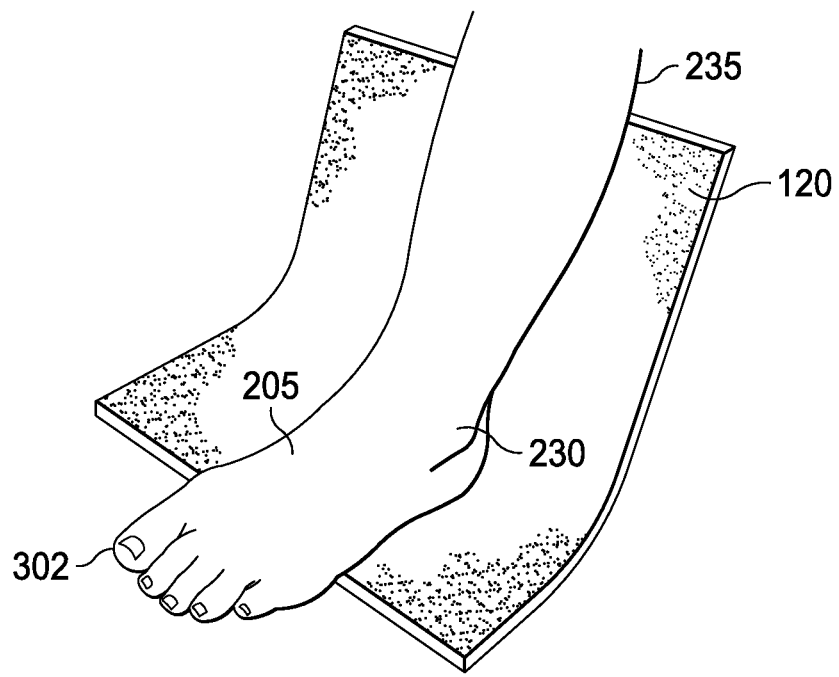
FIG. 4 and FIG. 5 are isometric views of an example of a tissue interface, illustrating additional details that may be associated with some dressings.
Figure 5:
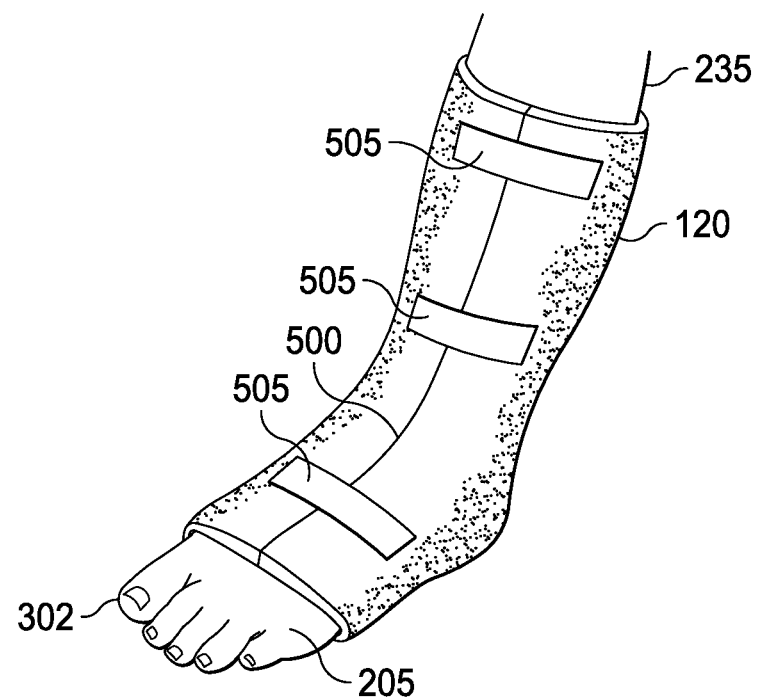

FIG. 4 and FIG. 5 are isometric views of an example embodiment of the tissue interface 120 that may be associated with some dressings 110. As shown in the example of FIG. 4, the tissue interface 120 may be formed of a sheet of material that may be placed against the patient and may be wrapped around at least a portion of the foot 205, the ankle 230, and the leg 235. The tissue interface 120 may have an anatomical shape in some embodiments, or may be shaped such that when wrapped around the patient it is anatomically shaped or conforms to an anatomical shape. For example, in FIG. 5 the tissue interface 120 has a shape configured to conform to at least a portion of the foot 205, the ankle 230, and the leg 235. Additionally shown in the example of FIG. 5, the tissue interface 120 may form a seam 500 where the tissue interface 120 abuts against itself when wrapped around the patient. Although a single seam 500 is illustrated in the example of FIG. 5, the tissue interface 120 may form multiple seams when wrapped around the patient. Additionally, although the seam 500 is illustrated as extending generally in a line down the front of the leg 235 and the foot 205, the one or more seams 500 may be non-linear and may be located along other portions of the leg 235 and foot 205 of the patient. As further illustrated in the example of FIG. 5, one or more straps 505 may be coupled to the tissue interface 120 over the seams 500 to close the seams 500 and to ensure that the seams 500 remain closed when the dressing 110 is in use. The straps 505 may prevent the seams 500 from opening or spreading apart if a negative pressure is applied to the tissue interface 120. In some embodiments, the straps 505 may couple to the tissue interface 120 via an adhesive (e.g., a pressure-sensitive adhesive), a hook-and-loop style fastener (e.g., VELCRO fastener), or any other suitable coupling mechanism. In some embodiments, as shown in the example of FIG. 5, the straps 505 may be short and may only extend around a portion of the tissue interface 120. In some embodiments, at least one of the straps 505 may extend circumferentially around the tissue interface 120 and couple with itself. In some embodiments, the straps 505 may comprise an elastic loop, which can be stretched and slid up the tissue interface 120 and if released, can hold the tissue interface 120 in place by the tension in the strap 505. As shown in FIG. 5, the tissue interface 120 may not cover the toes 302 of the patient. The tissue interface 120 shown in FIG. 5 may be particularly beneficial for patients whose injury to the tissue site is severe enough such that the patient is unable to insert their foot 205 into and through a tubular shaped tissue interface 120.

Figure 6:
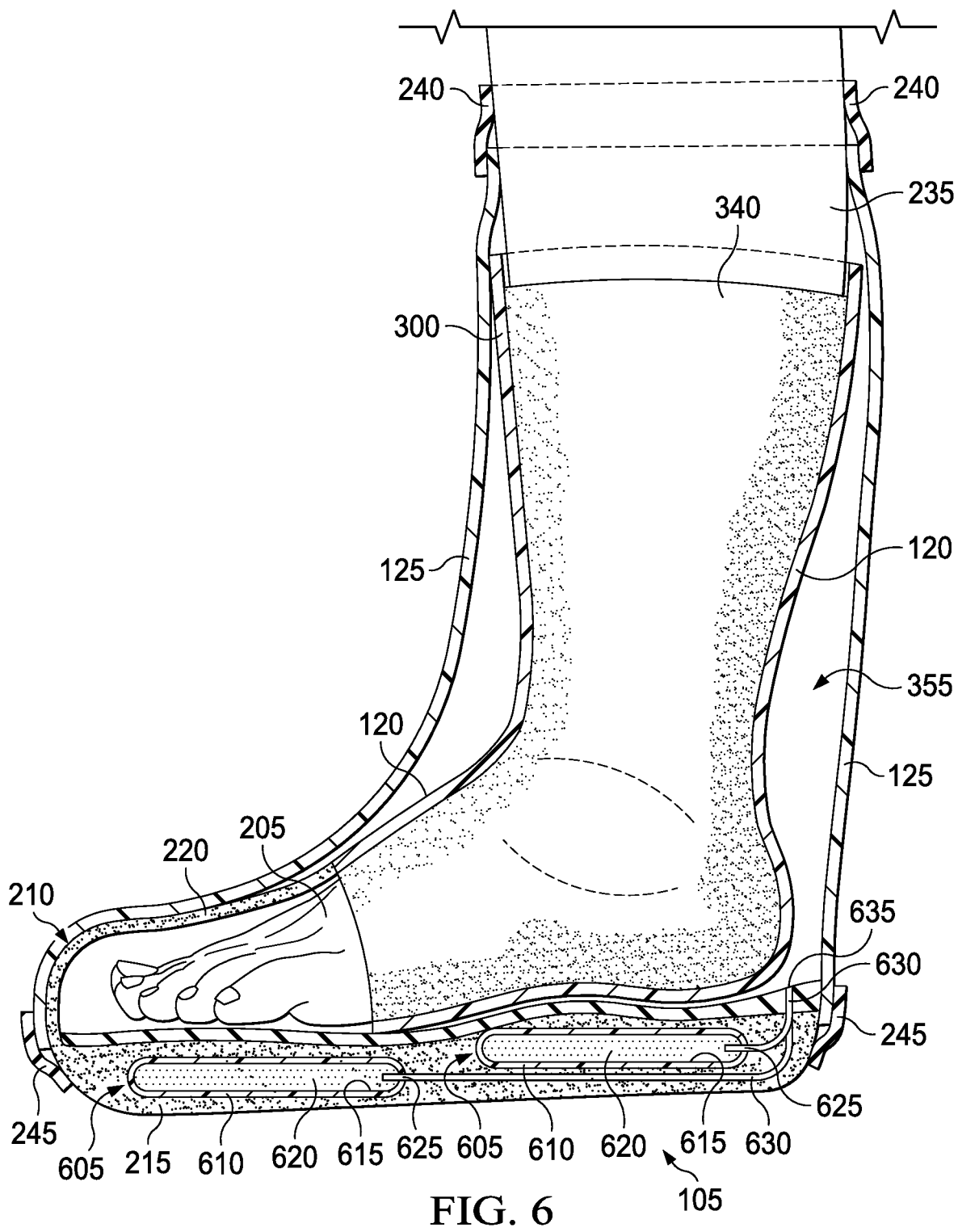
FIG. 6 is a cutaway view of another example of a dressing, illustrating additional details that may be associated with some embodiments.

FIG. 6 is a cutaway view of another example of the dressing 110, illustrating additional details that may be associated with some embodiments. In the example embodiment of FIG. 6, the negative-pressure source 105 is contained within the boot 210. In some embodiments, the negative-pressure source 105 may be a compressible bladder system located in the sole 215 of the boot 210 that is operable by the patient. For example, the negative-pressure source 105 may comprise two or more compressible bladders 605. Each compressible bladder 605 may include a chamber wall 610 that substantially encloses a chamber 615.

The compressible bladders 605 are moveable between a compressed position and an expanded position to generate negative pressure. A resilient member 620, such as an open-cell foam, can be disposed within the chamber 615 to bias the compressible bladder 605 toward the expanded position.

In operation the compressible bladders 605 of FIG. 6 are positioned beneath the foot 205 of a patient. One of the compressible bladders 605 may be positioned under a heel region of the foot 205, and another of the compressible bladders 605 may be preferably positioned under a forefoot region of the foot 205. As the weight of the patient is exerted on a particular compressible bladder 605, the compressible bladder 605 is compressed to the compressed position and gas (e.g. air) that is within the chamber 615 is ejected through an outlet (not shown) and an outlet valve (not shown). As the weight of the patient is lifted from the compressible bladder 605 that has been compressed, the compressible bladder 605 begins to move toward the expanded position. The movement of the compressible bladder 605 toward the expanded position may be aided by the biasing member 620. As the compressible bladder 605 expands, a volume of the chamber 615 increases, which creates a negative pressure within the chamber 615. This negative pressure within the chamber 615 pulls fluid into the chamber 615 through an inlet valve (not shown) and the inlet 625. The reduced pressure generated by the compressible bladder 605 during expansion may be transmitted to the tissue interface 120 by the fluid conductors 630, which are fluidly coupled to the chamber 615 and the inlets 625 of each of the compressible bladders 605. As shown in example FIG. 6, the fluid conductors 630 may be located within the boot 210 and may have an inlet 635 located in the boot 210 within the chamber 615. If the inlets 635 of the fluid conductors 630 are located within the chamber 615, the fluid conductors 630 do not need to be mechanically coupled to the cover 125 in order to provide negative pressure to the tissue interface 120. The compressible bladder system may eliminate the need to include the dressing interface 255 or the aperture 360 in the cover 125. Additionally, by including the compressible bladder system in the boot 210, the need for an external negative-pressure source may be eliminated.

A method of treating the tissue site 200 with negative pressure may be carried out utilizing the dressing 110. Some embodiments of the dressing 110 may be configured for treating a foot. Other exemplary embodiments of the dressing 110 may be suitable for the treatment of ligaments or muscles associated with other joints such as, for example, a knee, ankle, wrist, or elbow joint. The method may comprise disposing circumferentially the tissue interface 120 around the tissue site. The method may further include enclosing the tissue interface 120 with the cover 125. The cover 125 may then be sealed around the leg 235 superior to the tissue interface 120. A first sealing member 240 may be used to seal the cover 125 around the leg 235. In some embodiments, for example, where the first sealing member 240 comprises a silicone ring or gasket, the first sealing member 240 may be applied around the leg 235 of the patient above the tissue site 200 prior to disposing the tissue interface 120 on the patient. The method may then continue with inserting the tissue interface 120 into the sole 215 of the boot 210 and inserting the toes 302 of the patient into the toe box 220 coupled to the sole 215. The cover 125 may then be sealed to the sole 215. The second sealing member 245 may be used to seal the cover 125 to the sole 215. The method may further include fluidly coupling the tissue interface 120 to the negative-pressure source 105. In some embodiments, for example, a dressing interface 255 may fluidly couple the negative-pressure source 105 to the tissue interface 120. Negative pressure may then be applied to the tissue site 200 through the tissue interface 120 within the sealed space between the cover 125 and the tissue site 200. The application of negative pressure can cause the cover 125 to collapse and stiffen, which can stabilize the tissue site 200. The epidermis 335 can also be pulled radially outward by the negative pressure, which can promote perfusion at the tissue site 200.

Such modes of treatment may be particularly advantageous for sprains and other damage to soft tissue. For example, some embodiments of the dressing 110 may cover only intact skin over a portion of the tissue site 200 having a sprain, without being wrapped around a limb. For example, if a sprain is close to the epidermal tissue, such embodiments may be applied more locally to that portion of intact skin that is adjacent the sprain.

The tissue interface 120 may be disposed proximate the epidermis 335 that extends over or around the tissue site 200 so that the chamber 355 envelops the sprain injury at the tissue site 200. The cover 125 can cover the tissue interface 120 to seal or enclose the tissue interface 120 and the epidermis 335 of the tissue site 200 within the chamber 355. Consequently, the cover 125 can also extend over the epidermis 335 of the tissue site 200, essentially forming the chamber 355 and enclosing the tissue site 200 to provide a negative-pressure environment wherein the negative pressure is distributed to the intact skin by the tissue interface 120. The dressing 110 can provide a sealed therapeutic environment proximate to the epidermis 335 surrounding a tissue site 200 and substantially isolated from the external, ambient environment outside the cover 125. In FIG. 2, FIG. 3, and FIG. 4, the dressing 110 is shown without applying a negative pressure to the tissue interface 120. If negative pressure is applied to the chamber 355, the cover 125 may collapse until most of the air is removed from the chamber 355. The cover 125 can initially collapse against the epidermis 335 surrounding the tissue site 200 and provides a certain amount of stiffening that can function like a splint to stabilize the tissue site 200 and the joint itself. The negative-pressure source 105 can continue to evacuate most of the air from the chamber 355 so that the cover 125 is fully collapsed and the tissue interface 120 is compressed.

Figure 7:
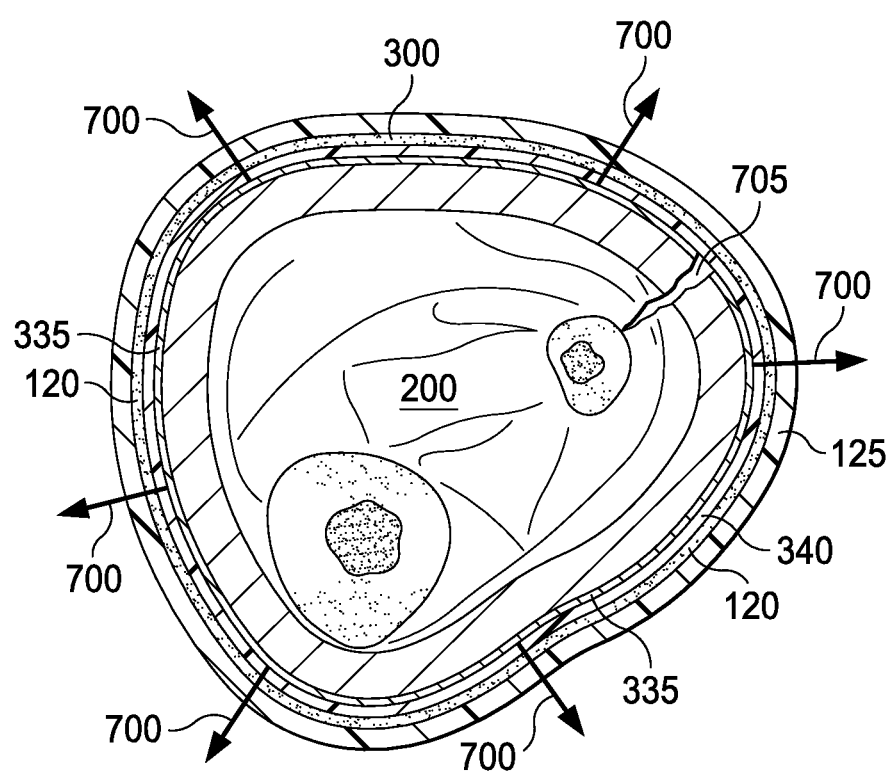
FIG. 7 is a section view of FIG. 3.

FIG. 7 is a section view of FIG. 3 along line 7-7. As illustrated in the example of FIG. 7, after the cover 125 is fully collapsed, the negative pressure begins to pull the intact skin radially outwardly as shown by arrows 700. The flow channels within the tissue interface 120 do not collapse under the negative pressure. Instead, the flow channels of the tissue interface 120 remain open to apply the negative pressure to the epidermis 335. The negative pressure being distributed to the epidermis 335 by the tissue interface 120 can promote perfusion by pneumatically pulling the epidermis 335 toward the cover 125 for a sustained period of time rather than compressing the tissue site 200. An initial collapsing of the cover 125 can provide a certain amount of splinting at the tissue site 200 followed by a sustained decompression cycle within the chamber 355 that can promote perfusion. Increasing the thickness of the cover 125 can also increase the rigidity of the cover 125, which can allow for additional or increased lift to be applied to the epidermis 335 upon negative pressure being supplied to the tissue interface 120. The epidermis 335 may be forced out radially to the inside of the cover 125. In some embodiments, for example, the thickness of the tissue interface 120 may be increased and thickness of the cover 125 may be decreased, which can cause similar radial movement of the epidermis 335. Additionally or alternatively, as shown in the example of FIG. 7, the dressing 110 may also promote healing of a wound or incision 705 at the tissue site 200.

Figure 8:
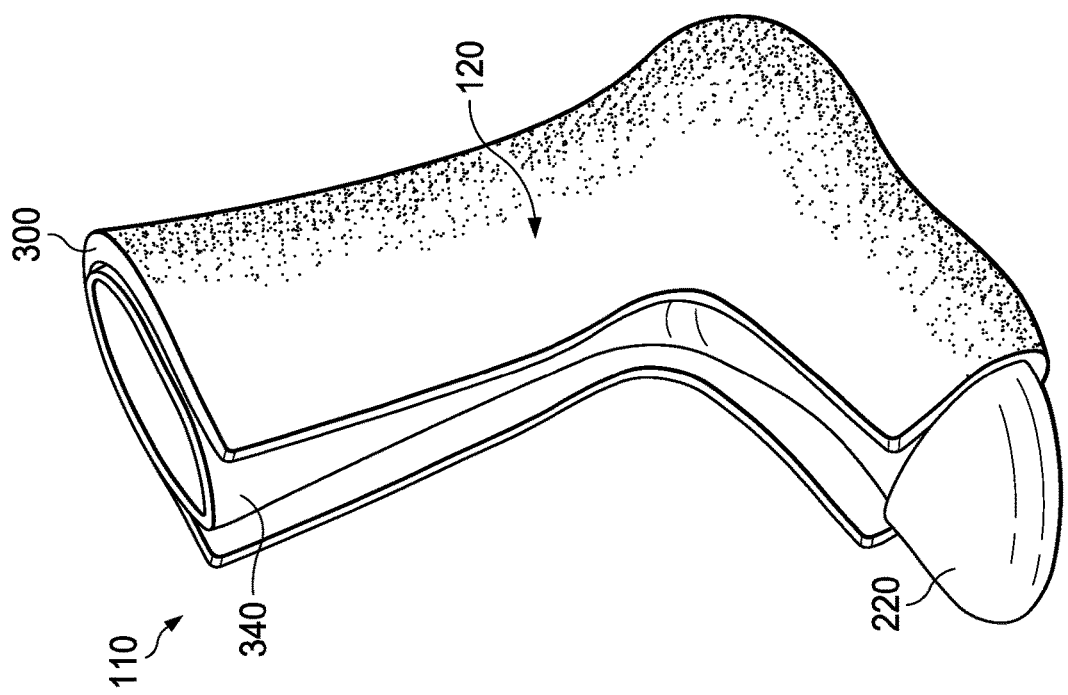
FIG. 8 is an isometric view of various internal components of another example dressing, illustrating additional details that may be associated with some embodiments.

FIG. 8 is an isometric view of various internal components of another example of the dressing 110, illustrating additional details that may be associated with some embodiments. In some embodiments, for example, the toe box 220 may abut the tissue interface 120. In some embodiments, the toe box 220 may include toe separators configured to separate the toes of the patient. Additionally or alternatively, the toe box 220 may possess an antimicrobial property to mitigate the risk of fungal infection and the spread of such infections caused by perspiration and warm temperatures in the toe box 220.

Figure 9:
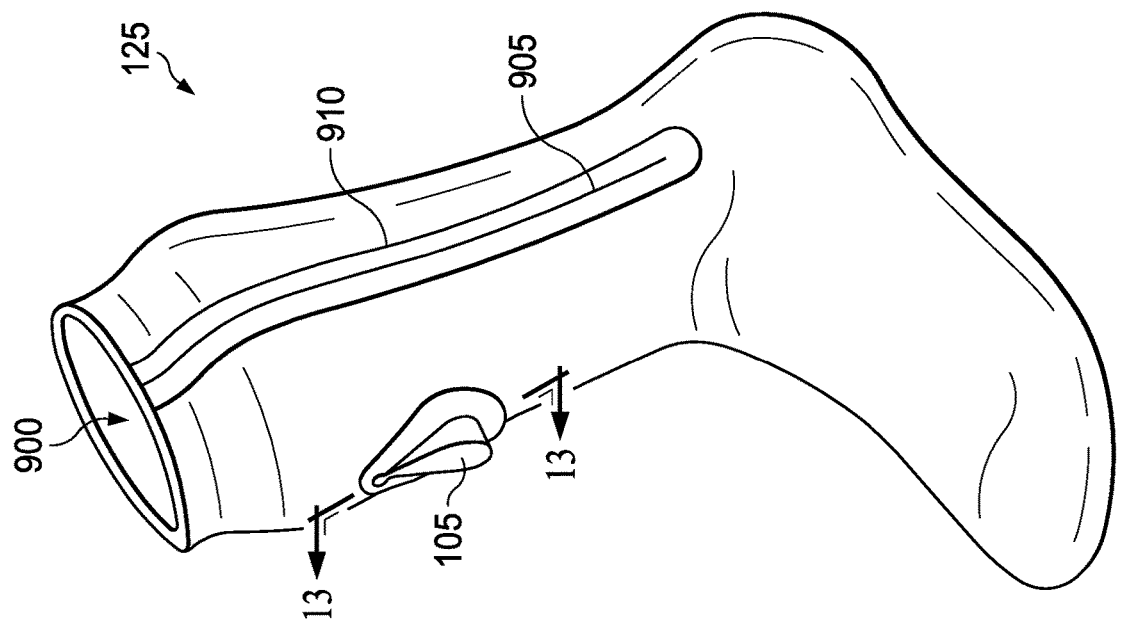
FIG. 9 is an isometric view of another example of a cover that may be associated with some example embodiments of a dressing.

FIG. 9 is an isometric view of another example of the cover 125, illustrating additional details that may be associated with some embodiments of the dressing 110. In some embodiments, the cover 125 may be molded in one-piece from a variety of suitable materials, including but not limited to, silicone, latex, polyurethane, epoxy, neoprene, plastisol, or other synthetic or natural polymer or rubbers. For example, in some embodiments, the cover 125 may be produced via dip molding using a foot-shaped mandrel. The cover 125 of FIG. 9 includes a first end 900 that is open. Following molding of the cover 125, the tissue interface 120 and toe box 220 may be inserted into the cover 125, or the cover 125 may be pulled over and above the toe box 220 and the tissue interface 120. The cover 125 may include at least one seam 905 configured to be sealed by a seam sealing member 910. In the example of FIG. 9, the seam 905 is illustrated as extending generally in a line down a lateral side of the leg 235. In some embodiments, the seam 905 may be non-linear and may be located along other portions of the leg 235 and/or the foot 205. The seam 905 may allow for easier application and removal of the dressing 110. The seam 905 may be opened to apply the cover 125 over the tissue site 200, and once applied, the seam 905 may be closed and sealed.

In some embodiments, the negative-pressure source 105 may comprise or consist essentially of a pump coupled to the cover 125. For example, the negative-pressure source 105 of FIG. 9 is a bellows-type pump, which may be actuated to supply negative pressure to the tissue interface 120.

Figure 10:
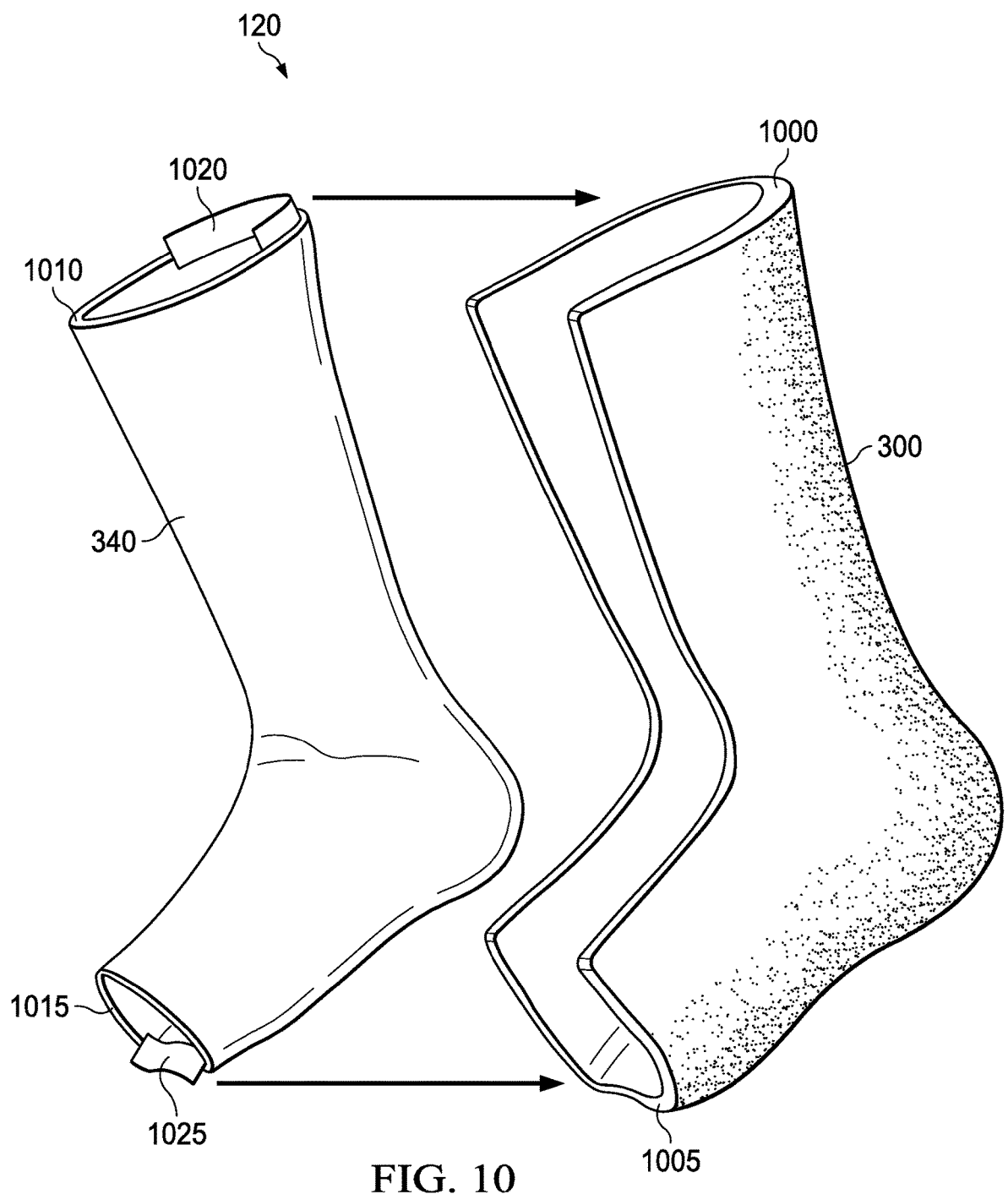
FIG. 10 is an exploded view of another example of a tissue interface, illustrating additional details that may be associated with some embodiments.

FIG. 10 is an exploded view of another example of the tissue interface 120, illustrating additional details that may be associated with some embodiments. In some embodiments, the comfort layer 340 may be coupled to or disposed within the primary manifold 300. For example, in some embodiments, the primary manifold 300 may have a first end 1000 and a second end 1005 and the comfort layer 340 may have a first end 1010 and a second end 1015. The first end 1010 of the comfort layer 340 may be configured to be coupled to the first end 1000 of the primary manifold 300 by a first attachment device, such as for example, a first tape 1020. The second end 1015 of the comfort layer 340 may be configured to be coupled to the second end 1005 of the primary manifold 300 by a second attachment device, such as for example, a second tape 1025. The remainder of the comfort layer 340 may be able to independently move with respect to the primary manifold 300, which may provide enhanced comfort to the patient and may result in reduced pinching or bunching of the comfort layer 340 when the tissue interface 120 is subjected to negative pressure. Although the first tape 1020 and the second tape 1025 are shown as extending only partially around the first end 1010 of the comfort layer 340 and the second end 1015 of the comfort layer 340, respectively, in some embodiments, one or both of the first tape 1020 and the second tape 1025 may extend completely around the first end 1010 of the comfort layer 340 and the second end 1015 of the comfort layer 340, respectively.

Figure 11:
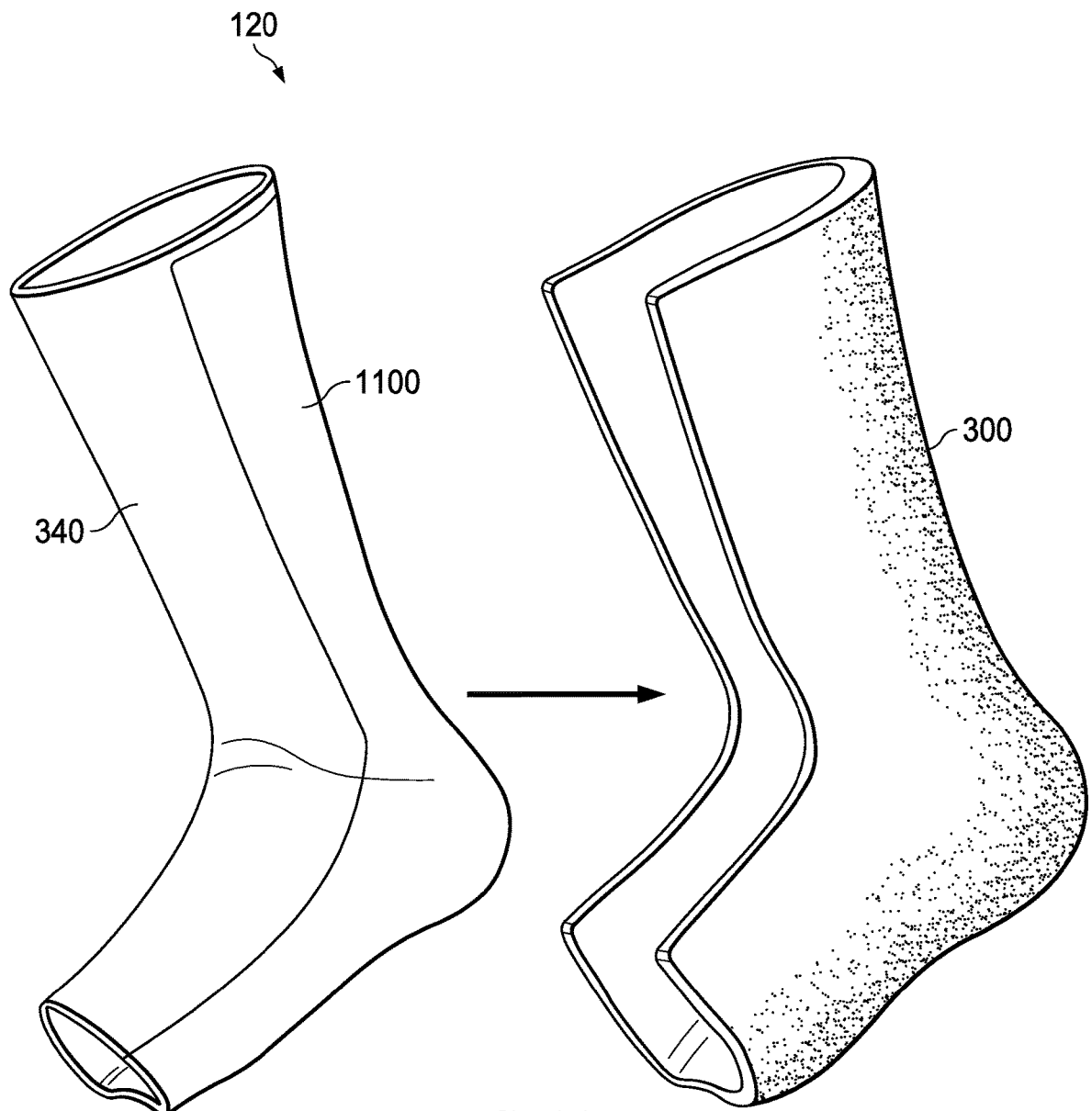
FIG. 11 is an exploded view of another example of a tissue interface, illustrating additional details that may be associated with some embodiments.

FIG. 11 is an exploded view of another example of the tissue interface 120, illustrating additional details that may be associated with some embodiments. In some embodiments, the comfort layer 340 may be coupled along its entire length to primary manifold 300. For example, the tissue interface 120 may be configured to be coupled to the primary manifold 300 by an attachment device, such as for example, an adhesive 1100 applied to a side of the comfort layer 340 configured to face the primary manifold 300. In some embodiments, the adhesive 1100 may be applied to only a portion of the side of the comfort layer 340. In some embodiments, the adhesive 1100 may be applied to the entirety of the side of the comfort layer 340. In some embodiments, the adhesive 1100 may be applied in two or more discontinuous areas of the side of the comfort layer 340. In some embodiments, the adhesive 1100 may be applied to a side of the primary manifold 300 configured to face the comfort layer 340. In some embodiments, the adhesive 1100 may be applied to only a portion of the side of the primary manifold 300. In some embodiments, the adhesive 1100 may be applied to the entirety of the side of the primary manifold 300. In some embodiments, the adhesive 1100 may be applied in two or more discontinuous areas of the side of the primary manifold 300. Coupling the comfort layer 340 to the primary manifold 300 may provide structure to the comfort layer 340.

Figure 12:
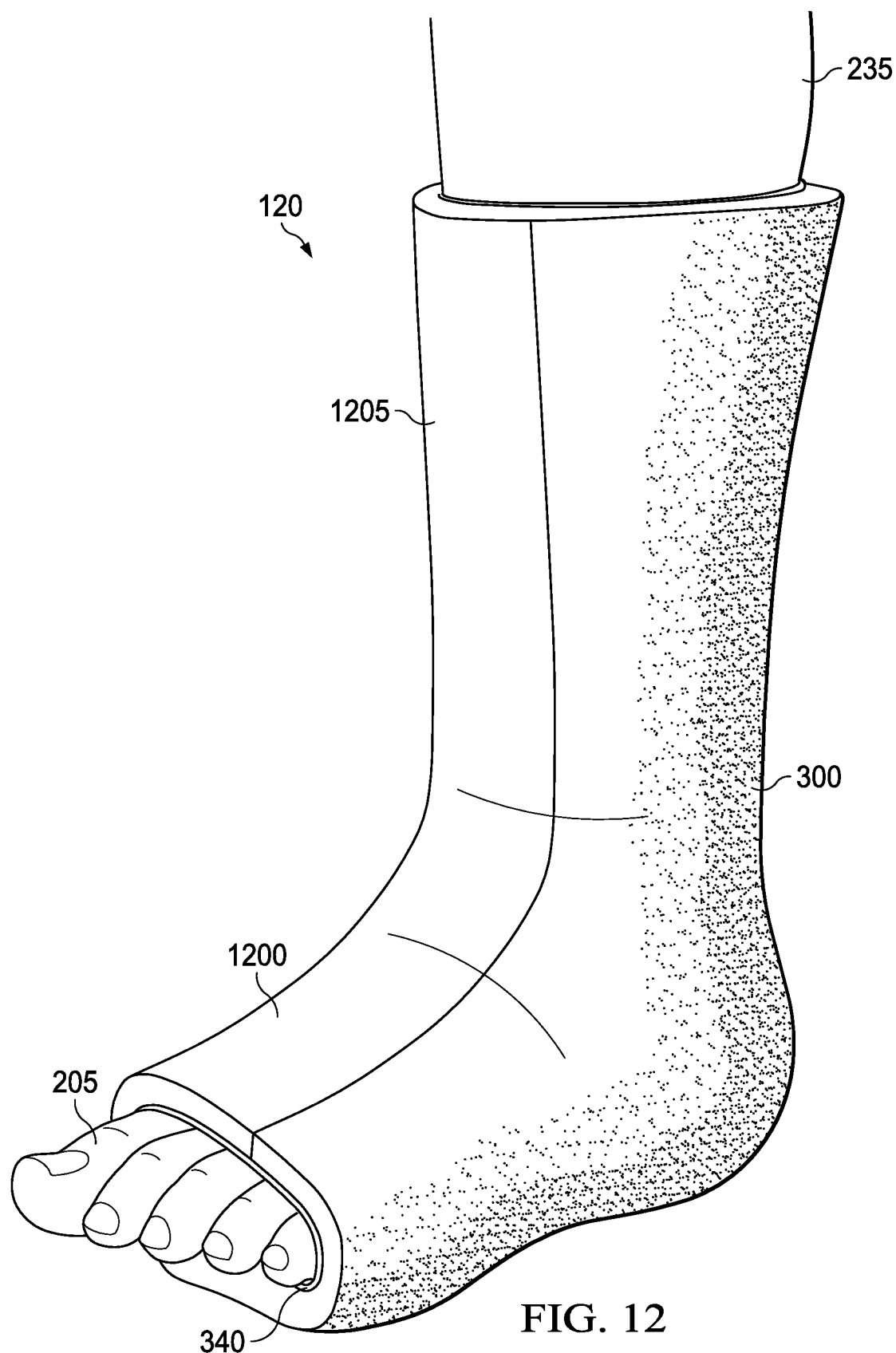
FIG. 12 is an isometric view of the tissue interface of FIG. 8.

FIG. 12 is an isometric view showing the tissue interface 120 of FIG. 8. As shown in FIG. 12, the tissue interface 120 is applied to the tissue site 200, such as, for example, proximate the foot 205 of a patient. The tissue interface 120 may have a first portion 1200 and a second portion 1205. The first portion 1200 may be configured to circumferentially cover at least a portion of the dorsum and the plantar of the foot 205. The second portion 1205 may be configured to circumferentially cover at least a portion of the crus of the patient.

Figure 13:
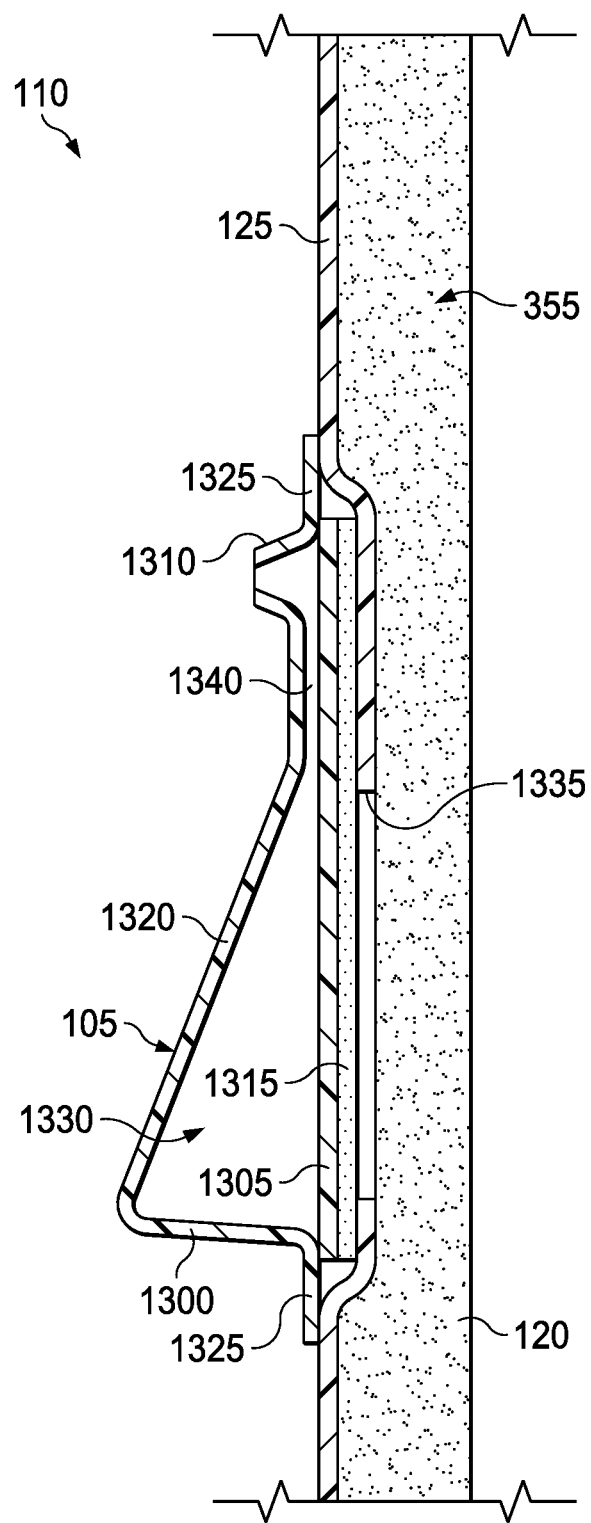
FIG. 13 is detail section view of the dressing of FIG. 9, illustrating additional details that may be associated with some embodiments.

FIG. 13 is a detail section view of the dressing 110 of FIG. 9 along line 9-9, illustrating additional details of the dressing 110 that may be associated with some embodiments. The negative-pressure source 105 may include a chamber assembly 1300, an intake valve 1305, an exhaust valve 1310, and a liquid-air separator 1315. The chamber assembly 1300 may include a chamber wall 1320 and a base 1325 extending outward from the bottom of the chamber wall 1320. The chamber wall 1320 may define a pump chamber 1330. The base 1325 may be releasably or permanently coupled to the cover 125 to seal the pump chamber 1330 to the cover 125. The pump chamber 1330 may be fluidly coupled to the tissue interface 120 through the intake valve 1305, the liquid-air separator 1315, and an aperture 1335 in the cover 125. The chamber assembly 1300 may further include an exhaust duct 1340, which can fluidly couple the exhaust valve 1310 to the pump chamber 1330. The exhaust valve 1310 may only permit one-way fluid flow out of the pump chamber 1330. In some embodiments, for example, the exhaust valve 1310 may be a duckbill valve. The intake valve 1305 may be fluidly coupled with the pump chamber 1330. In some embodiments, the intake valve 1305 may only permit one-way fluid flow into the pump chamber 1330. As shown in FIG. 13, in some embodiments, the intake valve 1305 may be a flat valve. In some embodiments, the intake valve 1305 may be a duckbill valve. As further shown in the example of FIG. 13, in some embodiments the liquid-air separator 1315 may be located between the intake valve 1305 and the cover 125. The liquid-air separator 1315 serves to prevent the liquid from exiting the tissue interface 120 through the aperture 1335 in the cover 125. The liquid-air separator 1315 may allow gas communication, but substantially prevents liquid communication between the tissue interface 120 and the pump chamber 1330.

The negative-pressure source 105 may be actuated by pushing the chamber wall 1320 toward the base 1325, which causes the pump chamber 1330 to be compressed and evacuates fluid out of the pump chamber 1330 through the exhaust valve 1310. Then, when the chamber wall 1320 is no longer being pushed, the chamber wall 1320 moves away from the base 1325. The pump chamber 1330 increases in volume and draws a vacuum, pulling fluid from inside the chamber 355 into the pump chamber 1330 through the aperture 1335 in the cover 125, the liquid-air separator 1315, and the intake valve 1305. The pumping action continues for as long as the negative-pressure source 105 is actuated. In some embodiments, the negative-pressure source 105 may be manually actuated. In some embodiments, the negative-pressure source 105 may be actuated by a powered pump actuator.

Figure 14:
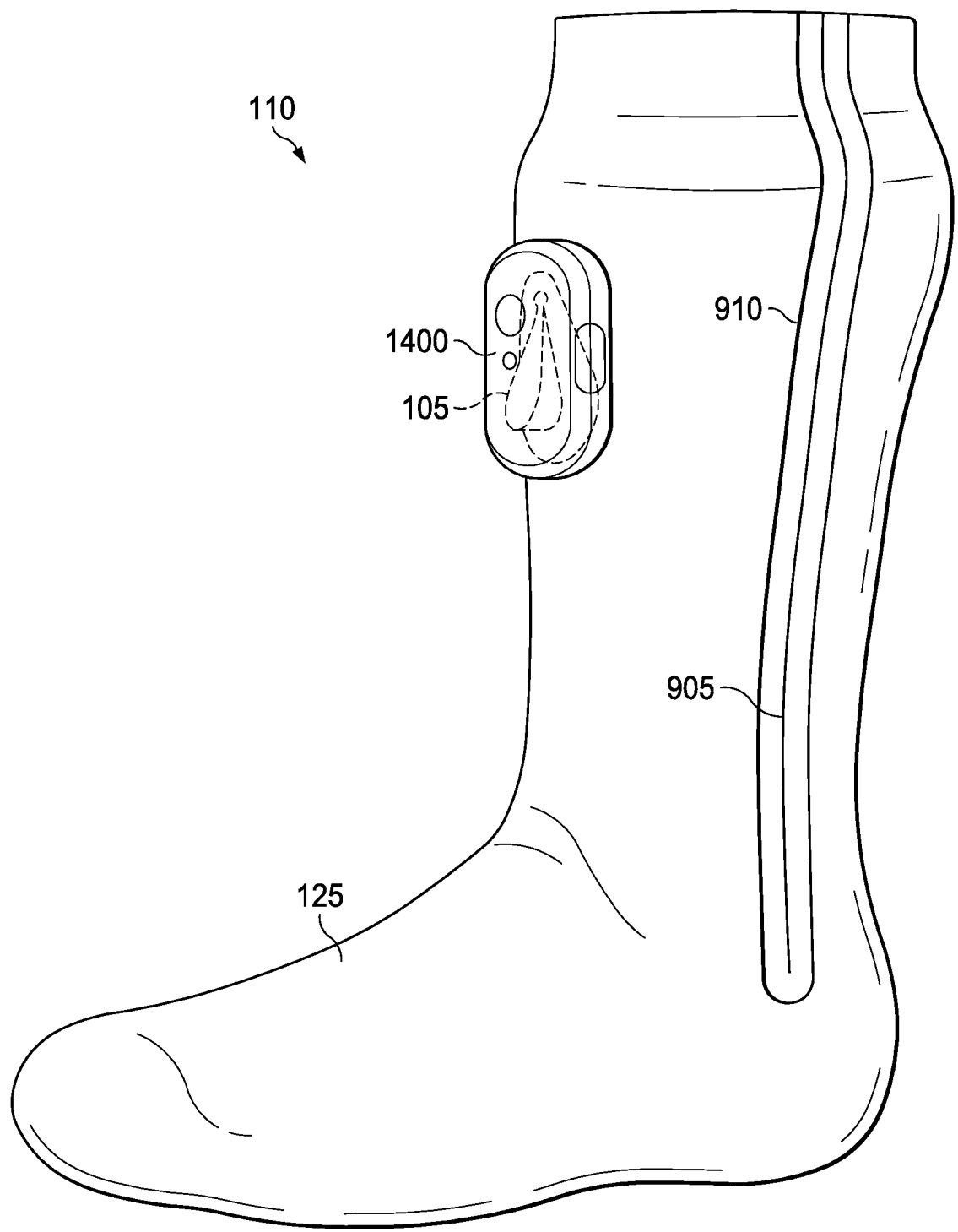
FIG. 14 is an isometric view of the dressing of FIG. 9 with an example of a pump actuator, illustrating additional details that may be associated with some embodiments.

FIG. 14 is an isometric view of the dressing 110 of FIG. 9 with a pump actuator 1400, illustrating additional details that may be associated with some embodiments. As shown in FIG. 14, a pump actuator 1400 may be coupled to the dressing 110. The pump actuator 1400 may include a mechanism to cyclically actuate the negative-pressure source 105. For example, the pump actuator 1400 may include an electric motor that is configured to rotate a cam to cyclically push on the chamber wall 1320 of the negative-pressure source 105. In some embodiments, the pump actuator 1400 may be battery powered.

Figure 15:
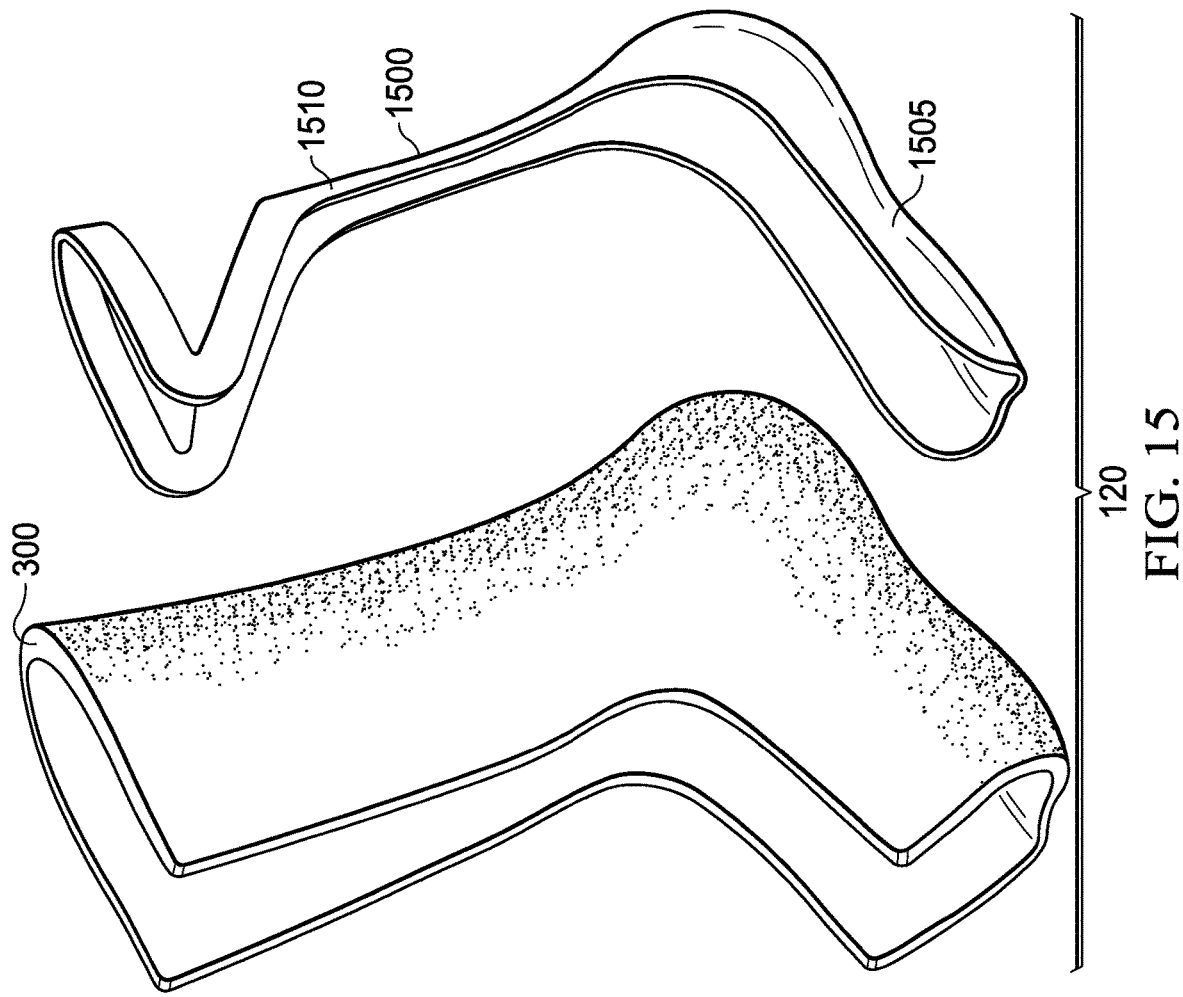
FIG. 15 is an exploded view of an example of a tissue interface, illustrating additional details that may be associated with some embodiments.

FIG. 15 is an exploded view of an example of the tissue interface 120, illustrating additional details that may be associated with some embodiments. In the example embodiment of FIG. 15, the tissue interface 120 may further include a support layer 1500. In some embodiments, the support layer 1500 may include a sole portion 1505 and an upper portion 1510 extending upward from the sole portion 1505. As shown in FIG. 15, in some embodiments, the upper portion 1510 may extend circumferentially around at least a portion of the primary manifold 300. The support layer 1500 may be configured to be located between the primary manifold 300 and the cover 125.

Figure 16:
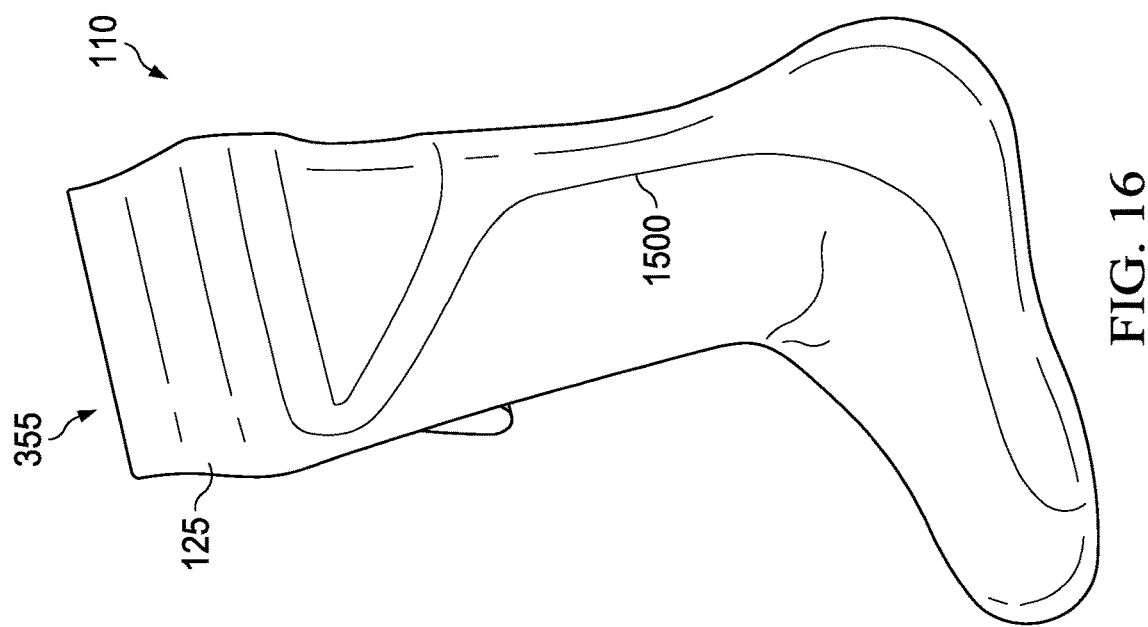
FIG. 16 is a rear isometric view of an example of a dressing including the support layer of FIG. 15, illustrating additional details that may be associated with some embodiments.

FIG. 16 is a rear isometric view of an example of the dressing 110 including the support layer 1500 of FIG. 15, illustrating additional details that may be associated with some embodiments. In the example embodiment of FIG. 16, the dressing 110 is shown under negative pressure. Upon the application of negative pressure, the cover 125 can collapse and be pulled against the support layer 1500. The outline of the support layer 1500 may then be visible through the cover 125. The appearance of the outline of the support layer 1500 through the cover 125 under the application of negative pressure may be useful as an indicia that negative pressure is being applied to the tissue interface 120. Due to the size of the dressing 110, and depending on the operating characteristics of the negative-pressure source 105, it may take some time to substantially or completely evacuate the chamber 355 of fluid. Thus, if the outline of the support layer 1500 cannot be identified through the cover 125 after a certain length of time that negative-pressure has been applied, it may be an indication of a leak in the dressing 110.

Figure 17:
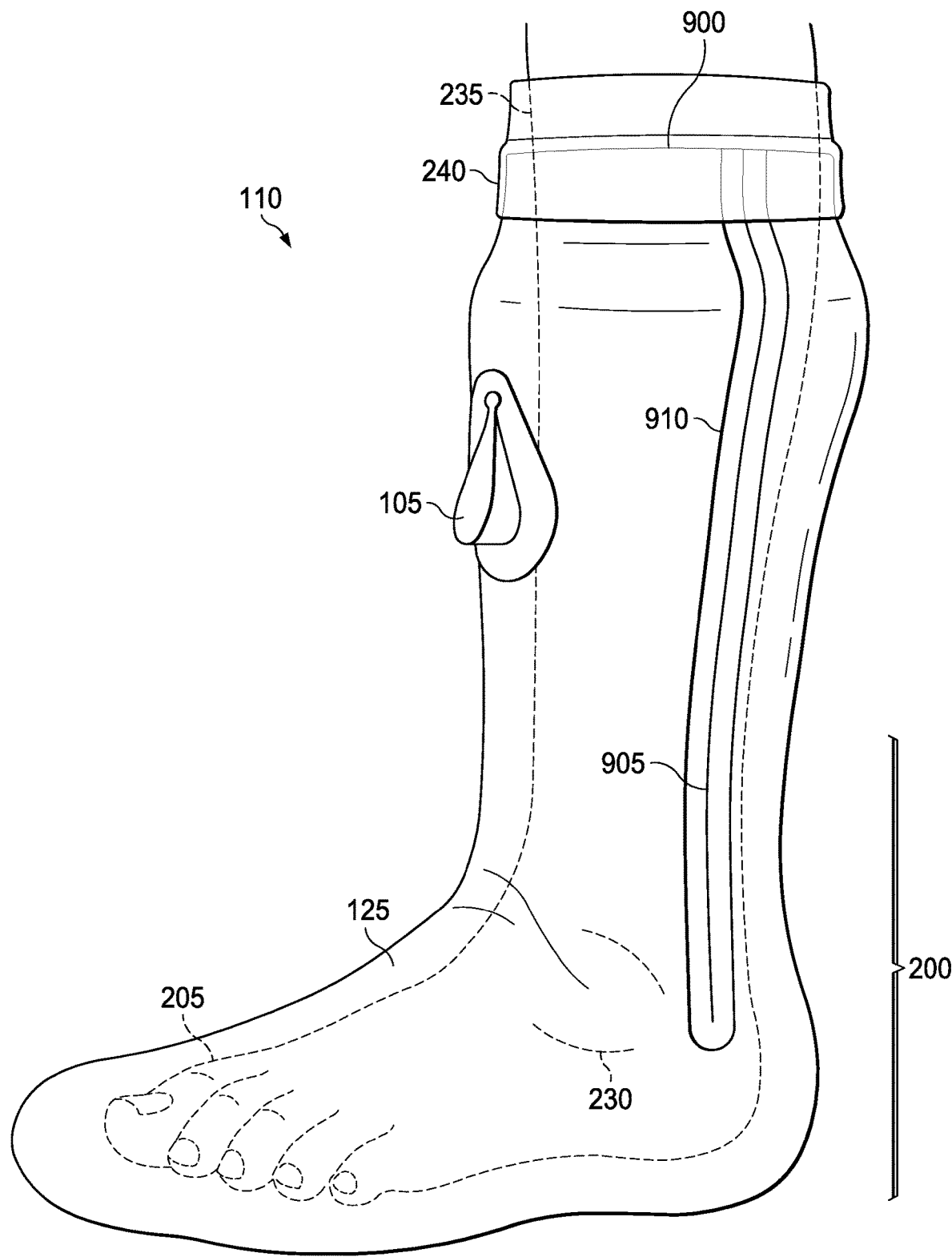
FIG. 17 is an isometric view of another example of a dressing, illustrating additional details that may be associated with some embodiments.

FIG. 17 is an isometric view of an example of the dressing 110, illustrating additional details that may be associated with some embodiments. As illustrated in FIG. 17, the dressing 110 may completely enclose the foot 205, the ankle 230, and a portion of the leg 235 of a patient proximate the tissue site 200. The first end 900 of the cover 125 may be sealed to the leg 235 superior to the ankle 230 by a first sealing member 240.

Figure 18:
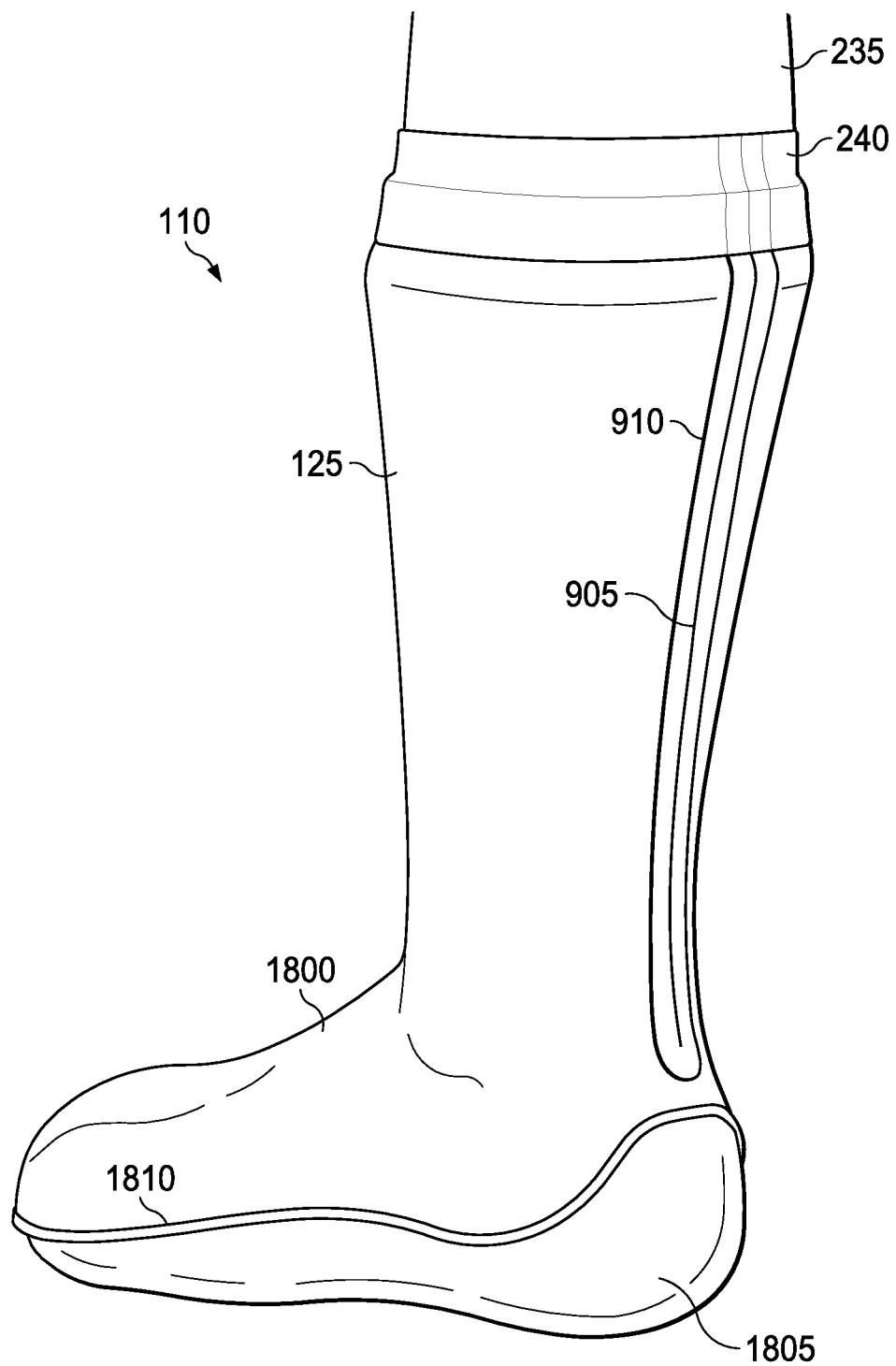
FIG. 18 is a rear isometric view of another example of a dressing, illustrating additional details that may be associated with some embodiments.

FIG. 18 is a rear isometric view of an example of the dressing 110, illustrating additional details that may be associated with some embodiments. In the example embodiment of FIG. 18, the seam 905 of the dressing 110 may extend along the rear of the cover 125 (i.e., the posterior side of the leg 235). Additionally, the cover 125 may be formed from a first cover portion 1800 and a second cover portion 1805. The first cover portion 1800 and the second cover portion 1805 may be coupled to one another at cover seam 1810.

Figure 19:
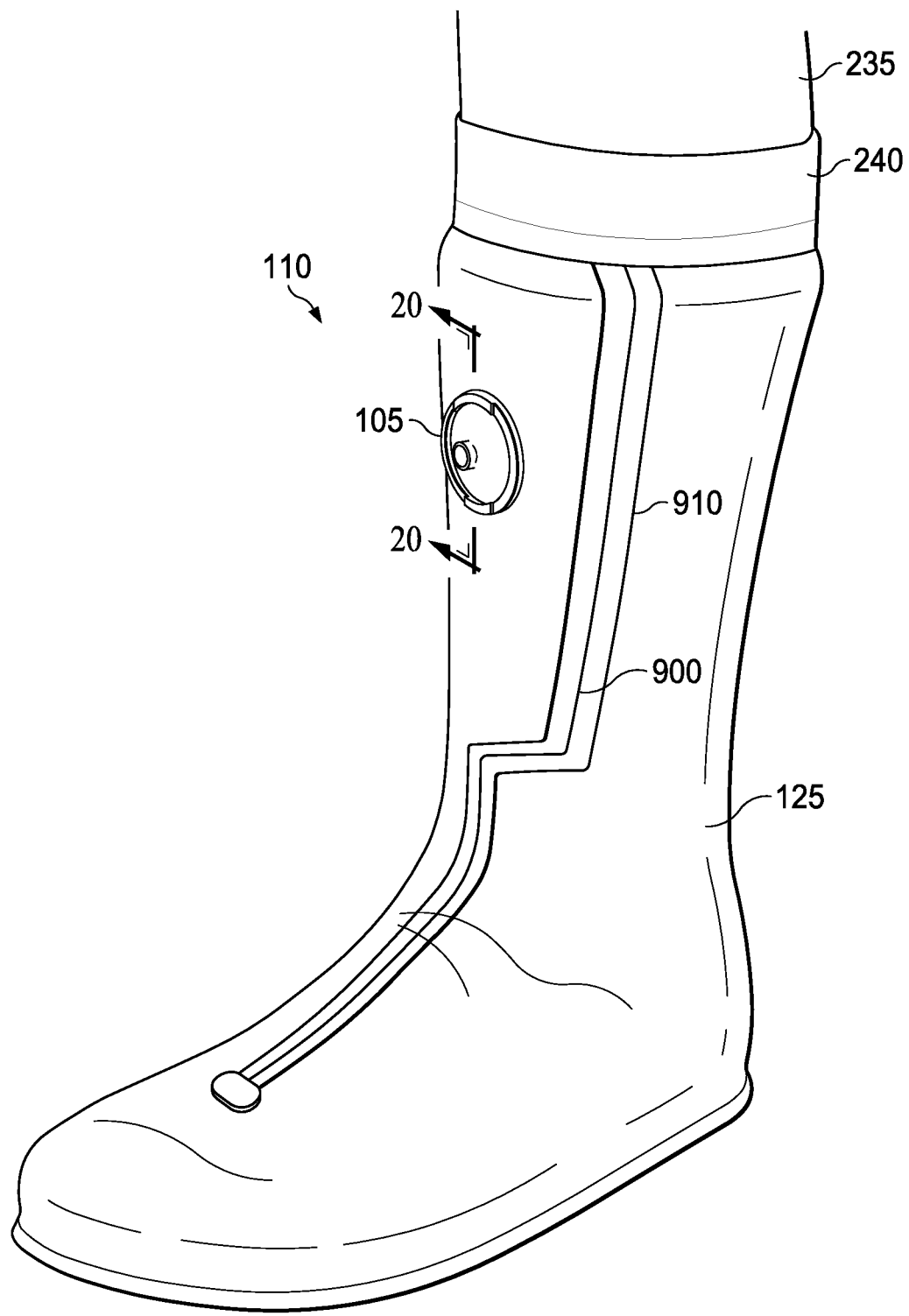
FIG. 19 is an isometric view of another example of a dressing, illustrating additional details that may be associated with some embodiments.

FIG. 19 is an isometric view of an example of the dressing 110, illustrating additional details that may be associated with some embodiments. As shown in FIG. 19, the dressing 110 includes the seam 905 extending generally in a zig-zag line down the anterior side of the leg 235. In some embodiments, the dressing 110 may further include a negative-pressure source 105, wherein the negative-pressure source 105 is a diaphragm-style pump.

Figure 20:
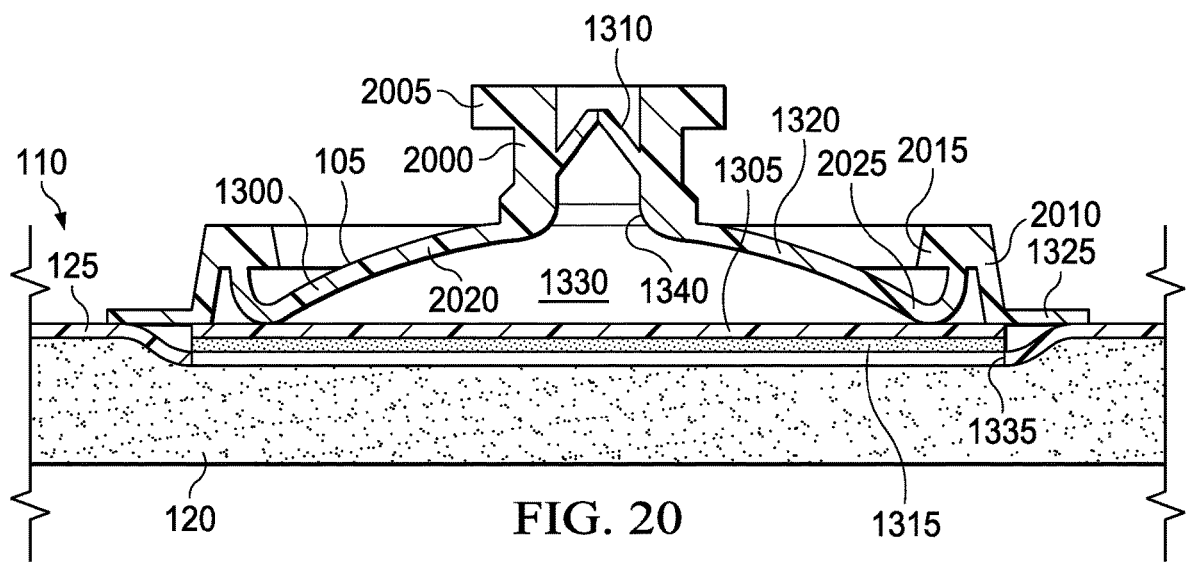
FIG. 20 is a detail section view of the dressing of FIG. 19, illustrating additional details that may be associated with some embodiments.

FIG. 20 is a detail section view of the dressing 110 of FIG. 19 along line 20-20, illustrating additional details that may be associated with some embodiments. The negative-pressure source 105 may include the chamber assembly 1300, the intake valve 1305, and the liquid-air separator 1315. The chamber assembly 1300 may comprise the chamber wall 1320, a boss 2000, an inner attachment lip 2005, a rim 2010, an outer attachment lip 2015, and the base 1325. As shown in FIG. 20, the chamber wall 1320 may be generally hemispherical and includes a first portion 2020, which may have a dome shape, and a second portion 2025, which may have a U-shape, extending around the periphery of the chamber wall 1320. The boss 2000 may be cylindrical and may extend away from the center of the first portion 2020. Extending through the boss 2000 may be the exhaust duct 1340. The exhaust valve 1310 may be located in the exhaust duct 1340. The exhaust valve 1310 may only permit one-way fluid flow out of the pump chamber 1330. In some embodiments, for example, the exhaust valve 1310 may be a duckbill valve. The chamber assembly 1300 further includes the inner attachment lip 2005 that may extend radially outward from the top of the boss 2000. Additionally, the rim 2010 of the chamber assembly 1300 may extend around the periphery of the chamber wall 1320. In some embodiments, the outer attachment lip 2015 may extend radially inward from the top of the rim 2010. As shown in FIG. 20, the second portion 2025 of the chamber wall 1320 may be coupled to the bottom side of the outer attachment lip 2015. The base 1325 may extend radially outward from the bottom of the rim 2010.

Figure 21:
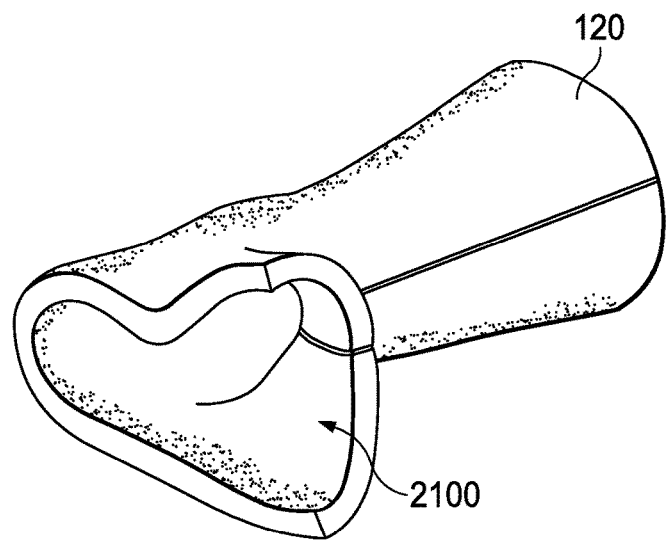
FIG. 21 is an isometric view of another example of a tissue interface, illustrating additional details that may be associated with some embodiments.

FIG. 21 is an isometric view of another example of the tissue interface 120, illustrating additional details that may be associated with some embodiments. As shown in FIG. 21, in some embodiments, the tissue interface 120 may have an open sole 2100. The tissue interface 120 may not cover the sole or plantar of the foot 205 of a patient.

Figure 22:
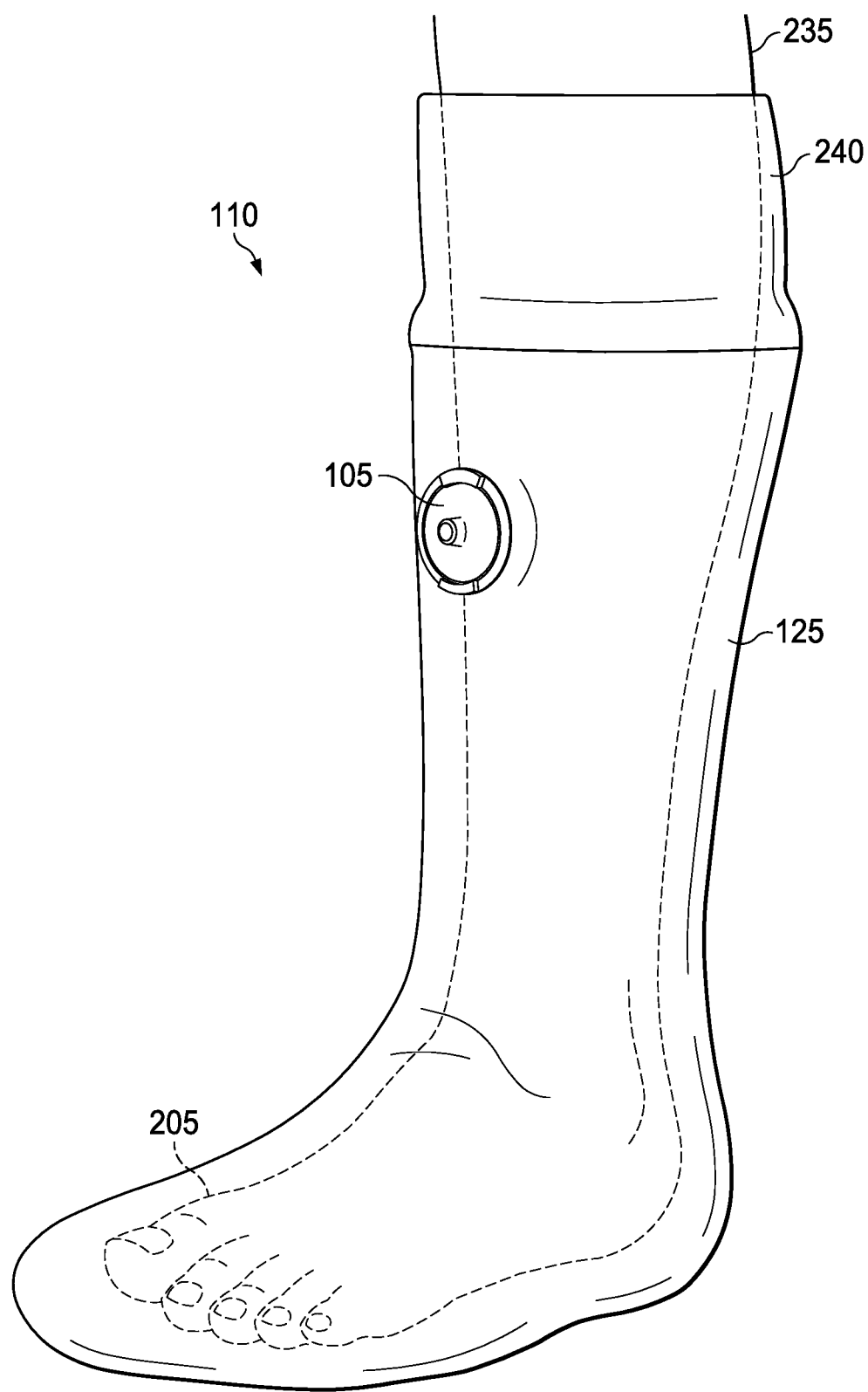
FIG. 22 is an isometric view of another example of a dressing, illustrating additional details that may be associated with some embodiments.

FIG. 22 is a rear isometric view of another example of the dressing 110, illustrating additional details that may be associated with some embodiments. The first sealing member 240 of the dressing 110 may be integrally formed with the cover 125. For example, in embodiments where the cover 125 is formed via a dip molding process, the material used to form the cover 125 may extend a sufficient distance above the tissue interface 110 to form the first sealing member 240. The first sealing member 240 may be an extension of the cover 125. The first sealing member 240 may be sufficiently resilient to permit expansion of the first sealing member 240 so that it may be pulled up the foot 205 to the leg 235, where the first sealing member 240 is able to contract and conform to the shape of the leg 235, creating a fluid seal around the leg 235. In some embodiments, the negative-pressure source 105 may also be integrally formed with the cover 125.

Figure 23:
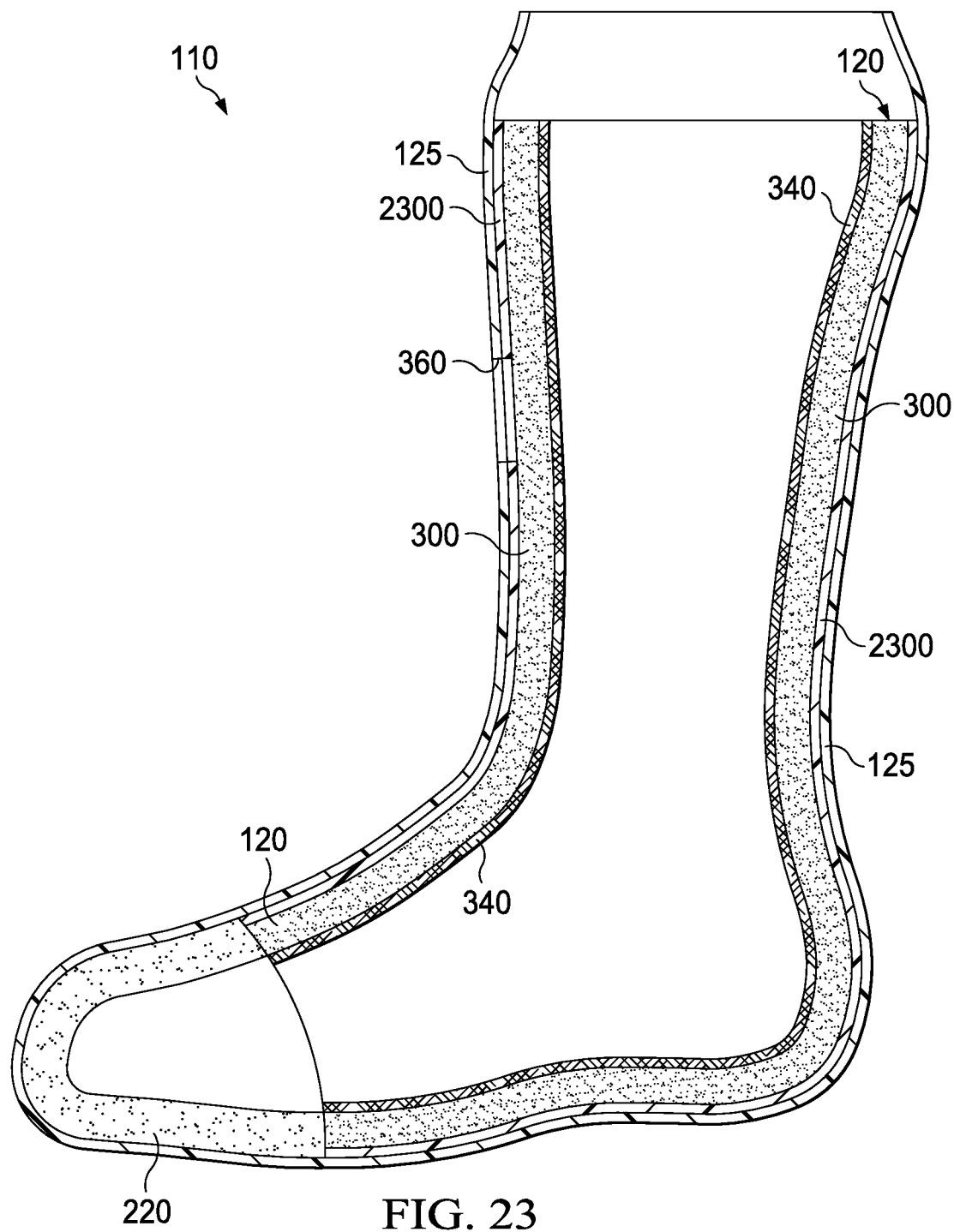
FIG. 23 is a section view of another example of a dressing, illustrating additional details that may be associated with some embodiments.

FIG. 23 is a section view of another example of the dressing 110, illustrating additional details that may be associated with some embodiments. In the example of FIG. 23, the tissue interface 120 includes an intermediate layer 2300. The comfort layer 340 may be located on a first side of the primary manifold 300 and can be configured to contact a tissue site. The intermediate layer 2300 may be located on a second side of the primary manifold 300, opposite the comfort layer 340. The intermediate layer 2300 may cover the outside of the primary manifold 300. The intermediate layer 2300 may comprise a layer of closed-cell foam or other suitable non-porous material. The dressing 110 of FIG. 23 may be constructed by coupling the toe box 220 to the tissue interface 120. The cover 125 may then be formed over the toe box 220 and the tissue interface 120. For example, the toe box 220 and tissue interface 120 may be dipped into a suitable material to form the cover 125 via a dip molding process. The dip molding process may form the cover 125 directly over the toe box 220 and the tissue interface 120. The closed-cell construction of the intermediate layer 2300 and the toe box 220 can prevent the molding material of the cover 125 from entering into open cells of the tissue interface 120 and clogging the tissue interface 120. An aperture 360 may be formed in the cover 125 and the intermediate layer 2300 to create a fluid passageway for negative pressure to be delivered to the primary manifold 300.

Figure 24:
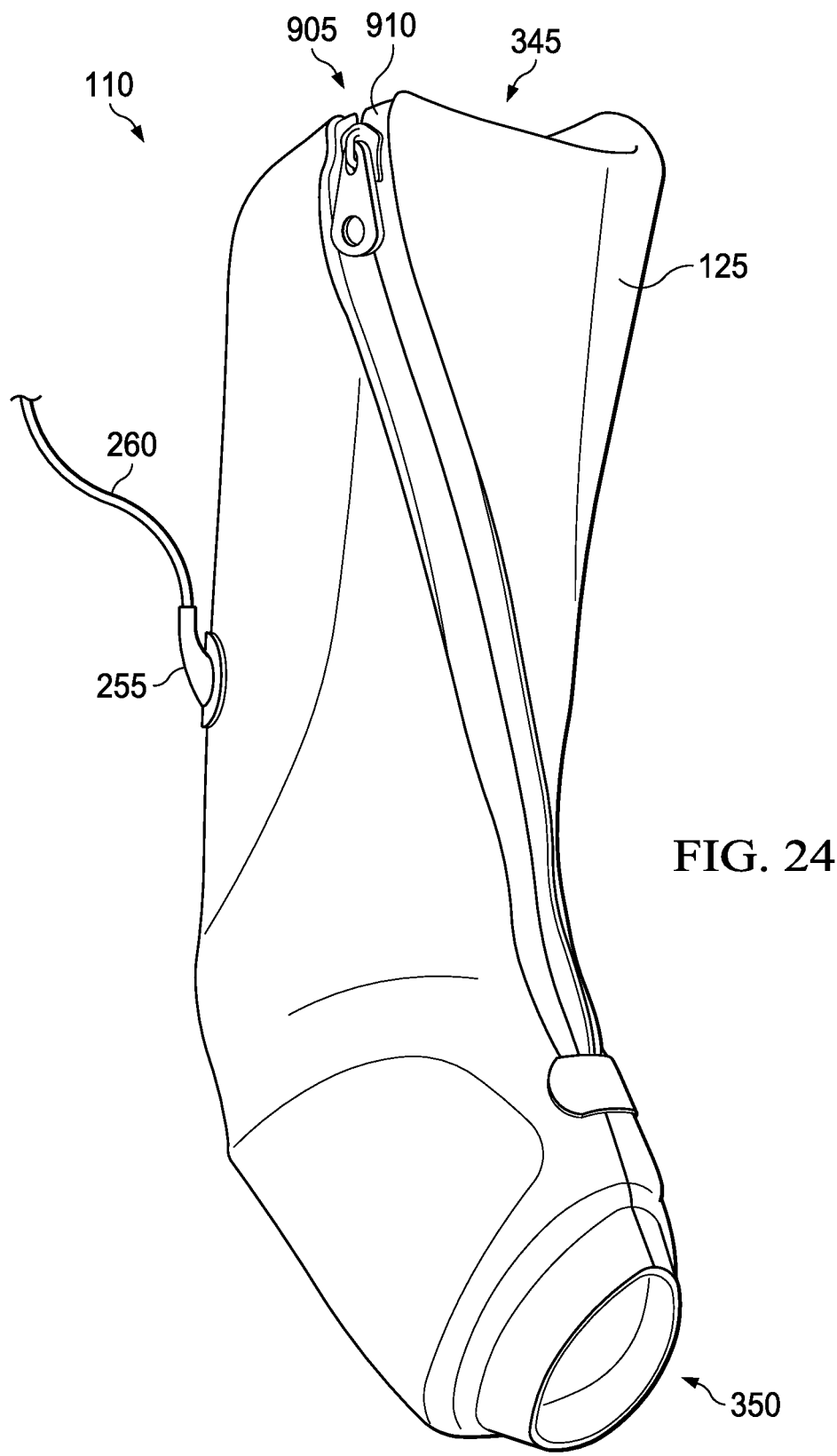
FIG. 24 is an isometric view of another example of a dressing, illustrating additional details that may be associated with some embodiments.

FIG. 24 is an isometric view of another example of the dressing 110, illustrating additional details that may be associated with some embodiments. As illustrated in the example of FIG. 24, the first end 345 and the second end 350 of the cover 125 may be open. When in use, the toes of the patient may extend out of the second end 350 of the cover 125. FIG. 24 further illustrates an example of the cover 125 in which the sealing member 910 comprises or consists of a zipper configured to provide an air-tight seal over the seam 905. A negative pressure may be supplied to the interior of the dressing 110 via the fluid conductor 260 and the dressing interface 255.

Figure 25:
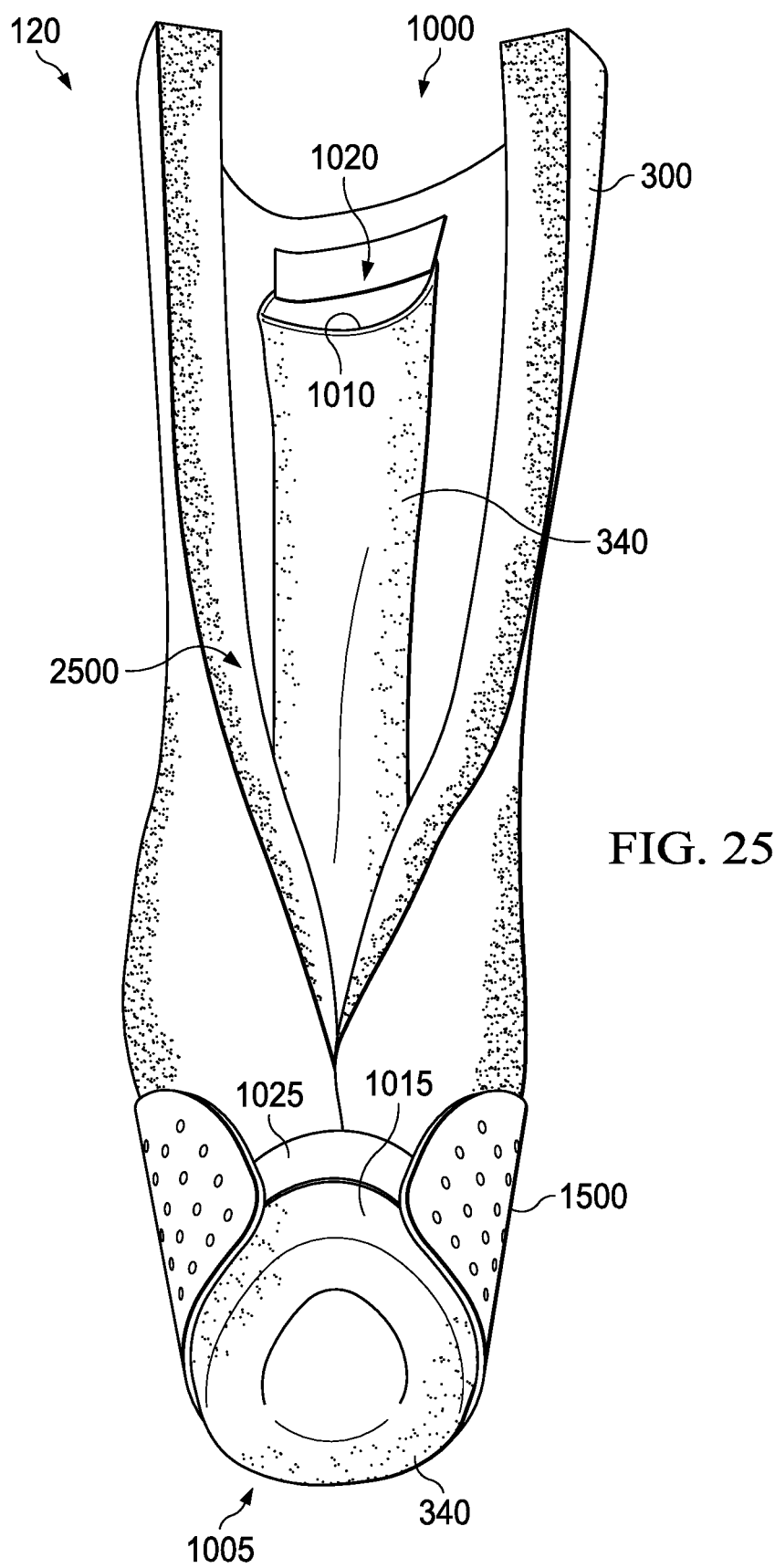
FIG. 25 is a front view of the tissue interface of the dressing of FIG. 24.

FIG. 25 is a front view of an example of the tissue interface 120 of the dressing 110 of FIG. 24. In the example of FIG. 25, the first end 1000 and the second end 1005 are open. The primary manifold 300 may have a seam 2500, which may extend at least partially from the first end 1000 to the second end 1005. The seam 2500 may allow for easier application and removal of the tissue interface 120. As further shown in FIG. 25 the comfort layer 340 may be coupled to the primary manifold 300. For example, in some embodiments, the first end 1010 of the comfort layer 340 may be configured to be coupled to the first end 1000 of the primary manifold 300 by a first attachment device, such as for example, tape 1020. The second end 1015 of the comfort layer 340 may be configured to be coupled to the second end 1005 of the primary manifold 300 by a second attachment device, such as for example, tape 1025. As shown in FIG. 25, in some embodiments, for example, only the back side of the first end 1010 of the comfort layer 340 may be coupled to the primary manifold 300, and the second end 1015 of the comfort layer 340 may be coupled to a side of the primary manifold 300 configured to face the cover 125, proximate the second end 1005 of the primary manifold 300. The support layer 1500 may be coupled to the primary manifold 300 opposite the comfort layer 340. The support layer 1500 may comprise a material that is more rigid than the primary manifold 300. In some embodiments, for example, the support layer 1500 may be formed of a neoprene sheet having a thickness of about 1/16 inch (about 1.5875 mm) and a 50 Shore A hardness. In some embodiments, for example, the support layer 1500 may be formed of a polyurethane foam such as HyPUR-cel™ foam available from Rubberlite Incorporated of Huntington, W. Va.

Figure 26:
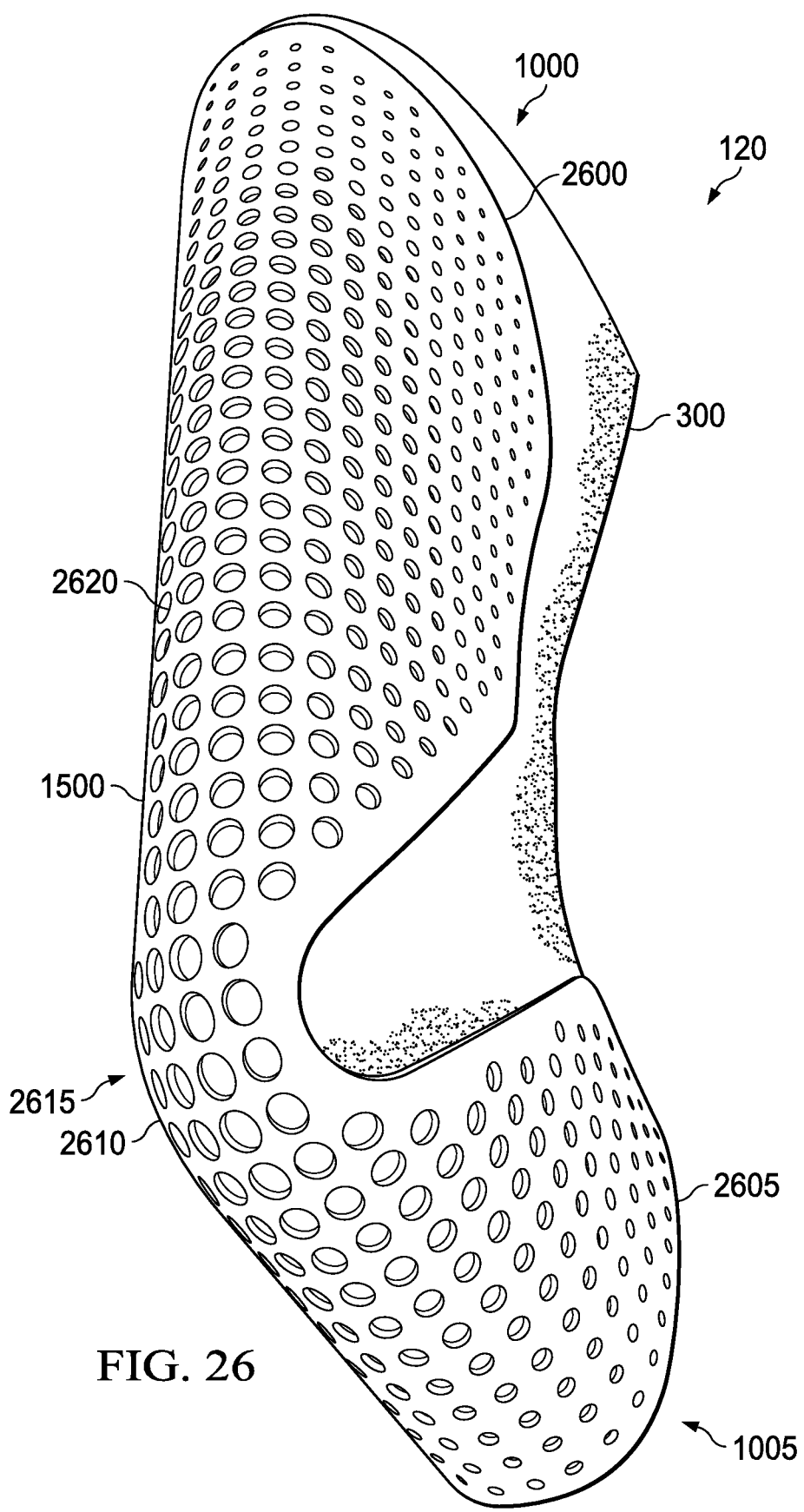
FIG. 26 is an isometric view of the tissue interface of FIG. 25, illustrating the bottom and rear portions of the tissue interface.

FIG. 26 is an isometric view of the tissue interface 120 of FIG. 25, illustrating the bottom and rear portions of the tissue interface 120. The support layer 1500 may include a first wing portion 2600, a second wing portion 2605, and a stem portion 2610 connected to and extending between the first wing portion 2600 and the second wing portion 2605. The first wing portion 2600 may be configured to wrap around the back side of the primary manifold 300 between a heel region 2615 of the primary manifold 300 and the first end 1000 of the primary manifold 300. The stem portion 2610 of the support layer 1500 may be configured to wrap around the back side of the primary manifold 300 proximate the heel region 2615 of the primary manifold 300. The second wing portion 2605 may be may be configured to wrap around the bottom side of the primary manifold 300 between a heel region 2615 of the primary manifold 300 and the second end 1005 of the primary manifold 300. When worn by a patient, the first wing portion 2600 may wrap around at least a portion of the lateral side, the posterior side, and the medial side of the crus of the patient. Additionally, the stem portion 2610 may cover at least a portion of the heel of the patient. The second wing portion 2605 may wrap around at least a portion of the dorsum and the plantar of the foot.

As further shown in FIG. 26, the support layer 1500 may include a plurality of apertures 2620 arrayed in the first wing portion 2600, the second wing portion 2605, and the stem portion 2610. In some embodiments, the open area of each of the apertures 2620 may be equal. In some embodiments, one or more of the apertures 2620 may have an open area having a different size. For example, the open area of apertures proximate the back and bottom side of the primary manifold 300 may be larger than the open area of the apertures proximate the sides of the primary manifold 300. As shown in FIG. 26, in some embodiments, some or all of the plurality of apertures 2620 may be circular. The diameter of the apertures may be the largest in the stem portion 2610 and the diameter of the apertures may decrease toward the first end 1000 of the primary manifold 300 and the second end 1005 of the primary manifold 300. Additionally, the diameter of the apertures may decrease toward the periphery of the first wing portion 2600 and the second wing portion 2605 of the support layer 1500. In some embodiments, the diameter of the apertures in the plurality of apertures may range from about 1 millimeter to about 15 millimeters. The plurality of apertures 2620 may allow for negative pressure to be supplied to the manifold through the support layer 1500. The support layer 1500 may increase the rigidity of the tissue interface 120, which can increase pulling force on the epidermis under negative pressure. The increased pulling force can increase blood and lymphatic flow through the tissue site 200.

Figure 27:
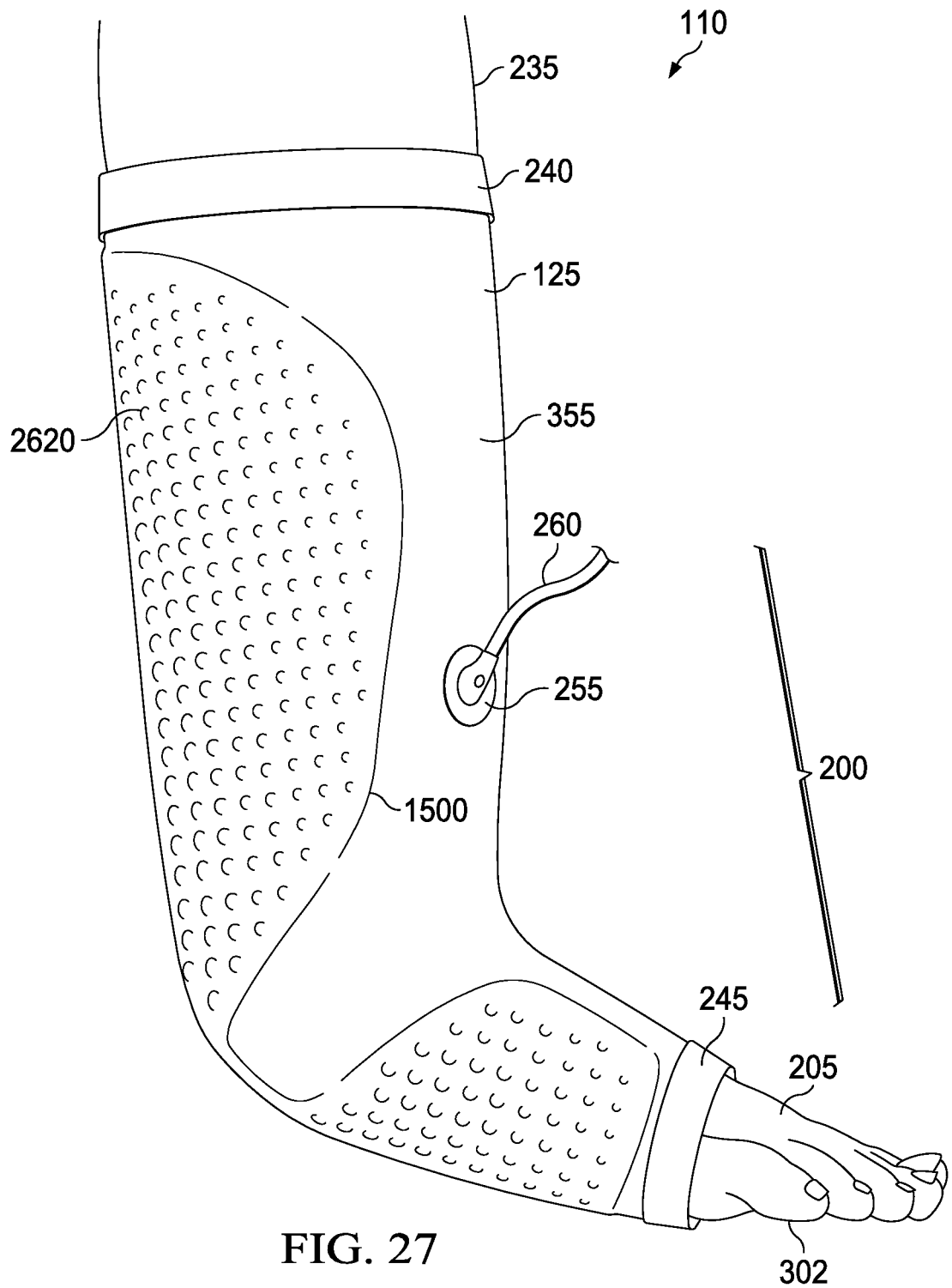
FIG. 27 is a side view of the dressing of FIG. 24.

FIG. 27 is a side view of the dressing 110 of FIG. 24. The dressing 110 may be fluidly sealed to the patient using the first sealing member 240 and the second sealing member 245. In the example embodiment of FIG. 27, the dressing 110 is shown under negative pressure. Upon the application of negative pressure, the cover 125 collapses and is pulled tightly against the support layer 1500. The outline of the support layer 1500 and at least a portion of the plurality of apertures 2620 may then be visible through the cover 125. The appearance of the outline of the support layer 1500 and the plurality of apertures 2620 through the cover 125 under the application of negative pressure may be useful as an indicia that negative pressure is being applied to the tissue interface 120. Due to the size of the dressing 110, and depending on the operating characteristics of the negative-pressure source 105, it may take some time to substantially or completely evacuate the chamber 355 of fluid. If the outline of the support layer 1500 and the plurality of apertures 2620 cannot be identified through the cover 125 after a certain length of time that negative-pressure has been applied, it may be an indication of a leak in the dressing 110. As shown in FIG. 27, in some embodiments, the dressing 110 may not cover the toes 302.

Figure 28:
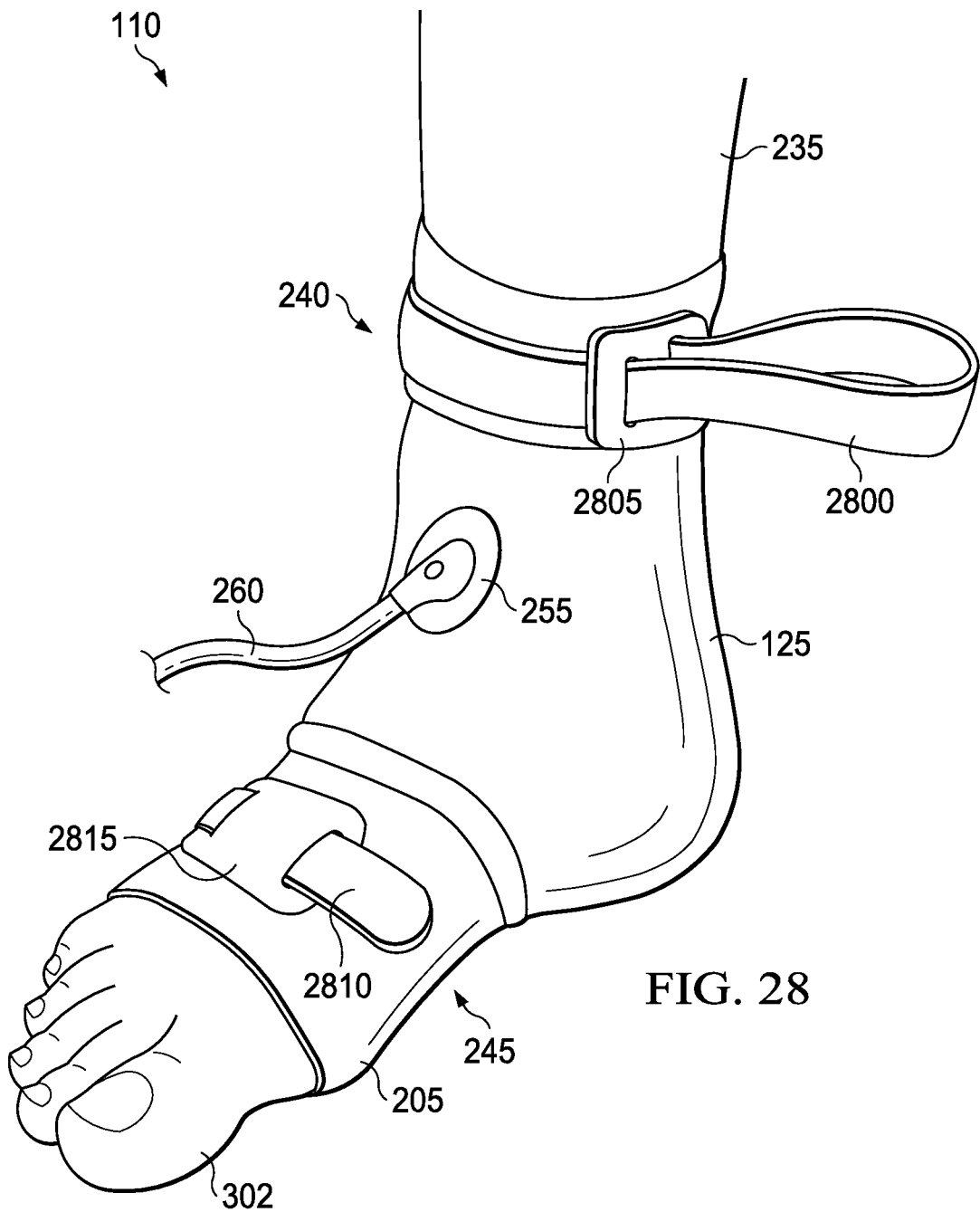
FIG. 28 is an isometric view of another example of a dressing, illustrating additional details that may be associated with some embodiments.

FIG. 28 is an isometric view of another example of the dressing 110, illustrating additional details that may be associated with some embodiments. The dressing 110 may include the first sealing member 240 and the second sealing member 245. As shown in FIG. 28, in some embodiments, the first sealing member 240 may include a first strap 2800 and a first strap retention member 2805, and the second sealing member 245 may include a second strap 2810 and a second strap retention member 2815. The first strap 2800 may extend around the leg 235 and may be pulled tight until a seal is formed around the leg 235. The first strap retention member 2805 may hold the first strap 2800 tight around the leg 235 so that the first strap 2800 does not come loose. The second strap 2810 may extend around the sole and the dorsum of the foot 205 and may be pulled tight until a seal is formed around the sole and the dorsum of the foot 205. The second strap retention member 2815 may hold the second strap 2810 tight around the sole and the dorsum of the foot 205 so that the second strap 2810 does not come loose. As shown in FIG. 28, in some embodiments, the dressing 110 may not cover the toes 302.

Figure 29:
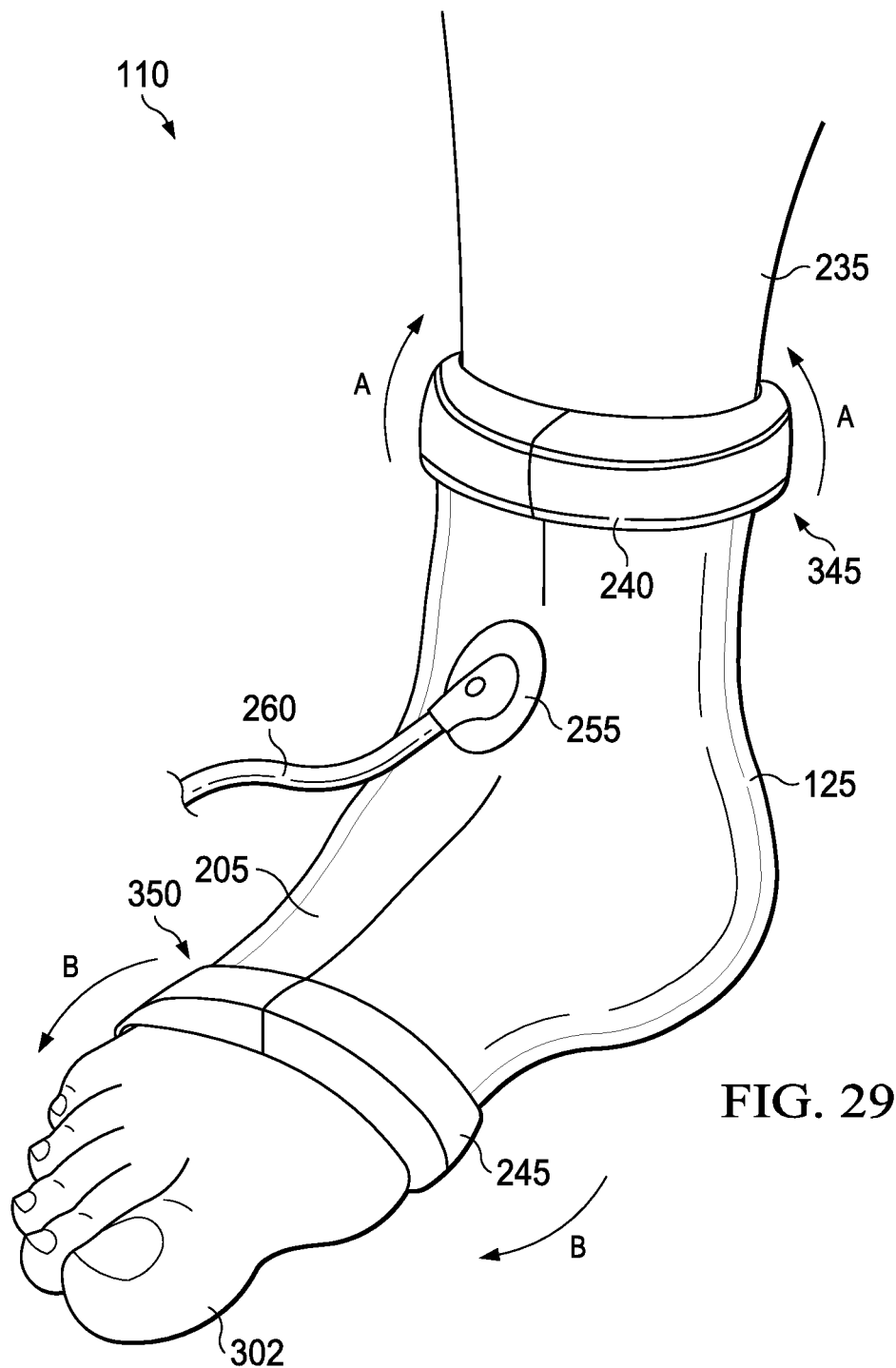
FIG. 29 is an isometric view of another example of a dressing, illustrating additional details that may be associated with some embodiments.

FIG. 29 is an isometric view of another example of the dressing 110, illustrating additional details that may be associated with some embodiments. The dressing 110 may include the first sealing member 240 and the second sealing member 245. As shown in FIG. 29, in some embodiments, the first sealing member 240 and the second sealing member 245 may be configured to flip up and down, respectively, to seal the dressing 110 to the leg 235 and foot 205, respectively. For example, the first sealing member 240 may be coupled to the first end 345 of the cover 125 and may be configured to be in a first downward position when the dressing 110 is applied to the patient. Once the dressing 110 is in the desired location, the first sealing member 240 may be flipped upward (as shown by arrows A) into a second upward position to seal the dressing 110 to the leg 235. Additionally, the second sealing member 245 may be coupled to the second end 350 of the cover 125 and may be configured to be in a first upward position when the dressing 110 is applied to the patient. Once the dressing 110 is in the desired location, the second sealing member 245 may be flipped downward (as shown by arrows B) into a second downward position to seal the dressing 110 to the foot 205.

Figure 30:
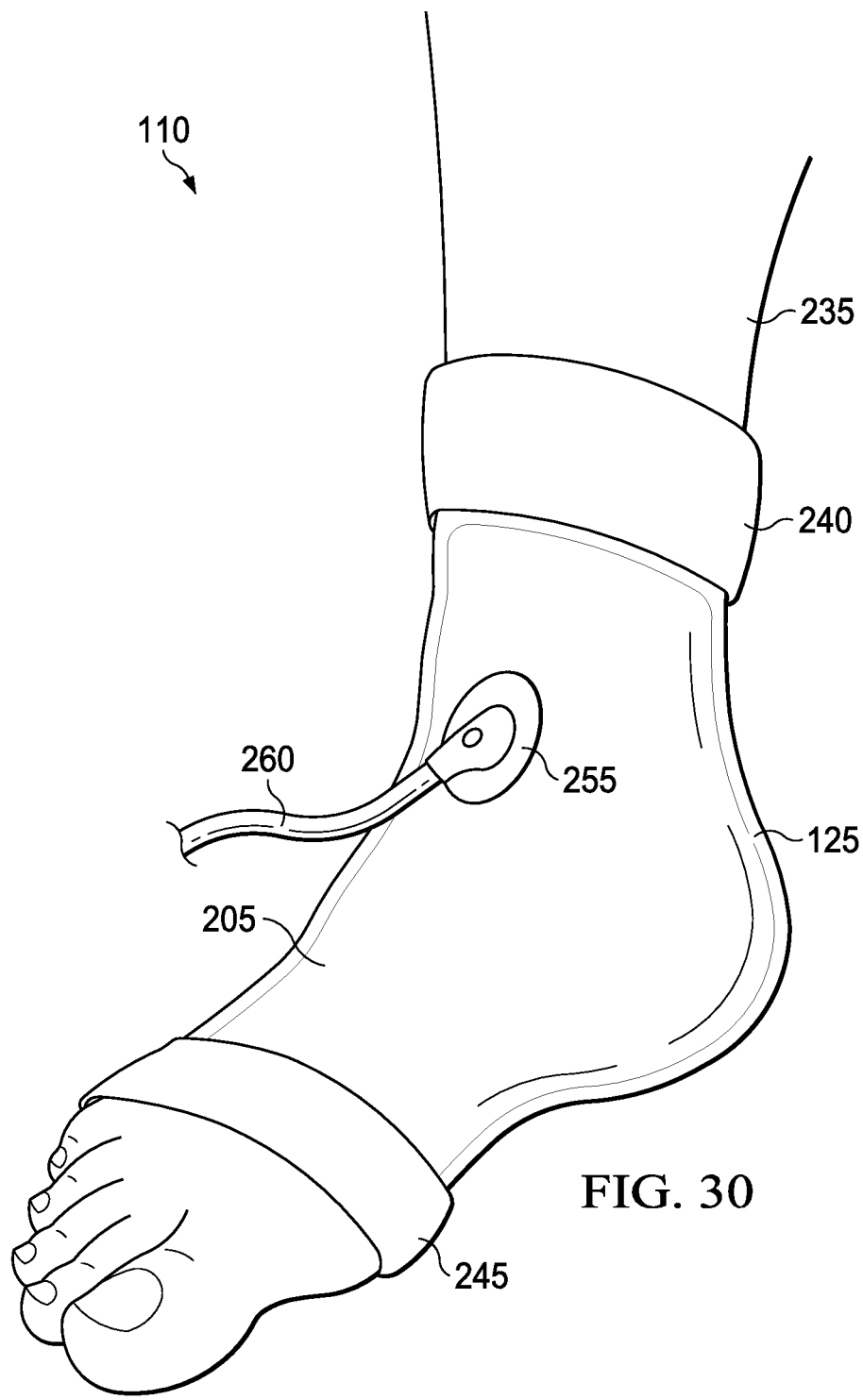
FIG. 30 is an isometric view of the dressing of FIG. 29.

FIG. 30 is an isometric view of the dressing 110 of FIG. 29. As shown in FIG. 30, the first sealing member 240 is flipped upward and the second sealing member 245 is flipped downward to seal the dressing 110 to the foot 205.

Figure 31:
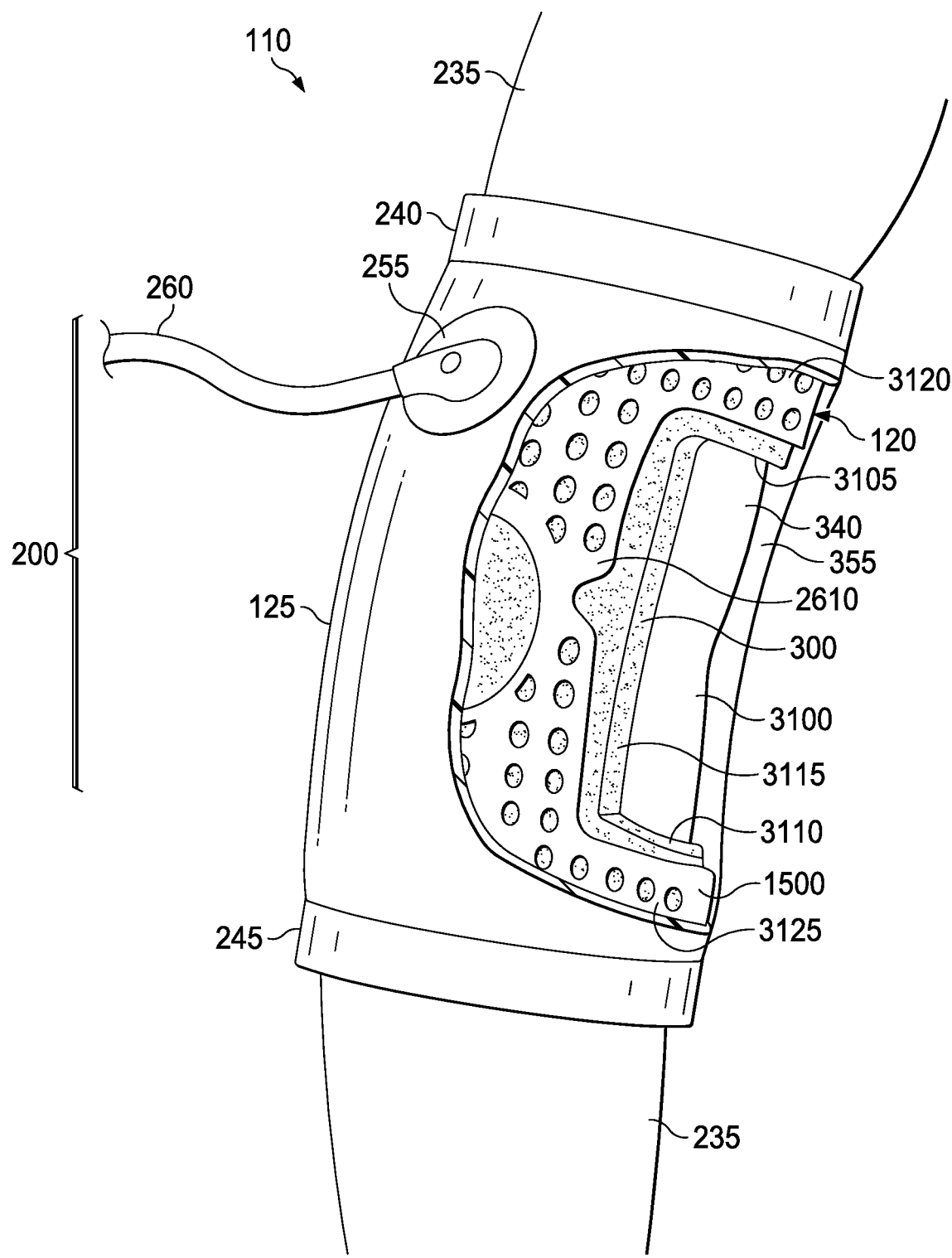
FIG. 31 is a cutaway isometric view of another example of a dressing, illustrating additional details that may be associated with some embodiments.

FIG. 31 is a cutaway isometric view of another example of the dressing 110, illustrating additional details that may be associated with some embodiments. In the example embodiment of FIG. 31, the dressing 110 is configured for delivering a negative pressure to a tissue site 200, such as, for example, proximate a knee 3100 of a patient. The tissue interface 120 of FIG. 31 may be configured to be disposed at least partially around the tissue site 200. The primary manifold 300 may include a first cuff 3105, a second cuff 3110, and a stem 3115 connected to and extending between the first cuff 3105 and the second cuff 3110. The support layer 1500 may include a first cuff 3120, a second cuff 3125, and a stem 2610 connected to and extending between the first cuff 3120 and the second cuff 3125. The cover 125 may be configured to cover the tissue interface 120. The cover 125 may be sealed to the leg 235 superior to the knee 3100 by a first sealing member 240 and to the leg 235 below the knee 3100 by a second sealing member 245. The dressing 110 may further include a dressing interface 255 fluidly coupling the tissue interface 120 to the negative-pressure source 105 via fluid conductor 260 to deliver negative pressure to the tissue site 200. The cover 125 forms the chamber 355 containing the tissue interface 120 and seals the tissue interface 120 within the chamber 355.

Figure 32:
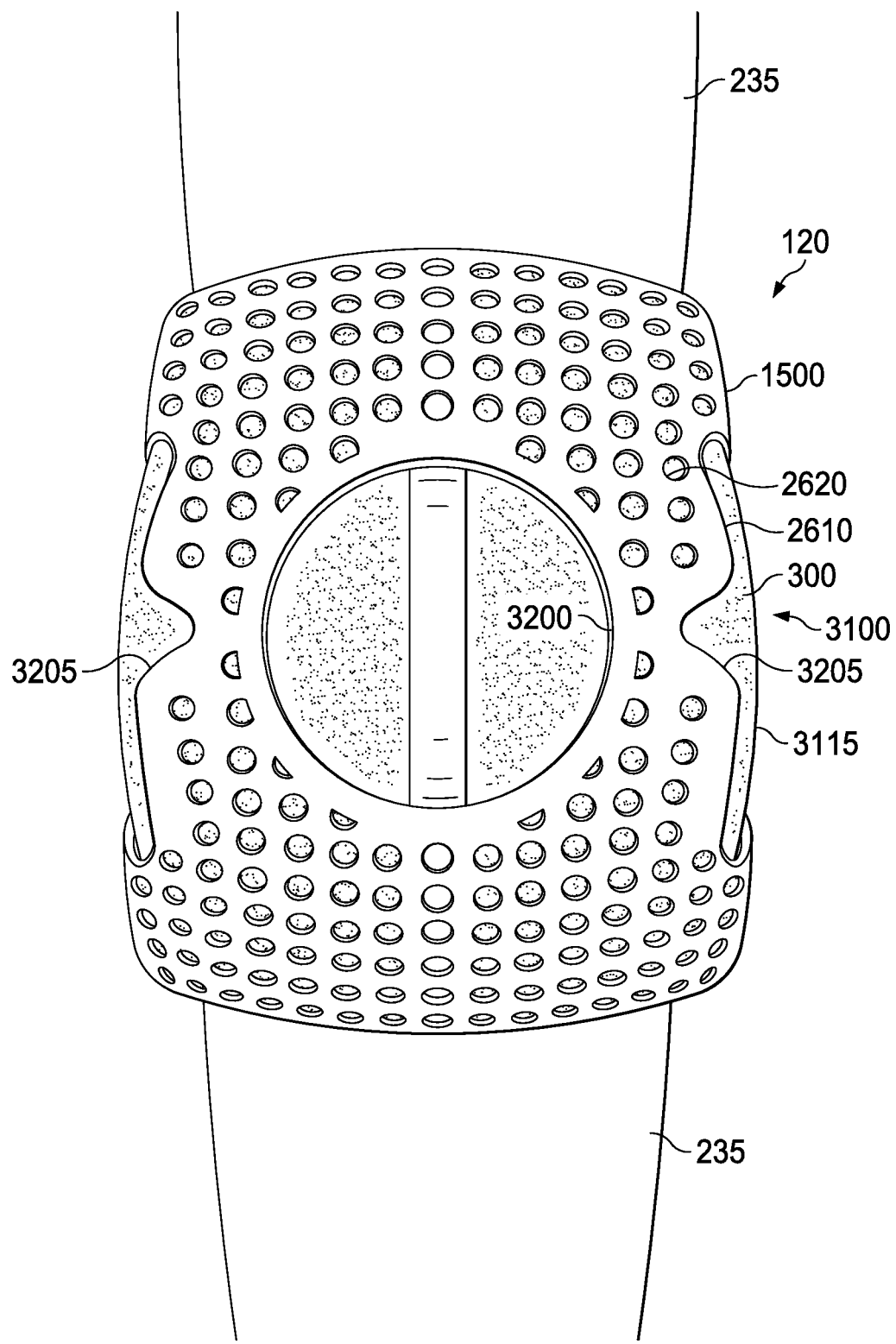
FIG. 32 is a front view of the tissue interface of the dressing of FIG. 31.

FIG. 32 is a front view of the tissue interface 120 of the dressing 110 of FIG. 31. The stem 3115 of the primary manifold 300 is configured to cover at least a portion of the front of the knee 3100. In some embodiments, as shown for example in FIG. 32, the primary manifold 300 may extend from the medial side of the knee 3100, over the patella side of the knee 3100, and to the lateral side of the knee 3100. The support layer 1500 may be coupled to the primary manifold 300 opposite the knee 3100. The support layer 1500 may comprise a material that is more rigid than the primary manifold 300. In some embodiments, for example, the support layer 1500 may be formed of a neoprene sheet having a thickness of about ⅟₁₆ inch (about 1.5875 mm) and a 50 Shore A hardness. In some embodiments, the support layer 1500 may be a single piece of material and may have a shape similar to that of the primary manifold 300. As shown in FIG. 32, the stem 2610 of the comfort layer 340 may be similar in shape to the stem 3115 of the primary manifold 300. Additionally, the support layer 1500 may include a plurality of apertures 2620 arrayed in the stem portion 2610. The support layer 1500 may further include a major aperture 3200 located in the stem 2610. The major aperture 3200 may be located and sized to surround the patella of the knee 3100 when worn by the patient. In some embodiments, the support layer 1500 may additionally include one or more relief cuts 3205 in one or more locations which may reduce or eliminate buckling of the support layer 1500 when the knee 3100 bends. As shown in FIG. 32 a relief cut 3205 may be located on either side of the stem portion 2610 proximate the major aperture 3200.

Figure 33:
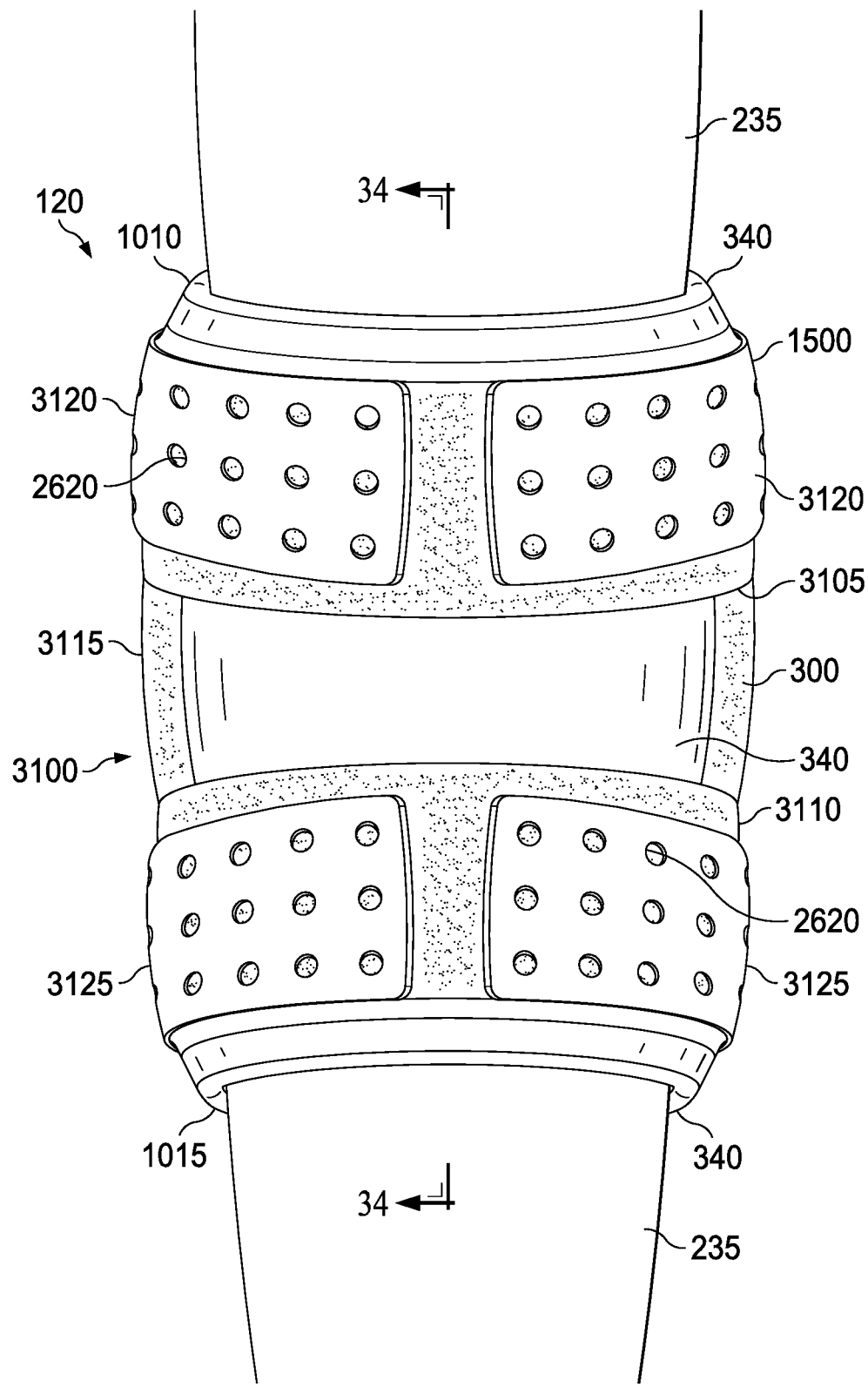
FIG. 33 is a rear view of the tissue interface of FIG. 32.

FIG. 33 is a rear view of the tissue interface 120 of FIG. 32. As shown in FIG. 33, the first cuff 3105 of the primary manifold 300 is configured to extend around the back of the leg 235 above the knee 3100 and the second cuff 3110 of the primary manifold 300 is configured to extend around the back of the leg 235 below the knee 3100. Additionally, in some embodiments, the stem 3115 does not extend around the back of the knee 3100, leaving the popliteal fossa region of the knee 3100 uncovered by the primary manifold 300. As further shown in FIG. 33, the first cuff 3120 of the support layer 1500 may extend around the back of the leg 235 above the knee 3100. The second cuff 3125 of the support layer 1500 may also extend around the back of the leg 235 below the knee 3100. As further shown in FIG. 33, in some embodiments, the some of the plurality of apertures 2620 in the support layer 1500 may be located in the first cuff 3120 and the second cuff 3125 behind the leg 235. A first end 1010 of the comfort layer 340 may be coupled to the first cuff 3105 and a second end 1015 of the comfort layer 340 may be coupled to the second cuff 3110.

Figure 34:
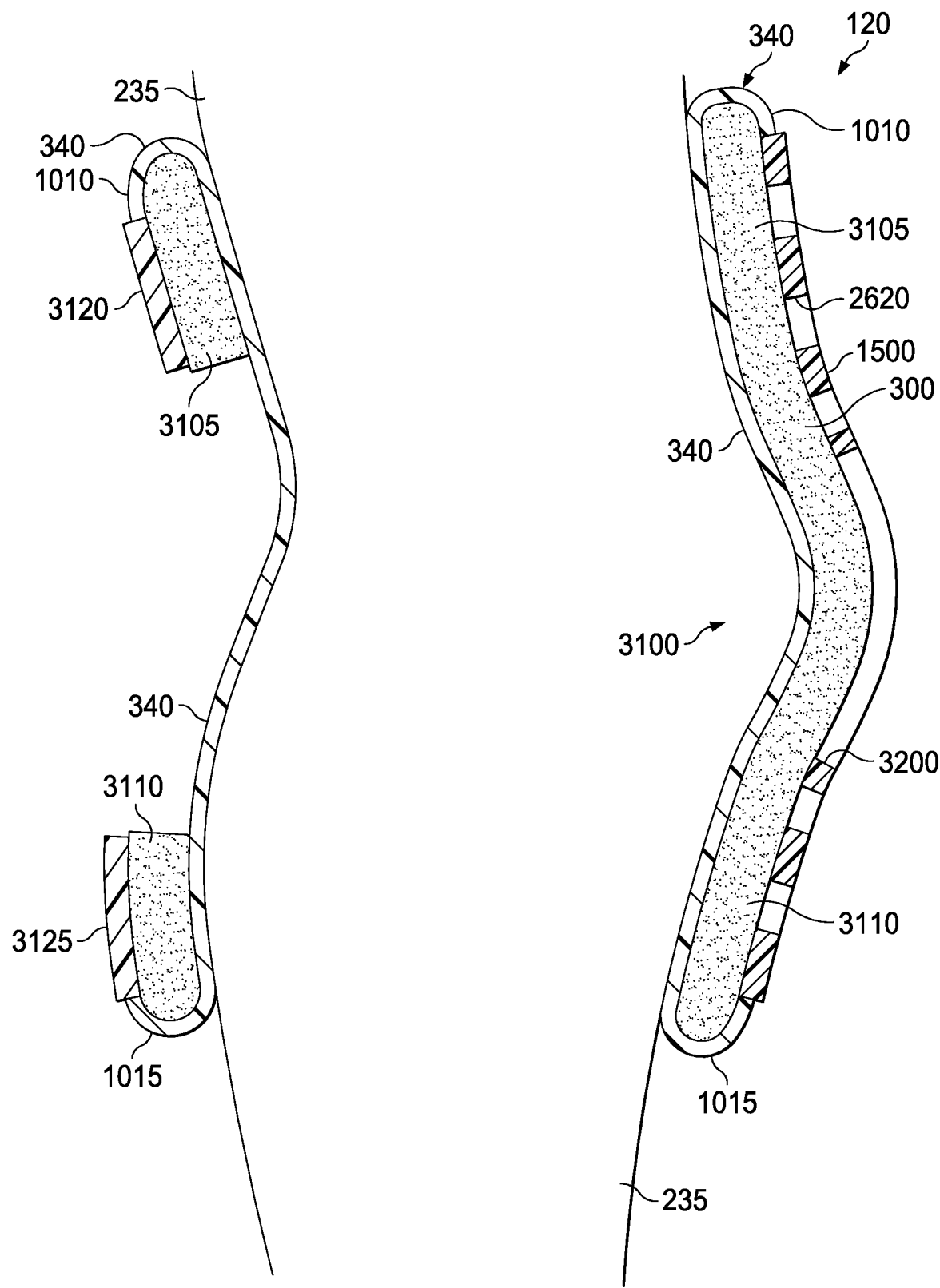
FIG. 34 is a section view of the tissue interface of FIG. 33.

FIG. 34 is a section view of the tissue interface 120 of FIG. 33 along line 34-34. As shown in FIG. 34, in some embodiments, the first end 1010 of the comfort layer 340 may be coupled to a side of the first cuff 3105 configured to face the cover 125. The comfort layer 340 may then extend over the top end of the first cuff 3105 and down to the second cuff 3110. The comfort layer 340 may then extend over the bottom end of the second cuff 3110 and the second end 1015 of the comfort layer 340 may be coupled to a side of the second cuff 3110 configured to face the cover 125. For example, the comfort layer 340 may have a first U- or C-shaped portion, which may cover the top end of the first cuff 3105, and second U-or C-shaped portion, which may cover the bottom end of the second cuff 3110. The U-or C-shaped portions may provide a smooth entry and exit surface to the tissue interface 120, which may result in increased comfort to the patient.

Figure 35:
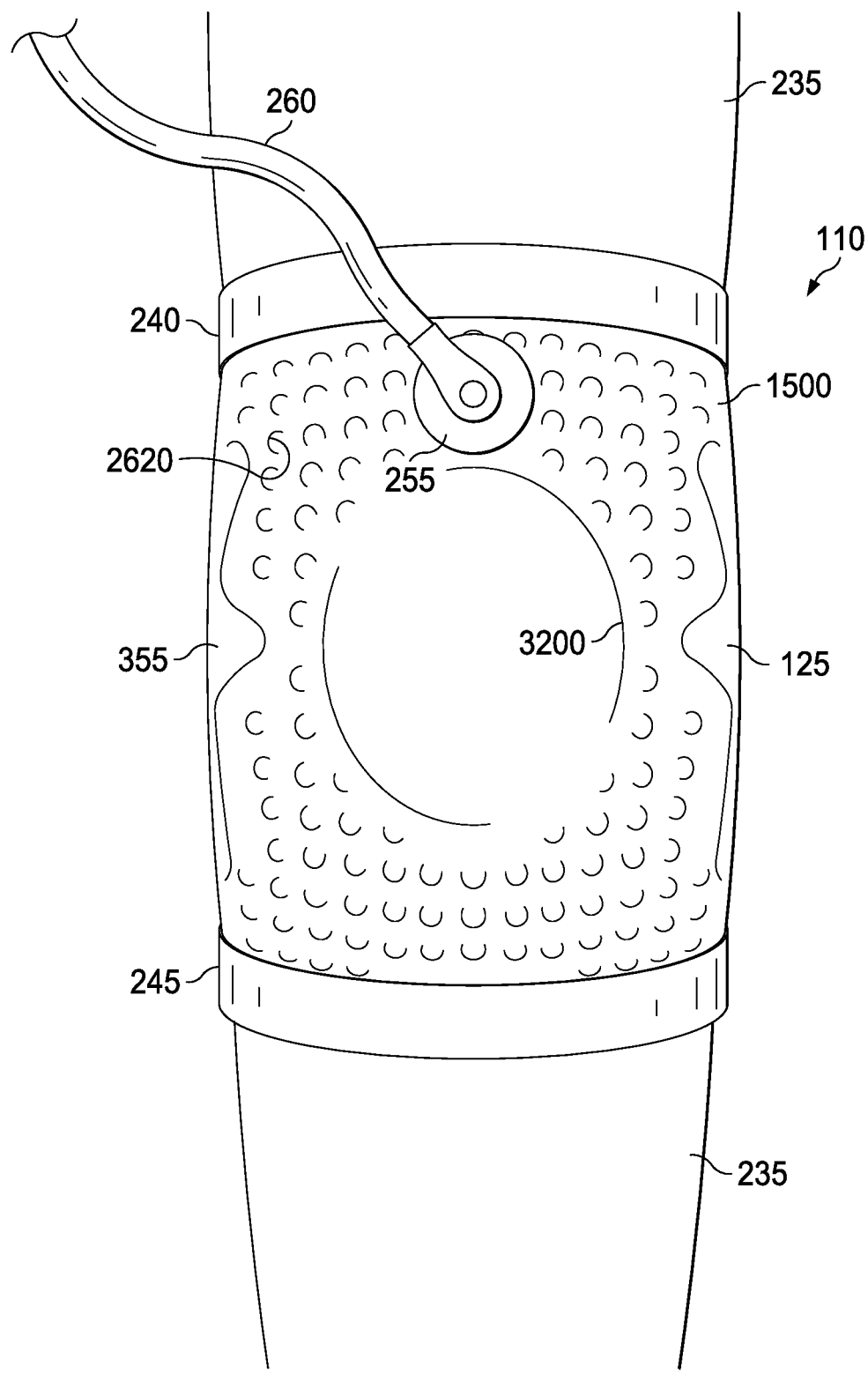
FIG. 35 is a front view of the dressing of FIG. 31.

FIG. 35 is a front view of the dressing 110 of FIG. 31. In the example embodiment of FIG. 35, the dressing 110 is shown under negative pressure. Upon the application of negative pressure, the cover 125 collapses and is pulled tightly against the support layer 1500. The outline of the support layer 1500, at least a portion of the plurality of apertures 2620, and the major aperture 3200 may then be visible through the cover 125. The appearance of the outline of the support layer 1500, the plurality of apertures 2620, and the major aperture 3200 through the cover 125 under the application of negative pressure may be useful as an indicia that negative pressure is being applied to the tissue interface 120. Due to the size of the dressing 110, and depending on the operating characteristics of the negative-pressure source 105, it may take some time to substantially or completely evacuate the chamber 355 of fluid. If the outline of the support layer 1500, the plurality of apertures 2620, and the major aperture 3200 cannot be identified through the cover 125 after a certain length of time that negative-pressure has been applied, it may be an indication of a leak in the dressing 110.

Figure 36:
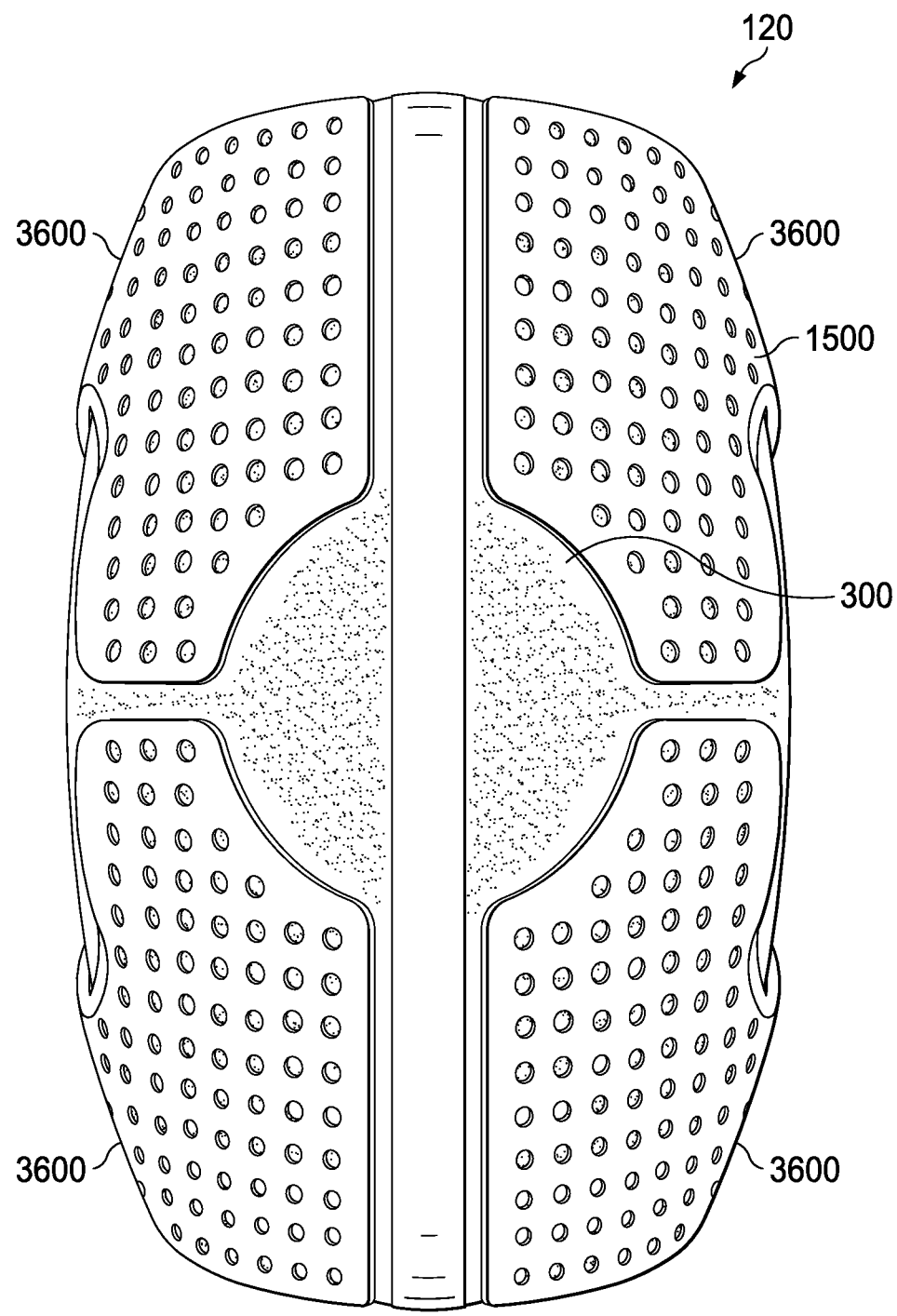
FIG. 36 is a front view of another example of a tissue interface, illustrating additional details that may be associated with some embodiments.

FIG. 36 is a front view of another example of the tissue interface 120, illustrating additional details that may be associated with some embodiments. In some embodiments, the support layer 1500 may comprise two or more separate support layer members 3600. The separate support layer members 3600 may provide increased range of motion of the knee (not shown) of a patient.

Figure 37:
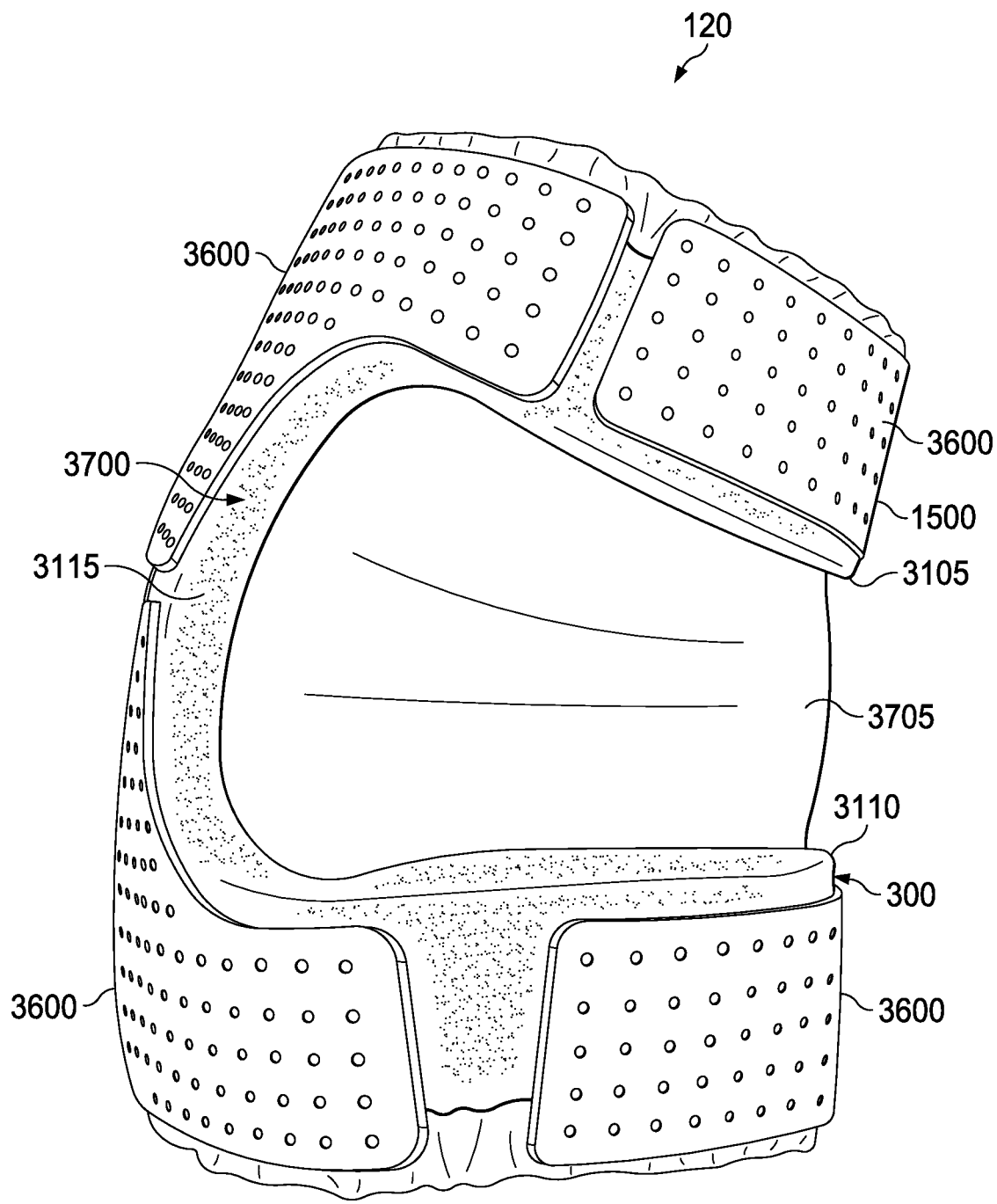
FIG. 37 is a rear isometric view of the tissue interface of FIG. 36.

FIG. 37 is a rear isometric view of the tissue interface 120 of FIG. 36. In some embodiments, the primary manifold 300 may comprise a first manifold portion 3700 and a second manifold portion 3705. The first manifold portion 3700 may include the stem 3115, the first cuff 3105, and the second cuff 3110. The second manifold portion 3705 that may extend over the popliteal fossa region of the knee (not shown). As shown in FIG. 37, in some embodiments, for example, the second manifold portion 3705 may be a separate piece of manifold material that is coupled to the first manifold portion 3700. In some embodiments, the second manifold portion 3705 may be integrally formed with the first manifold portion 3700. In some embodiments, the second manifold portion 3705 may be thinner than the first manifold portion 3700. The second manifold portion 3705 may provide for the application of negative pressure to the popliteal fossa region of the knee 3100, while the reduced thickness may still allow for range of motion of the knee (not shown).

Figure 38:
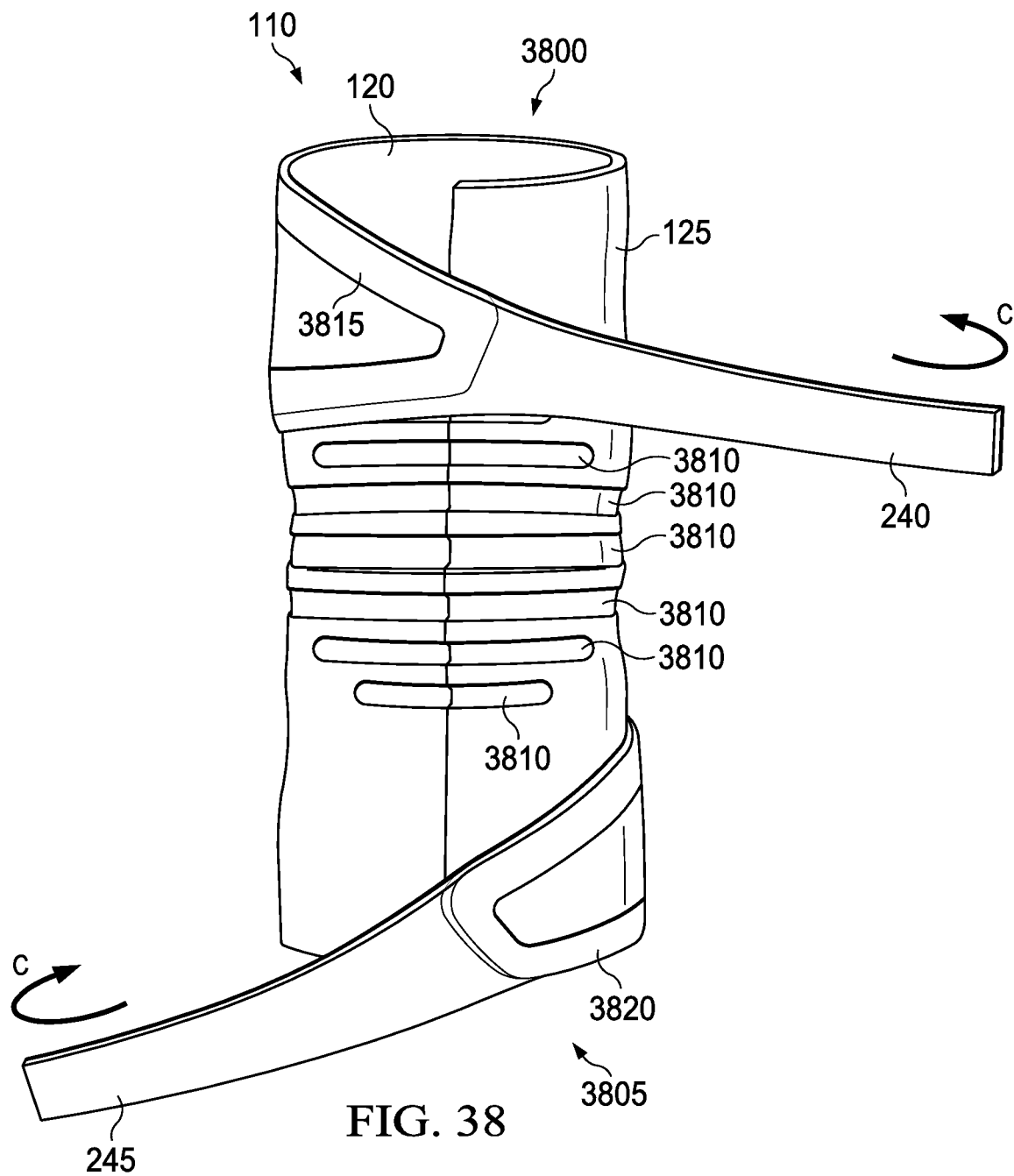
FIG. 38 is a rear view of another example of a dressing, illustrating additional details that may be associated with some embodiments.

FIG. 38 is a rear view of another example of the dressing 110, illustrating additional details that may be associated with some embodiments. The dressing 110 may be pulled over the foot, up the leg, and over the knee of the patient. The dressing 110 may be configured to deliver a negative pressure to a tissue site 200, such as, for example, proximate a knee (not shown) of a patient. The dressing 110 may have a tubular or sleeve shape and may have a first end 3800 and a second end 3805 that are open. The dressing 110 may have one or more recessed areas 3810 on the rear of the dressing 110 between the first end 3800 and the second end 3805. For example, the thickness of the tissue interface 120 in the location of the recessed areas 3810 may be less than the thickness of the tissue interface 120 in other locations of the tissue interface 120 such as the front of the tissue interface 120. The recessed areas 3810 may be formed into the tissue interface 120 in any suitable manner, such as, for example, die cutting, or molding. In FIG. 38, the recessed areas 3810 are shown as generally horizontal grooves; however, in some embodiments, the recessed areas 3810 may comprise a plurality of depressions formed into the tissue interface 120. The recessed areas 3810 may have a variety of suitable shapes, such as for example, circular, ovular, rectangular, square, hexagonal, pentagonal, and rectilinear.

As shown in FIG. 38, the dressing 110 may also include a first flap 3815 and a second flap 3820. The first flap 3815 may be proximate the first end 3800 and the second flap 3820 may be proximate the second end 3805. The first sealing member 240 may be coupled to and may extend from the first flap 3815. The second sealing member 245 may be coupled to and may extend from the second flap 3820. The first flap 3815 and the second flap 3820 may be pulled radially outward to expand the first end 3800 and the second end 3805, respectively. The expanded first end 3800 and the expanded second end 3805 may allow a patient to more easily pull the dressing up and over their knee (not shown), which may reduce discomfort to the patient, if the injury to the tissue site 200 is severe and/or there is significant swelling at the tissue site 200. Once the dressing 110 is located over the tissue site (not shown), the first sealing member 240 and the second sealing member 245 may be pulled (as shown by arrows C), thereby pulling the first flap 3815 and the second flap 3820 tight to the leg 235.

Figure 39:
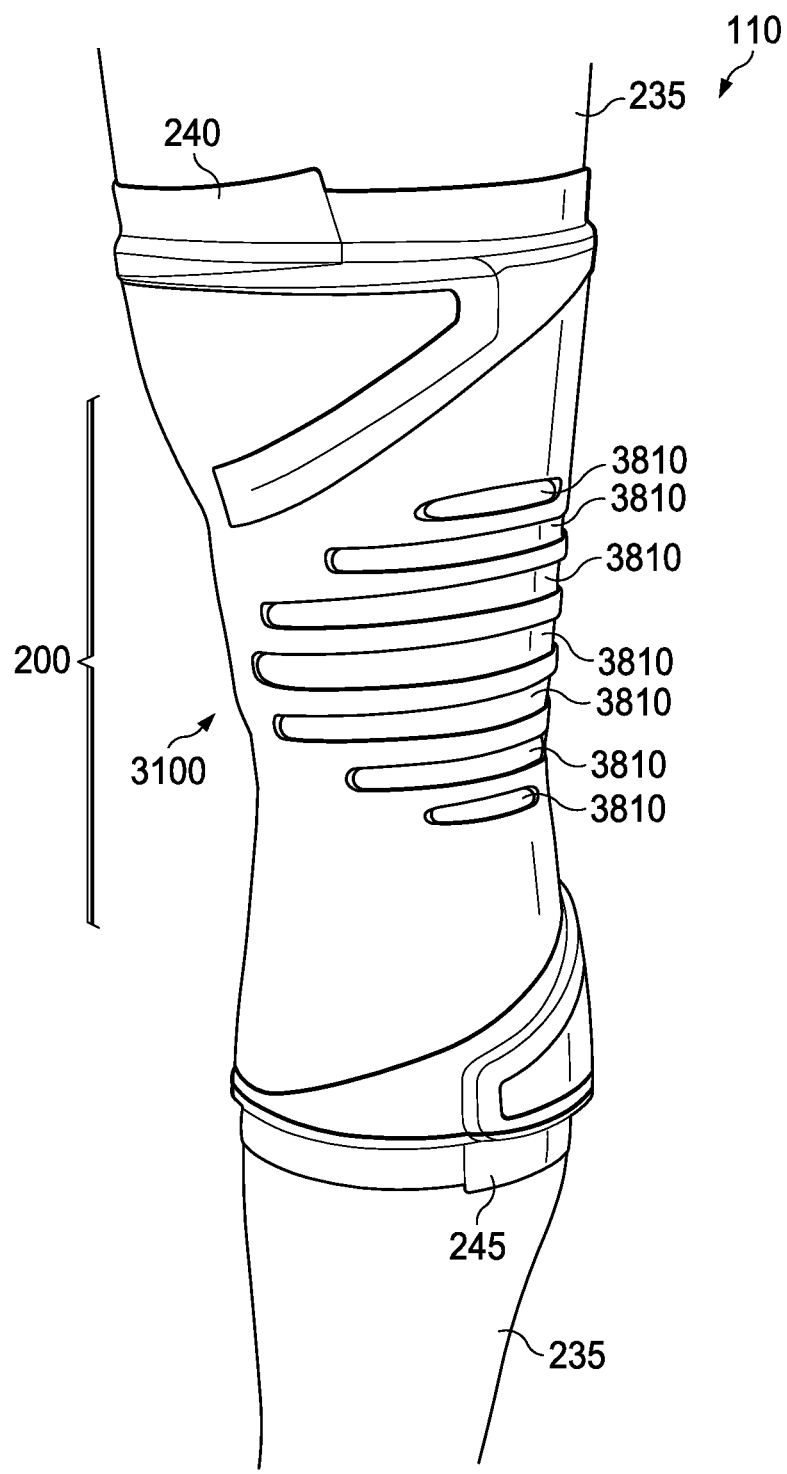
FIG. 39 is a rear isometric view of the dressing of FIG. 38.

FIG. 39 is a rear isometric view of the dressing 110 of FIG. 38. As shown in FIG. 39, the first sealing member 240 and the second sealing member 245 are wrapped around the leg 235 to seal the dressing 110 to the patient. A negative pressure may then be supplied to the tissue site 200. As shown in FIG. 38, the recessed areas 3810 may be located at the popliteal fossa region of the knee 3100, where the knee 3100 bends.

Figure 40:
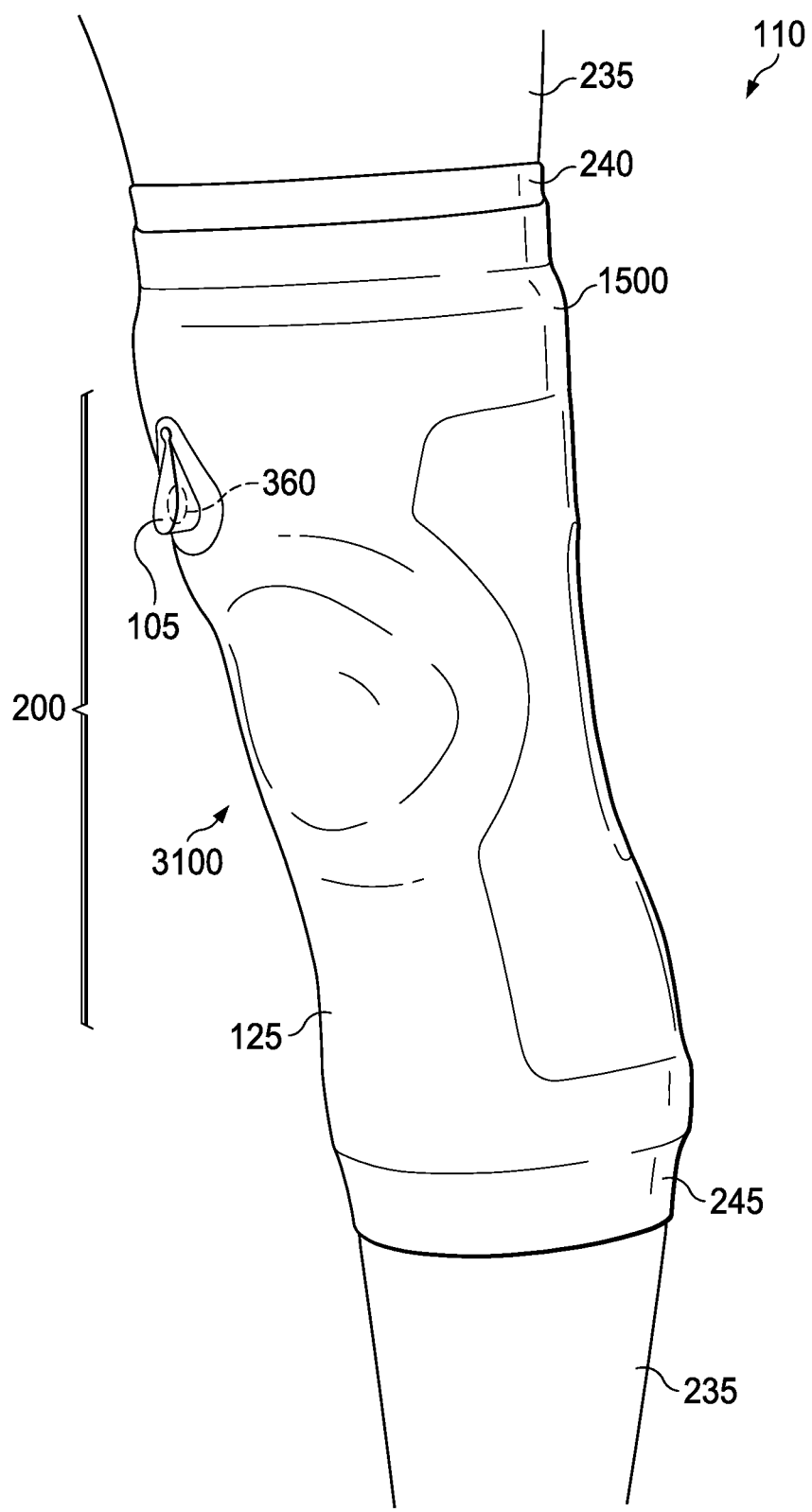
FIG. 40 is a front isometric view of another example of a dressing, illustrating additional details that may be associated with some embodiments.

FIG. 40 is an isometric view of another example of the dressing 110, illustrating additional details that may be associated with some embodiments. In the example of FIG. 40, the tissue site 200 comprises a knee 3100. Additionally, the negative-pressure source 105 may be a pump, which may be coupled to the cover 125 and fluidly coupled with the tissue interface 120 to supply negative pressure to the tissue site 200 through the aperture 360. In the example of FIG. 40, the aperture 360 is shown on the anterior side of the leg 235 above the knee 3100. In some embodiments, the aperture 360 may have other locations, such as the posterior side of the leg 235 above the knee 3100, the medial side of the leg 235 above the knee 3100, the lateral side of the leg 235 above the knee 3100, the anterior side of the leg 235 below the knee 3100, the posterior side of the leg 235 below the knee 3100, the medial side of the leg 235 below the knee 3100, or the lateral side of the leg 235 below the knee 3100. The tissue interface 120 may also include support layer 1500, the outline of which may be visible through the cover 125 under the application of negative pressure.

Figure 41:
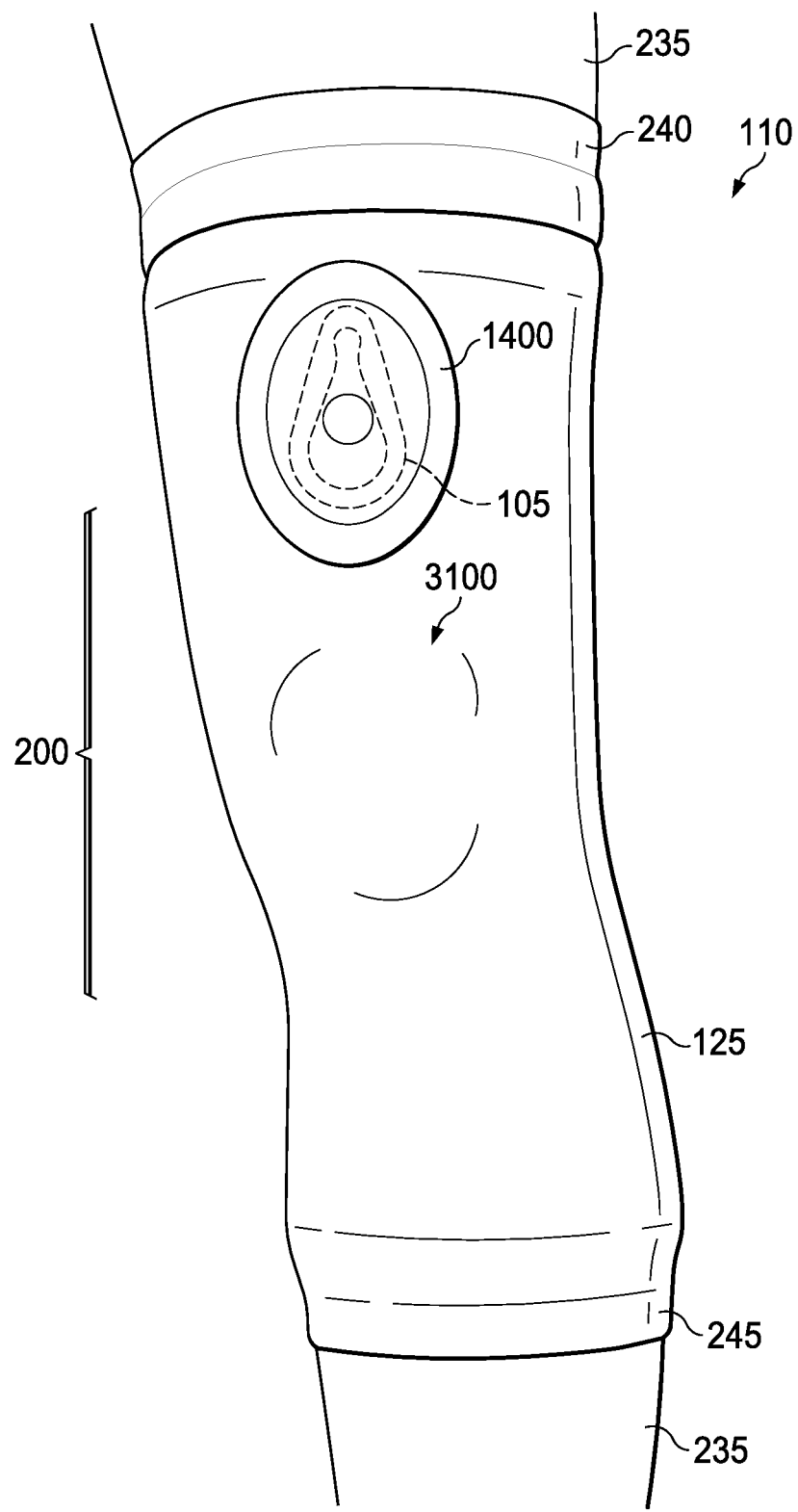
FIG. 41 is a front view of another example of a dressing, illustrating additional details that may be associated with some embodiments.

FIG. 41 is a front view of another example of the dressing 110, illustrating additional details that may be associated with some embodiments. As shown in FIG. 41, the pump actuator 1400 may be coupled to the dressing 110, wherein the pump actuator 1400 actuates the negative-pressure source 105 to deliver negative pressure to the tissue site 200.

Figure 42:
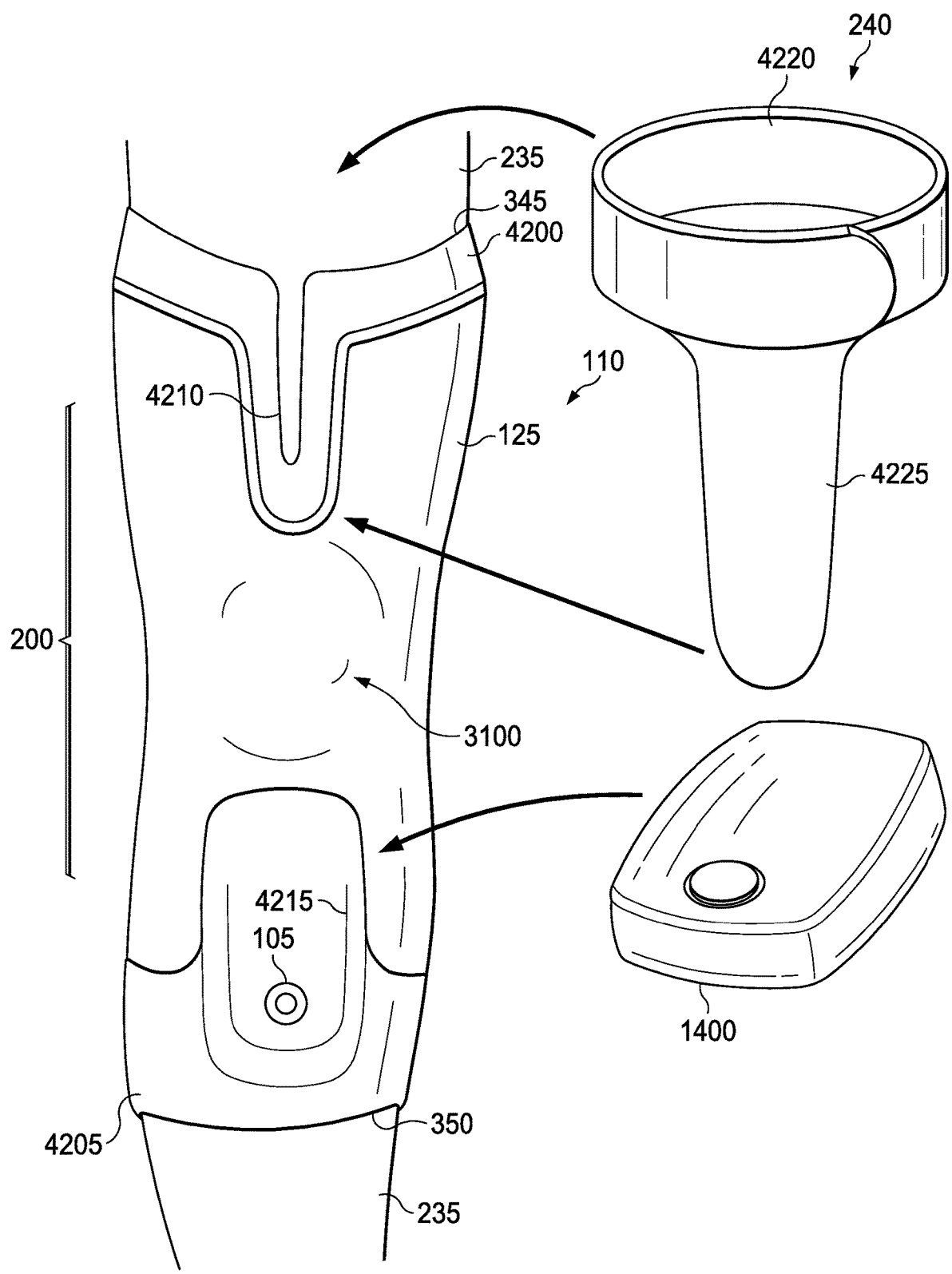
FIG. 42 is a front view of another example of a dressing, illustrating additional details that may be associated with some embodiments.

FIG. 42 is a front view of another example of the dressing 110, illustrating additional details that may be associated with some embodiments. As shown in FIG. 42, the cover 125 includes the first end 345 and the second end 350. The cover 125 may include a first reinforced portion 4200 proximate the first end 345 and a second reinforced portion 4205 proximate the second end 350. The first reinforced portion 4200 and the second reinforced portion 4205 may extend circumferentially around the first end 345 and the second end 350, respectively. The first reinforced portion 4200 may include an expansion joint 4210 extending downward toward the second end 350. The second reinforced portion 4205 may include a negative-pressure source 105 and a dock 4215. The first reinforced portion 4200 and the second reinforced portion 4205 may be formed of silicone. The dressing 110 may further include the first sealing member 240. First sealing member 240 may include a circumferential sealing portion 4220 and an expansion joint sealing portion 4225 extending away from the circumferential sealing portion 4220. The dressing 110 may further include a pump actuator 1400 that may be configured to be coupled to the dock 4215 on the dressing 110.

The first reinforced portion 4200 and the second reinforced portion 4205 of the cover 125 may permit multiple re-uses of the dressing 110 and/or the first sealing member 240. Additionally, the expansion joint 4210 provided in the first reinforced portion 4200 may allow for expansion of the first end 345 of the cover 125. The expansion joint 4210 may allow a patient to more easily pull the dressing up and over their knee 3100 and may reduce discomfort to the patient, if the injury to the tissue site 200 is severe and/or there is significant swelling at the tissue site 200. Once the dressing 110 is positioned on the knee 3100, the first end 345 of the cover 125 may be sealed to the leg 235 by first sealing member 240. Namely, the circumferential sealing portion 4220 may wrap around the first reinforced portion 4200 to seal the first end 345 to the leg and the expansion joint sealing portion 4225 may seal the expansion joint 4210. The first reinforced portion 4200 may reduce the amount of contact between the patient's skin and the first sealing member 240 and may provide increased comfort to the patient. The pump actuator 1400 may be coupled to the dock 4215 and may actuate the negative-pressure source 105 to provide a negative pressure to the tissue site 200. Following the application of negative pressure, the first sealing member 240 may be removed from the first reinforced portion 4200. Due to the reinforcement of the first reinforced portion 4200, the first reinforcement portion 4200 may remain intact after removal of the first sealing member 240. As such, the dressing 110 maybe reused at a later time to apply negative pressure to the tissue site 200. Similarly, the first sealing member 240 may also be reused. In some embodiments, a second sealing member 245 may be coupled to and removed from the second reinforced portion 4205 in a similar manner as the first sealing member 240. In some embodiments, the first sealing member 240 may be replaced with a new first sealing member 240 for a subsequent application of negative pressure to the tissue site 200.

Figure 43:
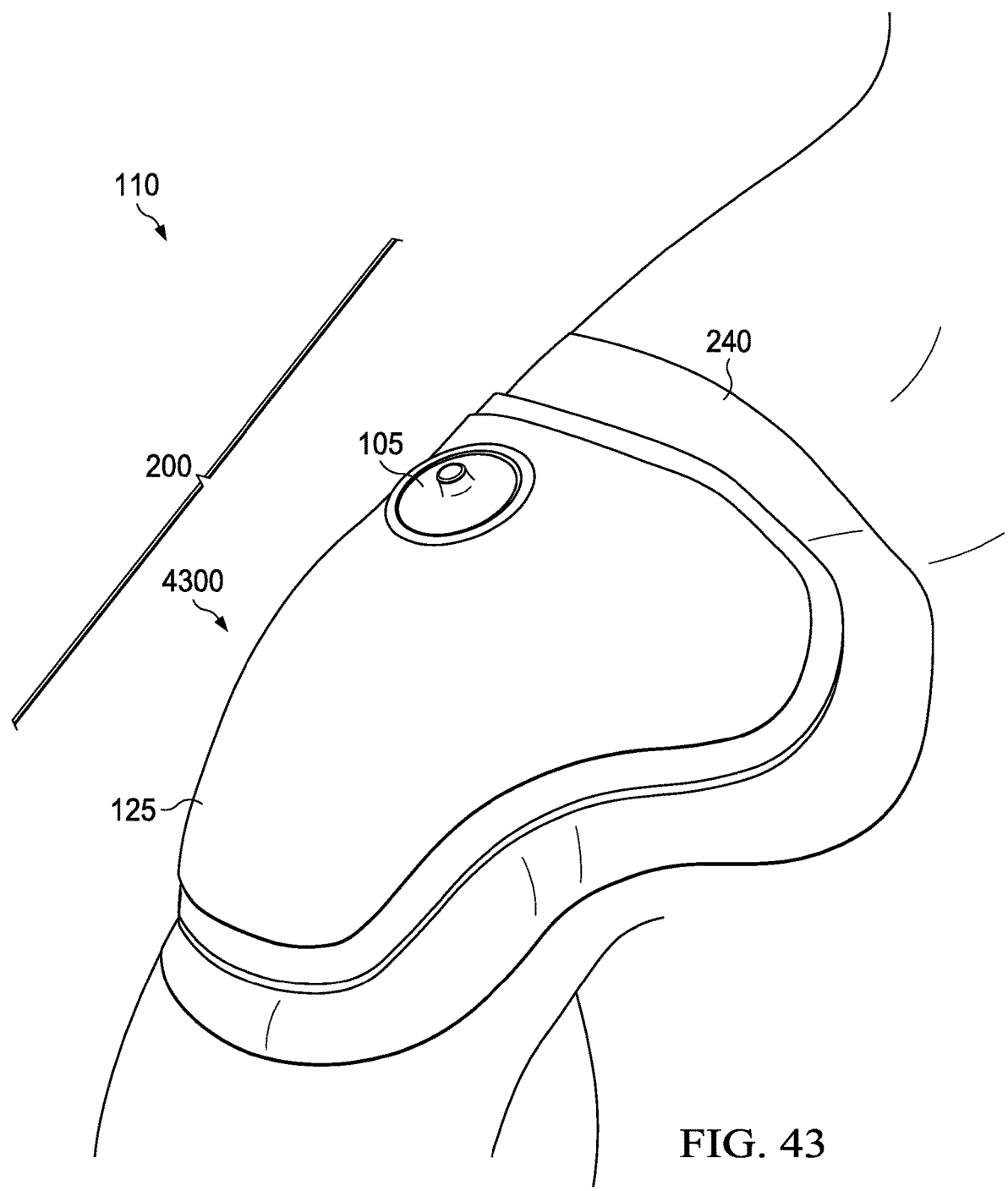
FIG. 43 is an isometric view of another example of a dressing, illustrating additional details that may be associated with some embodiments.

FIG. 43 is an isometric view of another example of the dressing 110, illustrating additional details that may be associated with some embodiments. In the example embodiment of FIG. 43, the dressing 110 is configured for delivering a negative pressure to a tissue site 200, such as, for example, proximate a shoulder 4300 of a patient. The dressing 110 includes the cover 125, first sealing member 240, and negative-pressure source 105. In some embodiments, the cover 125 may be concave and may be configured to cover at least a portion of the shoulder 4300. The first sealing member 240 may extend around the periphery of the cover 125 to attach the cover 125 to the shoulder 4300. The negative-pressure source 105 may be in fluid communication with the tissue site 200 proximate the shoulder 4300. As shown in FIG. 43, the dressing 110 may be configured such that it covers the shoulder 4300 of the patient. In some embodiments, the dressing 110 may be configured such that it covers at least a portion of one or more of the trapezius and the deltoid muscles of the patient. In some embodiments, the dressing 110 may be configured to cover the head of the patient's clavicle. In some embodiments, the dressing 110 may be configured to extend to the caudal or inferior edge of the deltoid muscle. In some embodiments, the dressing 110 may be configured to not cover the sternocleidomastoid.

Figure 44:
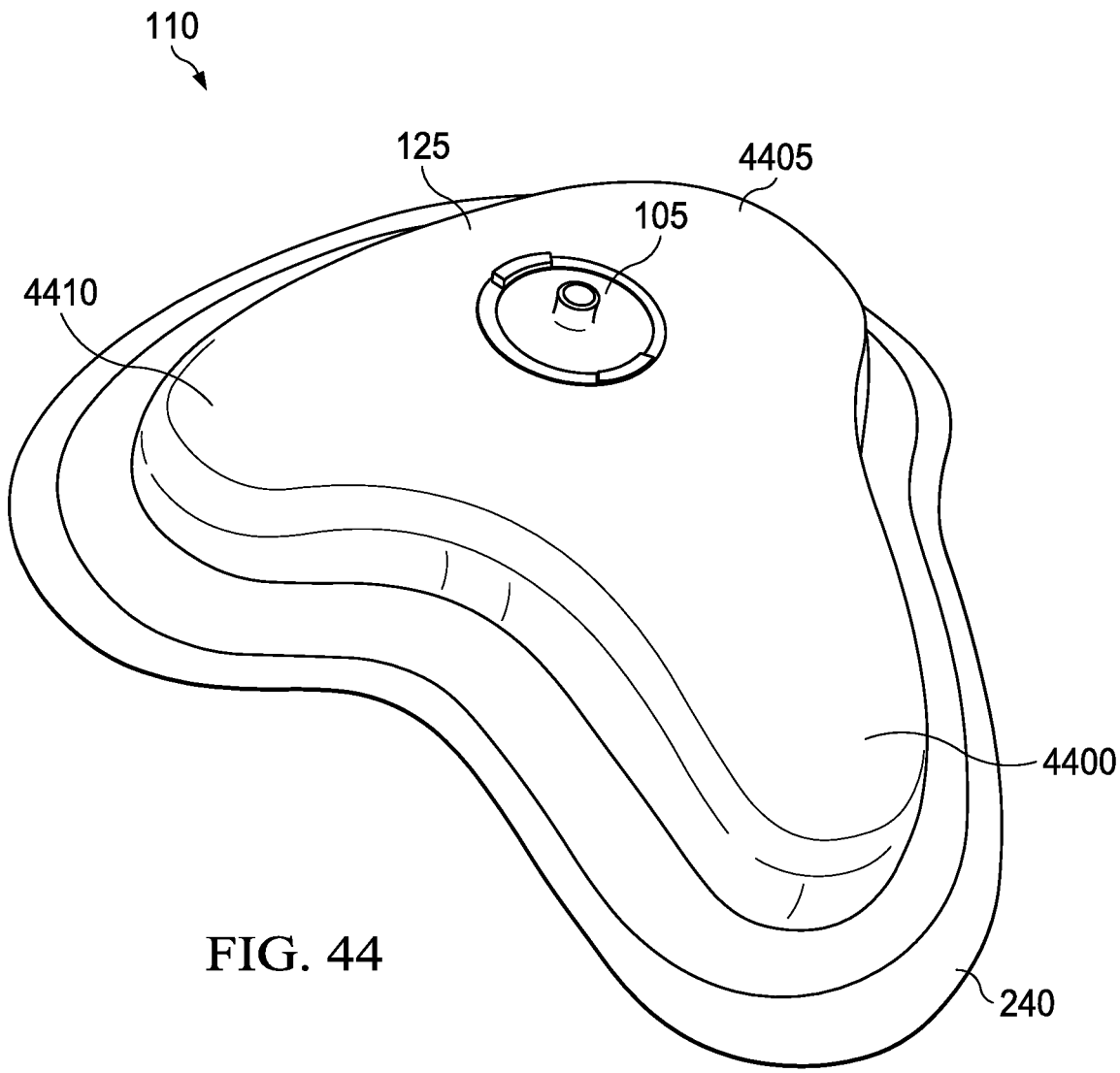
FIG. 44 is an isometric view of the dressing of FIG. 43.

FIG. 44 is an isometric view of the dressing 110 of FIG. 43. As shown in FIG. 44, the dressing 110 may comprise a plurality of lobes. For example, the dressing 110 may be trilobal, with a first lobe 4400, a second lobe 4405, and a third lobe 4410. The first lobe 4400 may be configured to extend over the lateral side of the shoulder 4300 and down at least a portion of the arm. The second lobe 4405 may be configured to extend over the anterior side of the shoulder 4300. The third lobe 4410 may be configured to extend over the posterior side of the shoulder 4300. In some embodiments, the first lobe 4400, the second lobe 4405, and the third lobe 4410 may be equally sized and shaped so that the dressing 110 may be placed in any orientation on the shoulder 4300. That is, the dressing 110 may be placed on the shoulder 4300 such that the second lobe 4405 may be extend over the lateral side of the shoulder 4300 and down at least a portion of the arm.

Figure 45:
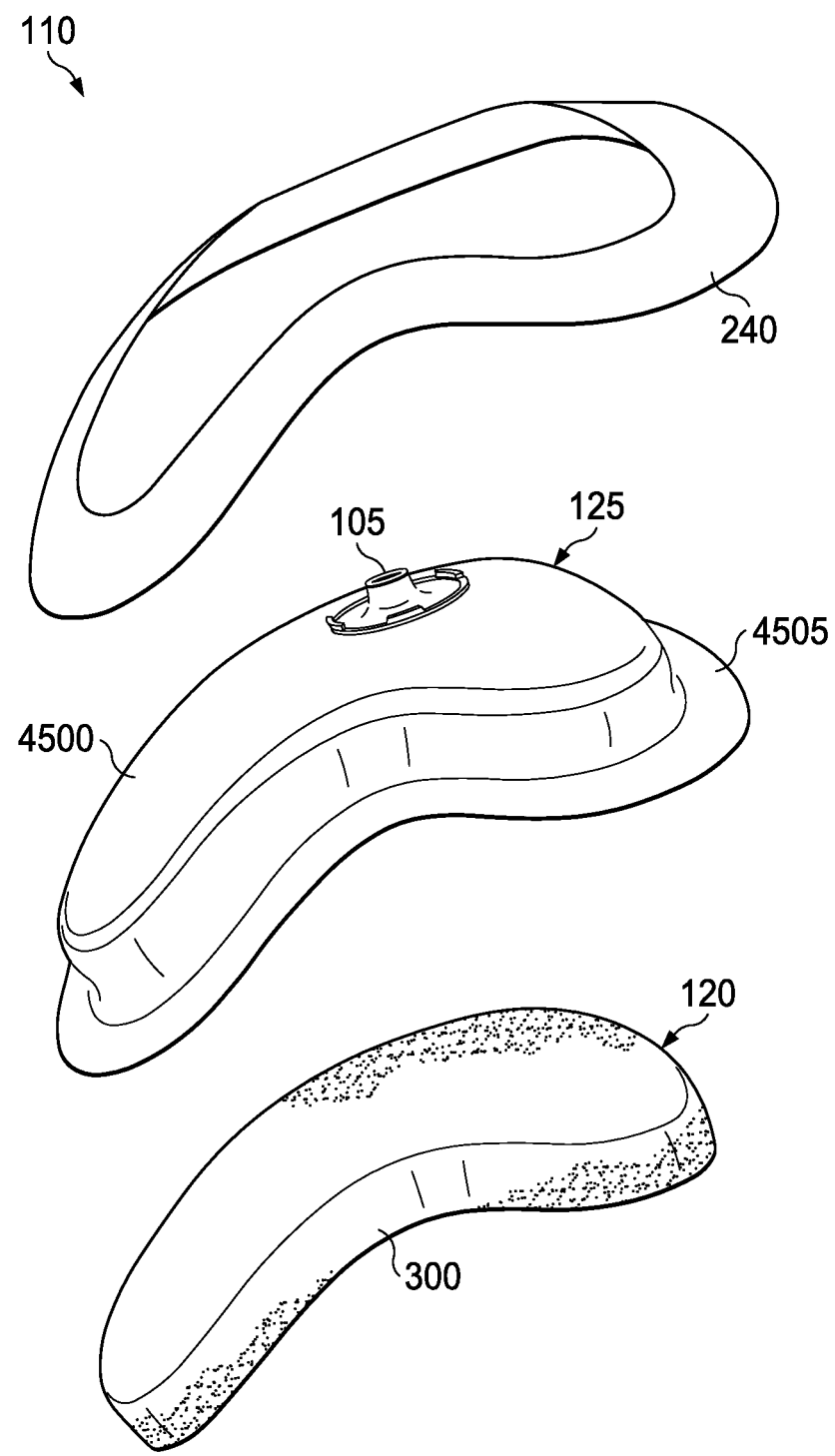
FIG. 45 is an exploded view of the dressing of FIG. 43.

FIG. 45 is an exploded view of the dressing 110 of FIG. 43. As shown in FIG. 45 the dressing 110 further includes the tissue interface 120, having the primary manifold 300, which is configured to be covered by cover 125. In the example embodiment shown in FIG. 45, the cover 125 comprises a domed portion 4500 and a flange 4505 extending outward from the bottom of the domed portion 4500. The flange 4505 may extend around the entire perimeter of the bottom of the domed portion 4500. The first sealing member 240 may be configured to be partially disposed over the flange 4505 to seal the cover 125 to a tissue site. The first sealing member 240 may be coupled to the flange 4505 and the tissue site and provide a seal around the tissue site. In some embodiments, the negative-pressure source 105 may be integrally formed into the cover 125. In some embodiments, the cover 125 may be molded from silicone. The cover 125 may be of a sufficient thickness to reduce, eliminate, or prevent collapse of the cover 125 when negative pressure is supplied to the tissue site 200. As the thickness of the cover 125 is increased, the pulling force of the dressing 110 under negative-pressure applied to the tissue site (not shown) may increase, which may result in increased perfusion through the tissue site (not shown). The cover 125 may be reusable, while in some embodiments, the first sealing member 240 and the tissue interface 120 may be disposable. In some embodiments, the tissue interface 120 may be reusable.

Figure 46:
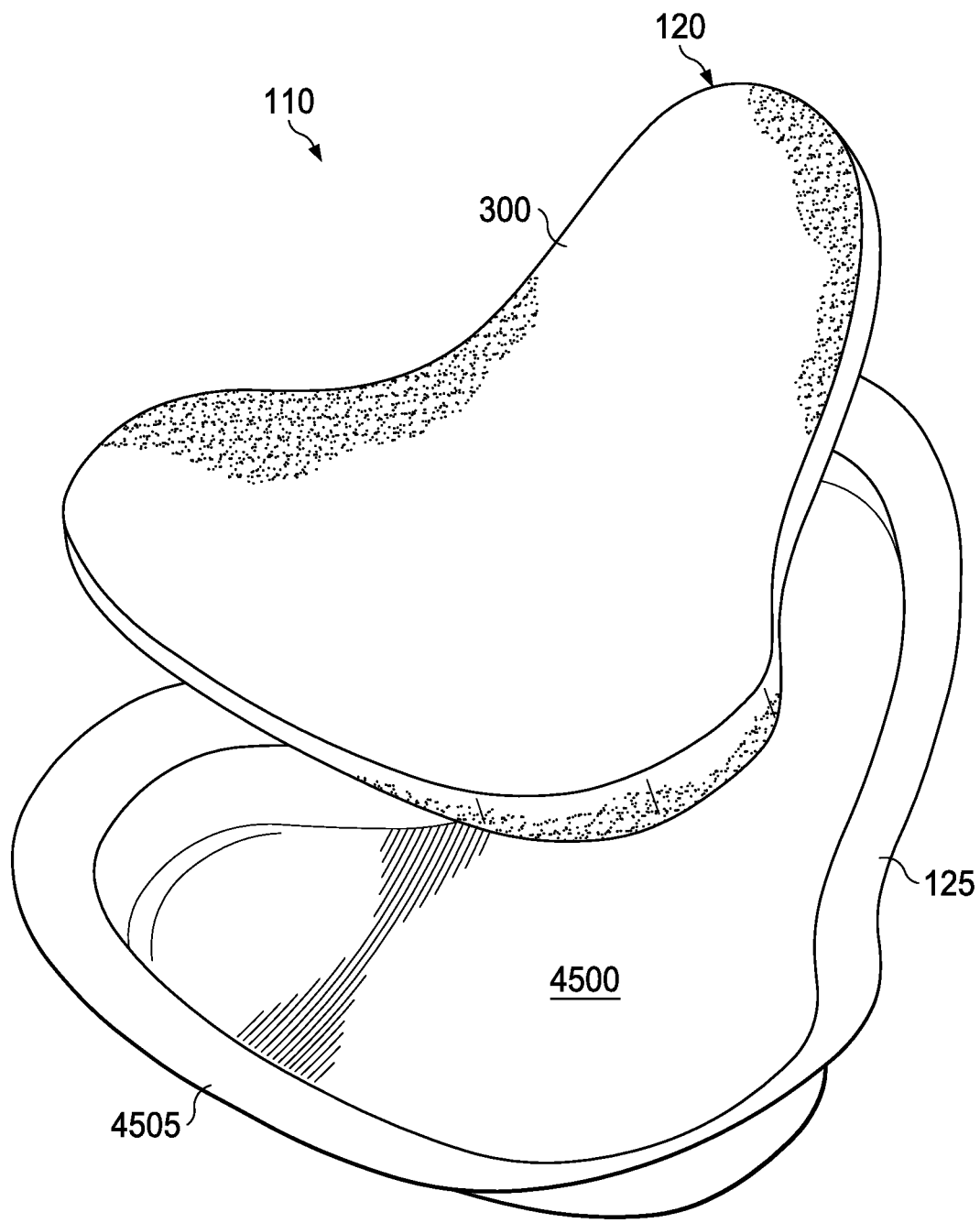
FIG. 46 is an exploded view of the tissue interface and the cover of the dressing of FIG. 43.

FIG. 46 is an exploded view of the tissue interface 120 and the cover 125 of the dressing 110 of FIG. 43. As shown in FIG. 46, the cover 125 and the tissue interface 120 may have a plurality of corresponding lobes. For example, the cover 125 and the tissue interface 120 may both be trilobal. In some embodiments, the tissue interface 120 has a size that corresponds to the interior size of the domed portion 4500. The tissue interface 120 may be inserted into the domed portion 4500 of the cover 125. In some embodiments, the tissue interface 120 may be coupled to the domed portion 4500 of the cover.

Figure 47:
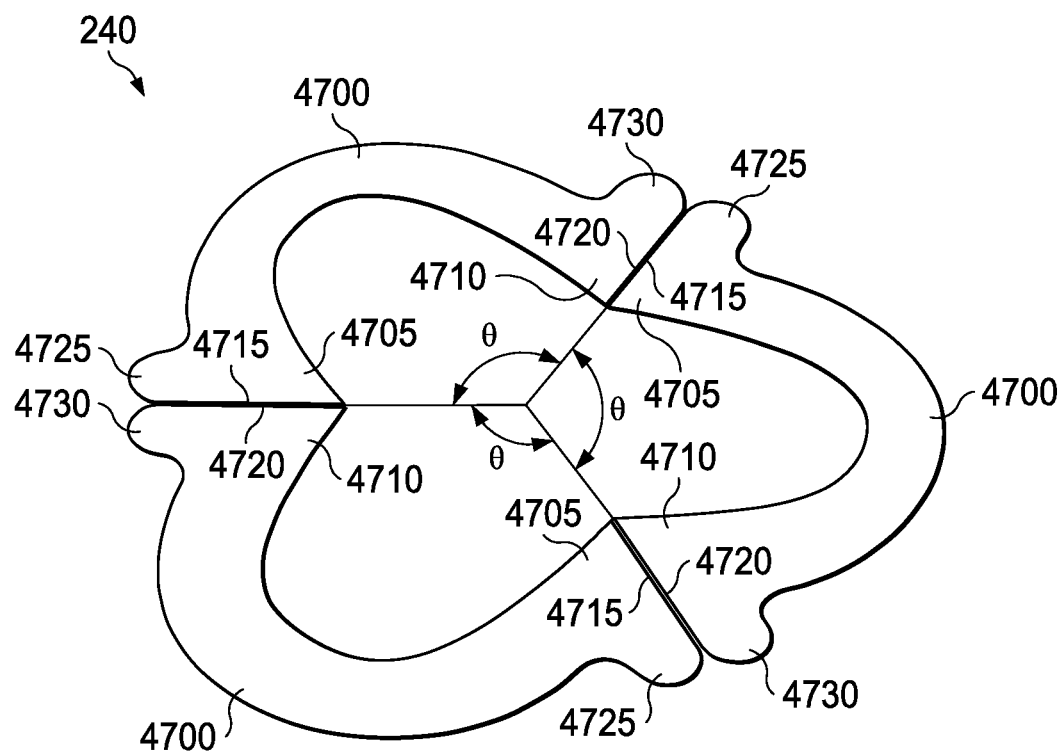
FIG. 47 is an isometric view of an example of a first sealing member, illustrating additional details that may be associated with some embodiments.

FIG. 47 is an isometric view of another example of the first sealing member 240, illustrating additional details that may be associated with some embodiments. The first sealing member 240 may include three sealing elements 4700, each of which may have an adhesive top side and an adhesive bottom side. In some embodiments, the three sealing elements 4700 are identical to one another. Each sealing element 4700 may be substantially U-shaped having a first end 4705 and a second end 4710. In some embodiments, the first end 4705 may have a first terminal edge 4715 and the second end 4710 may have a second terminal edge 4720, wherein the second terminal edge 4720 may be at an angle θ with respect to the first terminal edge 4715. In some embodiments, the angle θ may be about 120 degrees. Each sealing element 4700 may further include a first tab 4725 and a second tab 4730 extending outward from the first end 4705 and the second end 4710, respectively. In some embodiments, the first tab 4725 and the second tab 4730 may not include any adhesive on one or more of a top side and a bottom side of the first tab 4725 and the second tab 4730. In some embodiments, the first sealing member 240 may have more than three sealing elements 4700 (e.g., four sealing elements 4700, five sealing elements 4700, six sealing elements 4700, seven sealing elements 4700, etc.). In some embodiments, the first sealing member 240 may have less than three sealing elements 4700 (e.g., two sealing elements 4700, one sealing element 4700).

The three sealing elements 4700 of the first sealing member 240 may make it easier for a user of the dressing 110 to apply the first sealing member 240 to their own shoulder. The user can apply each sealing element 4700 to their shoulder one sealing element 4700 at a time. For example, the user can couple a first sealing element 4700 on their shoulder. Then, the user can couple a second sealing element 4700 to their shoulder with a first terminal edge 4715 of the second sealing element 4700 abutting or overlaying a second terminal edge 4720 of the first sealing element 4700. After the second sealing element is applied, the user can couple a third sealing element 4700 to their shoulder with a first terminal edge 4715 of the third sealing element 4700 abutting or overlaying a second terminal edge 4720 of the second sealing element 4700 and a second terminal end 4720 of the third sealing element 4700 abutting or overlaying a first terminal edge 4715 of the first sealing element 4700. The user can use one or more of the first tab 4725 and the second tab 4730 to aid in coupling and locating the sealing element 4700 in the desired location on their shoulder.

Figure 48:
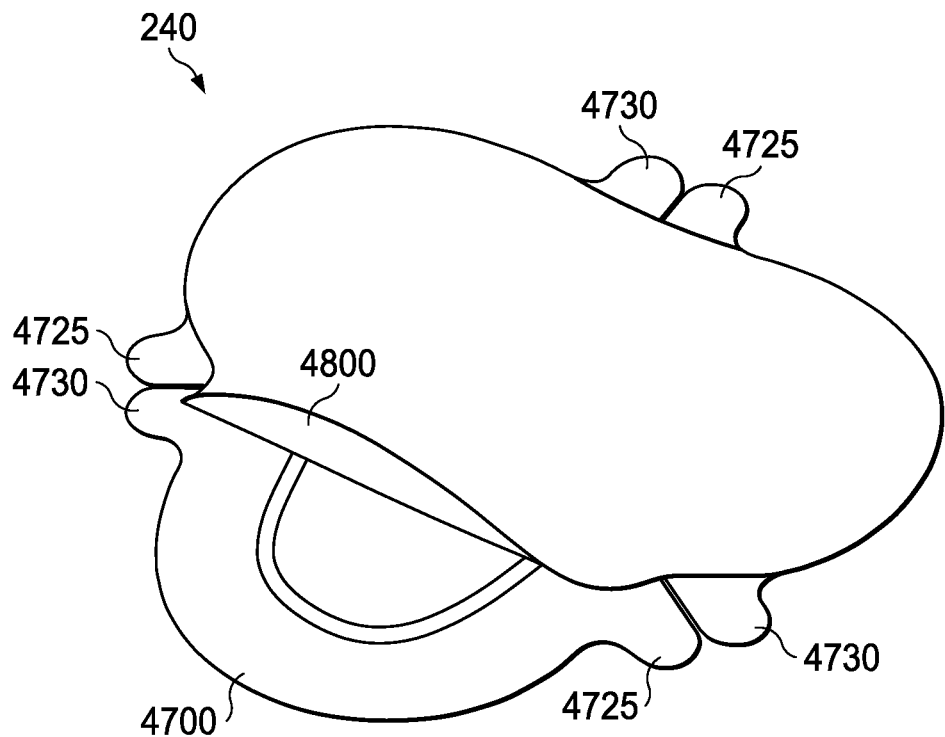
FIG. 48 is an isometric view of the first sealing member of FIG. 47.

FIG. 48 is an isometric view of the first sealing member 240 of FIG. 47. As shown in FIG. 48, in some embodiments the first sealing member 240 may include one or more release liners 4800 attached to or positioned adjacent to one or more of the top side of the first sealing member 240 and the bottom side of the first sealing member 240 to protect the adhesive of the first sealing member 240 prior to use. The release liner 4800 may also provide stiffness to assist with, for example, deployment of the first sealing member 240. The release liner 4800 may be, for example, a casting paper, a film, or polyethylene. Further, in some embodiments, the release liner 4800 may be a polyester material such as polyethylene terephthalate (PET), or similar polar semi-crystalline polymer. The use of a polar semi-crystalline polymer for the release liner 4800 may substantially preclude wrinkling or other deformation of the first sealing member 240. For example, the polar semi-crystalline polymer may be highly orientated and resistant to softening, swelling, or other deformation that may occur when brought into contact with components of the first sealing member 240, or when subjected to temperature or environmental variations, or sterilization. In some embodiments, the release liner 4800 may have a surface texture that may be imprinted on an adjacent layer, such as the first sealing member 240. Further, a release agent may be disposed on a side of the release liner 4800 that is configured to contact the first sealing member 240. For example, the release agent may be a silicone coating and may have a release factor suitable to facilitate removal of the release liner 4800 by hand and without damaging or deforming the first sealing member 240. In some embodiments, the release agent may be a fluorocarbon or a fluorosilicone, for example. In other embodiments, the release liner 4800 may be uncoated or otherwise used without a release agent.

Figure 49:
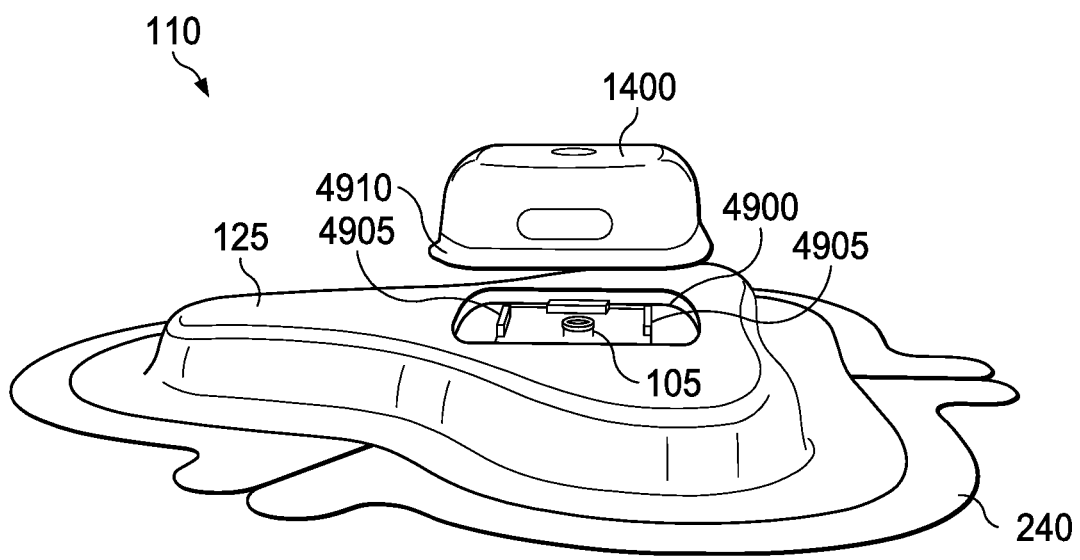
FIG. 49 is an isometric view of an example of a dressing and a pump actuator, illustrating additional details that may be associated with some embodiments.

FIG. 49 is an isometric view of an example of the dressing 110 and the pump actuator 1400, illustrating additional details that may be associated with some embodiments. As shown in FIG. 49, the cover 125 of the dressing 110 may include a recessed region 4900 in which the negative-pressure source 105 may be located. The dressing 110 may further include one or more attachment members 4905. Additionally, as shown in the example FIG. 39, some embodiments of the pump actuator 1400 may include a filleted flange 4910 extending around the perimeter of the pump actuator 1400. The pump actuator 1400 and the recessed region 4900 of the cover 125 may be configured to cooperate with one another. For example, the recessed region 4900 may have a rounded rectangular shape and the pump actuator 1400 may have a rounded rectangular shape. The pump actuator 1400 may be configured to be received in the recessed region 4900 of the cover 125. In some embodiments, the pump actuator 1400 may also clip onto the one or more attachment members 4905 to secure the pump actuator 1400 to the dressing 110.

Figure 50:
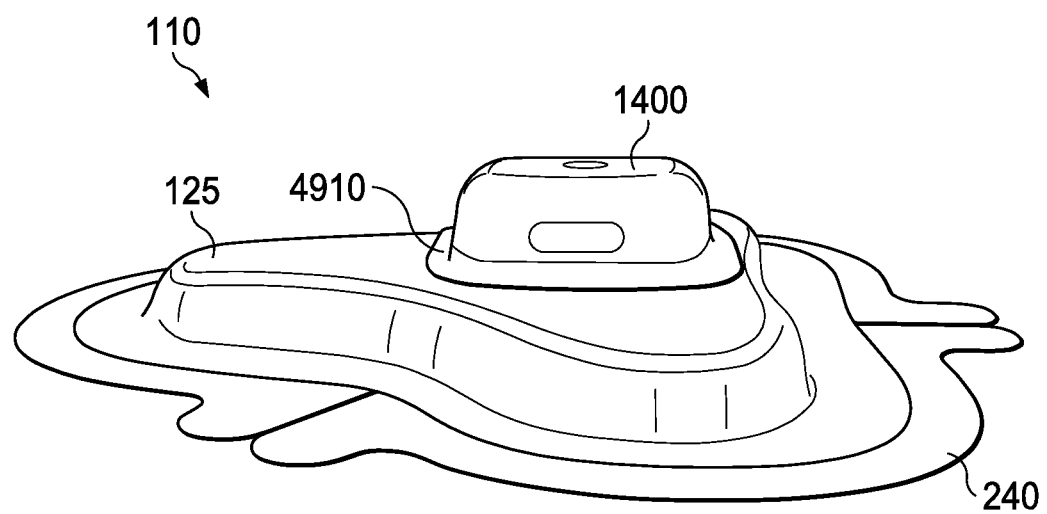
FIG. 50 is an isometric view of the dressing and the pump actuator of FIG. 49.

FIG. 50 is an isometric view of the dressing 110 and the pump actuator 1400 of FIG. 49. As shown in FIG. 50, the pump actuator 1400 is coupled to the dressing 110. When the pump actuator 1400 is inserted into the recessed region 4900, the bottom of the filleted flange 4910 sits flush with the cover 125. The flush mount of the filleted flange 4910 to the cover 125 may prevent items such as clothing from sliding between the filleted flange 4910 and the cover 125 and may reduce or eliminate the possibility of accidental lifting of the pump actuator 1400 off of the dressing 110.

Figure 51:
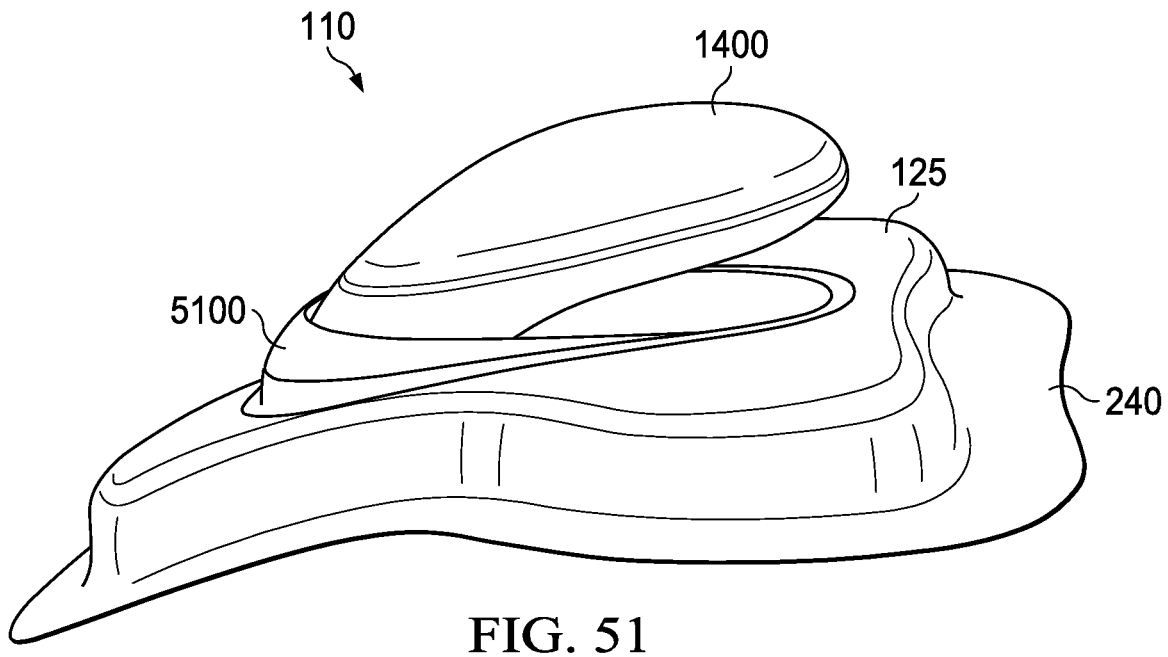
FIG. 51 is an isometric view of other examples of a dressing and a pump actuator, illustrating additional details that may be associated with some embodiments.

FIG. 51 is an isometric view of other examples of the dressing 110 and the pump actuator 1400, illustrating additional details that may be associated with some embodiments. As shown in FIG. 51, the cover 125 of the dressing 110 may include a pocket 5100 into which the pump actuator 1400 may be inserted. The pocket 5100 may aid in securing the pump actuator 1400 to the dressing 110.

Figure 52:
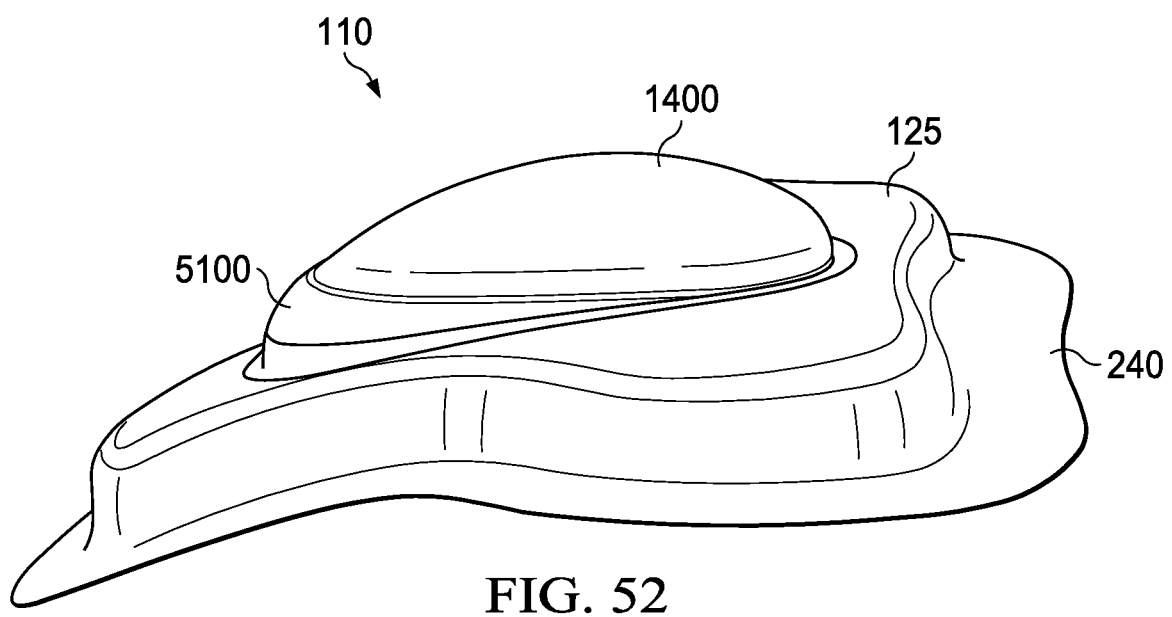
FIG. 52 is an isometric view of the dressing and the pump actuator of FIG. 51.

FIG. 52 is an isometric view of the dressing 110 and the pump actuator 1400 of FIG. 51. As shown in FIG. 52, the pump actuator 1400 is inserted into the pocket 5100 and coupled to the dressing 110.

Figure 53:
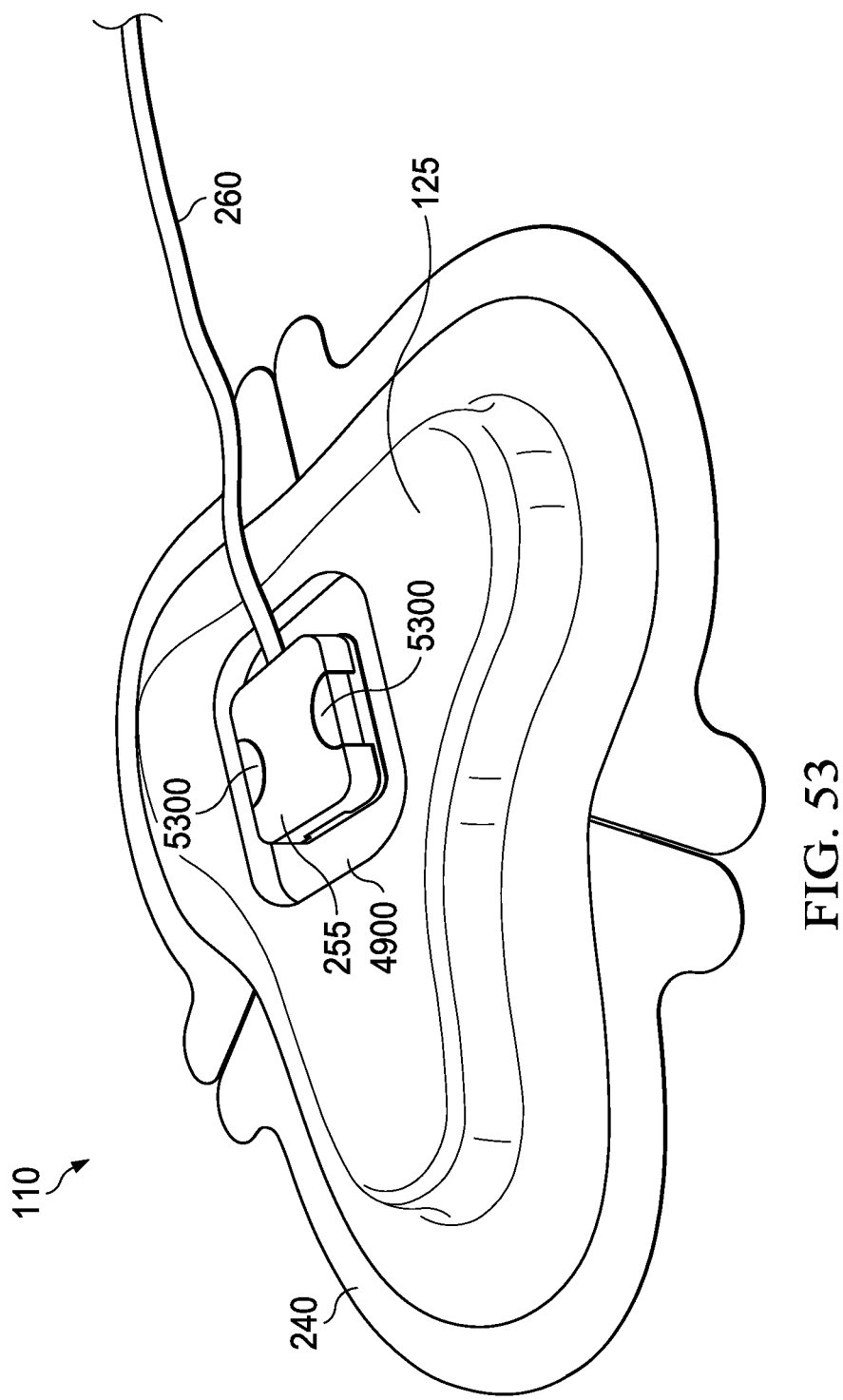
FIG. 53 is an isometric view of the dressing of FIG. 49.

FIG. 53 is an isometric view of the dressing 110 of FIG. 49. As shown in FIG. 53, the dressing 110 may include a dressing interface 255 that may be configured to releasably couple with the dressing 110. The dressing interface 255 may have a rounded rectangular shape and may be configured to be received in the recessed region 4900 of the cover 125. The dressing interface 255 may releasably couple with the cover 125. For example, the dressing interface 255 may couple to the one or more attachment members 4905 provided on the cover 125 (see FIG. 49). The dressing interface 255 may include buttons 5300 that may allow removal of the dressing interface 255 from the cover 125 when pressed. The fluid conductor 260 may be fluidly coupled with the dressing interface 255 to provide negative pressure to the dressing 110.

The systems, apparatuses, and methods described herein may provide significant advantages. For example, use of the dressing 110 with negative pressure to treat wounds, strains, sprains, and other injuries to ankles and other joints can significantly reduce recovery time. The standard of care for strains and sprains for many decades has included rest, ice, compression and elevation. After a period of anywhere from 10 days to 24 weeks for minor injuries, patients commonly report a reduction in pain and return to motion. For major injuries, however, patients report a reduction in pain after one year, two years, and even more time. Even after these lengthy time periods, an equally significant number of patients still report pain and no return to motion.

Healing time for more traumatic sprains and strains with rest, ice, compression, and elevation can be much longer, typically ranging from 4 to 6 months. Even then, if the injury is still unstable after this time, surgery is often required to stabilize the joint. This prolonged healing time represents a significant loss of mobility, and delay in return to functional activity. Even for the majority of sprains and strains, the current standard of care also suffers from several practical drawbacks in addition to inadequate healing. Ice can only be applied for a limited time, as prolonged contact is either not practical because it melts or causes even more discomfort and pain because of the cold temperature being applied to the affected extremity. Compression with current devices, especially with elastic wraps, is either inadequate for applying a sufficient and consistent positive force (e.g., the wrap slips over time or is applied and re-applied incorrectly), or actually restricts blood flow and lymph flow.

The dressing 110 can apply the negative pressure to the epidermis 335, extending over or surrounding the tissue site 200, which can effectively splint and stabilize a joint, such as the ankle joint 230 of the foot 205. Negative pressure applied to the epidermis 335 can also pull the tissue site 200 outwardly toward the cover 125. This pulling force adjacent to the epidermis 335, coupled with the immobilization of the joint, can stimulate the blood flow (perfusion) and lymphatic flow at the tissue site 200, which can accelerate healing of the damaged ligament and/or muscle. Damaged tissue can be properly supplied and evacuated with blood flow and lymph flow, thereby promoting perfusion in the subcutaneous portions of the tissue site 200 and reducing edema to accelerate healing. In contrast, current treatments may only temporarily reduce inflammation by icing and may actually constrict blood flow and lymph flow by compression. Moreover, stabilizing elements such as the stabilizing members 225 can significantly reduce or eliminate the risk of further injury to the tissue site 200. Additionally, the toe box 220 can allow the toes 302 to remain uncompressed when negative pressure is applied to the tissue site 200. Compression of the toes 302 under negative pressure may be uncomfortable or painful for some patients. Thus, by preventing compression of the toes 302 during negative-pressure therapy, patient comfort and compliance may also be increased.

Thus, the therapy system 100 can provide the advantages of managing pain by reducing swelling and inflammation, increasing stability to the tissue site 200, eliminating compression of the toes 302 of the patient, and accelerating healing by increasing blood flow and lymph flow.

In some embodiments, the fluid conductor 260 may be opaque, colored (e.g., black, white, red, blue, green), textured, and/or wrapped or encased in a decorative sleeve. In some embodiments, the sleeve may be woven for aesthetics. For example, the fluid conductor 260 may have an appearance similar to a headphone cord in some configurations. Additionally or alternatively, the dressing 110 may be opaque, colored (e.g., black, white, red, blue, green), textured, and/or wrapped or encased in a decorative sleeve to improve aesthetics or camouflage the dressing 110. In some embodiments, for example, the dressing 110 may be used to treat a sports injury, and the dressing 110 may be coordinated with team colors. In other examples, a patient may select colors and/or logo of their favorite team. In some embodiments, the dressing 110 may be decorated with camouflage, which may be advantageous to hunters. Increasing aesthetics can also increase patient compliance and decrease recovery time.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110 may be separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for applying negative pressure to a tissue site of a patient, the apparatus comprising:
    a tissue interface having an anatomical shape configured to cover the tissue site;
    a cover configured to cover the tissue interface;
    a support layer configured to be located between the tissue interface and the cover, wherein the support layer is configured to increase a pulling force on the tissue site under negative pressure;
    an aperture extending through the cover, the aperture fluidly coupled to the tissue interface; and
    a sealing member configured to seal the cover to the patient, wherein the cover and the sealing member are configured to cooperate to form a sealed chamber containing the tissue interface and the support layer.

2. The apparatus of claim 1, wherein the anatomical shape is configured to cover a foot.

3. The apparatus of claim 2, wherein the tissue interface is further configured to circumferentially cover a portion of a leg, at least a portion of an ankle, and a portion of a foot of the patient.

4. The apparatus of claim 2, wherein the tissue interface comprises a toe portion that is open.

5. The apparatus of claim 2, wherein the cover has a first end that is open.

6. The apparatus of claim 5, wherein the sealing member is configured to extend around the first end of the cover to seal the first end of the cover to the leg of the patient.

7. The apparatus of claim 2, further comprising a toe box configured to cover toes of the patient.

8. The apparatus of claim 7, wherein the cover is further configured to cover the toe box.

9. The apparatus of claim 8, wherein the sealed chamber further contains the toe box.

10. The apparatus of claim 7, wherein the tissue interface comprises:
    a first portion configured to circumferentially cover at least a portion of the dorsum and the plantar of the foot; and
    a second portion connected to the first portion, the second portion configured to circumferentially cover at least a portion of the crus of the patient.

11. The apparatus of claim 7, wherein the tissue interface comprises:
    a sole portion;
    a vamp portion coupled to the sole portion;
    a quarter portion coupled to the sole portion and the vamp portion; and
    a calf portion coupled to and extending upward from the quarter portion.

12. The apparatus of claim 7, wherein the toe box comprises a foam having closed cells.

13. The apparatus of claim 7, wherein the toe box includes one or more toe separations.

14. The apparatus of claim 7, wherein the toe box is configured to prevent the toes from being compressed when negative pressure is applied to the tissue interface.

15. The apparatus of claim 7, wherein the toe box further includes antimicrobial properties.

16. The apparatus of claim 2, wherein the aperture is configured to be located proximate one of the leg, ankle, and foot of the patient.

17. The apparatus of claim 2, wherein the aperture is configured to be located on one of the anterior side of the leg, the posterior side of the leg, the medial side of the leg, and the lateral side of the leg.

18. The apparatus of claim 3, wherein the aperture is configured to be located on one of the anterior side of the ankle, the posterior side of the ankle, the medial side of the ankle, and the lateral side of the ankle.

19. The apparatus of claim 2, wherein the aperture is configured to be located on one of the dorsum of the foot, the plantar of the foot, the medial side of the foot, and the lateral side of the foot.

20. The apparatus of claim 2, wherein the support layer is configured to extend from below the plantar of the foot up to leg of the patient.

21. The apparatus of claim 20, wherein the support layer comprises an upper portion that is configured to extend at least a partially radially around the leg of the patient.

22. The apparatus of claim 1, wherein the support layer includes a plurality of apertures, and wherein when negative pressure is applied to the tissue interface, the cover is configured to be pulled against the support layer such that an outline of at least a portion of the apertures are visible through the cover.

23. The apparatus of claim 1, wherein the anatomical shape is configured to cover a knee.

24. The apparatus of claim 23, wherein the tissue interface is further configured to cover the knee, a portion of the leg above the knee, and a portion of the leg below the knee.

25. The apparatus of claim 23, wherein:
    the cover has first end and a second end; and
    the first end and the second end are open.

26. The apparatus of claim 1, wherein the support layer comprises neoprene.

* * * * *